United States Patent
Eskildsen et al.

(10) Patent No.: US 9,050,327 B2
(45) Date of Patent: *Jun. 9, 2015

(54) POSITIVE ALLOSTERIC MODULATORS OF NICOTINIC ACETYLCHOLINE RECEPTOR

(71) Applicant: H. Lundbeck A/S, Valby-Copenhagen (DK)

(72) Inventors: Jørgen Eskildsen, København S (DK); Anette Graven Sams, Værløse (DK); Ask Püschl, Frederiksberg C. (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/054,941

(22) Filed: Oct. 16, 2013

(65) Prior Publication Data

US 2014/0044806 A1    Feb. 13, 2014

Related U.S. Application Data

(63) Continuation of application No. 13/542,687, filed on Jul. 6, 2012, now Pat. No. 8,598,213.

(60) Provisional application No. 61/505,847, filed on Jul. 8, 2011.

(51) Int. Cl.

| | |
|---|---|
| *C07D 213/71* | (2006.01) |
| *C07D 239/34* | (2006.01) |
| *C07D 405/12* | (2006.01) |
| *A61K 31/4355* | (2006.01) |
| *A61K 31/44* | (2006.01) |
| *A61K 31/505* | (2006.01) |
| *C07D 213/74* | (2006.01) |
| *C07D 213/84* | (2006.01) |
| *C07D 213/85* | (2006.01) |
| *C07D 491/056* | (2006.01) |
| *C07D 213/40* | (2006.01) |
| *C07D 213/61* | (2006.01) |
| *C07D 213/647* | (2006.01) |
| *C07D 213/65* | (2006.01) |
| *A61K 31/443* | (2006.01) |
| *A61K 31/4433* | (2006.01) |
| *A61K 45/06* | (2006.01) |
| *A61K 31/4427* | (2006.01) |
| *A61K 31/436* | (2006.01) |

(52) U.S. Cl.
CPC .......... *A61K 31/4355* (2013.01); *C07D 213/71* (2013.01); *C07D 213/74* (2013.01); *C07D 213/84* (2013.01); *C07D 213/85* (2013.01); *C07D 239/34* (2013.01); *C07D 405/12* (2013.01); *C07D 491/056* (2013.01); *C07D 213/40* (2013.01); *C07D 213/61* (2013.01); *C07D 213/647* (2013.01); *C07D 213/65* (2013.01); *A61K 31/44* (2013.01); *A61K 31/443* (2013.01); *A61K 31/4433* (2013.01); *A61K 45/06* (2013.01); *A61K 31/4427* (2013.01); *A61K 31/436* (2013.01); *A61K 31/505* (2013.01)

(58) Field of Classification Search
None
See application file for complete search history.

(56) References Cited

U.S. PATENT DOCUMENTS

| 8,598,213 B2 * | 12/2013 | Eskildsen et al. ............. 514/347 |
| 2013/0012530 A1 | 1/2013 | Eskildsen et al. |
| 2014/0010897 A1 | 1/2014 | Sams et al. |
| 2014/0010898 A1 | 1/2014 | Eskildsen et al. |

FOREIGN PATENT DOCUMENTS

| WO | 2009/043784 A1 | 4/2009 |
| WO | 2010/137351 A1 | 12/2010 |
| WO | 2011/044195 A1 | 4/2011 |

OTHER PUBLICATIONS

International Search Report and Written Opinion issued Sep. 26, 2013 in International Application No. PCT/EP2013/064093 filed Jul. 4, 2013.
International Search Report and Written Opinion issued Sep. 24, 2013 in International Application No. PCT/EP2013/064088 filed Jul. 4, 2013.
International Search Report and Written Opinion issued Oct. 16, 2012 in International Application No. PCT/EP2012/003219 filed Jul. 6, 2012.
Dinklo et al., 2011, "Characterization of 2-[[4-Fluoro-3-(trifluoromethyl)phenyl]amino]-4-(4-pyridinly)-5-thiazolemethanel (JNJ-1930942), a Nagel Positive Allosteric Modulator of the α7 Nicotinic Acetylchaline Receptor" Journal of Pharmacolody and Experimental Therapeutics, vol. 336, No. 2, pp. 560-574.
Faghih et al., 2007. "Advances in the Discovery of Novel Positive Allosteric Modulators of the α7 Nicotinic Acetylcholine Receptor" Recent Patents on CNS Drug Discovery, 2, pp. 99-106.
Gundisch et al., 2011, "Nicotinic acetylcholine receptor liglanois a patent review (2006-2011)"Expert Opinion, Ther. Patents, 21(12), pp. 1867-1895.
Hurst et al., 2005, "A Novel Positive Allosteric Modulator of the α7 Neuronal Nicotinic Acetylcholine Receptor: In Vitro and In Vivo Characterization", The Journal of Neuroscience, 25(17), pp. 4396-4405.

(Continued)

*Primary Examiner* — Zinna Northington Davis

(74) *Attorney, Agent, or Firm* — Mary Catherine Di Nunzio

(57) ABSTRACT

The present invention relates to compounds useful in therapy, to compositions comprising said compounds, and to methods of treating diseases comprising administration of said compounds. The compounds referred to are positive allosteric modulators (PAMs) of the nicotinic acetylcholine α7 receptor.

18 Claims, No Drawings

(56) References Cited

OTHER PUBLICATIONS

Ng et al., 2007, "Noctropic α7 nicotinic receptor allosteric modulator derived from GABAA receptor modulators", PNAS, vol. 104, No. 19. pp. 8050-8064.

Timmermann et al., 2007, "An Allosteric Modulator of the α7 Nicotinic Acetylcholine Receptor Possessing Cognition-Enhancing Properties in Vivo", The Journal of Pharmacology and Experimental Therapeutics, vol. 323, No. 1, pp. 294-307.

* cited by examiner

POSITIVE ALLOSTERIC MODULATORS OF NICOTINIC ACETYLCHOLINE RECEPTOR

CROSS-REFERENCE TO RELATED APPLICATIONS

The present application is a Continuation of U.S. Non Provisional application Ser. No. 13/542,687 filed Jul. 6, 2012, now U.S. Pat. No. 8,598,213, which claims benefit of priority under 35 U.S.C. §119(e) of U.S. Provisional Application No. 61/505,847, filed Jul. 8, 2011.

FIELD OF THE INVENTION

The present invention relates to compounds useful in therapy, to compositions comprising said compounds, and to methods of treating diseases comprising administration of said compounds. The compounds referred to are positive allosteric modulators (PAMs) of the nicotinic acetylcholine α7 receptor.

BACKGROUND OF THE INVENTION

Nicotinic acetylcholine receptors (nAChRs) belong to the super family of ligand gated ionic channels, and gate the flow of cations including calcium. The nAChRs are endogenously activated by acetylcholine (ACh) and can be divided into nicotinic receptors of the neuromuscular junction and neuronal nicotinic receptors (NNRs). The NNRs are widely expressed throughout the central nervous system (CNS) and the peripheral nervous system (PNS). The NNRs have been suggested to play an important role in CNS function by modulating the release of many neurotransmitters, for example, ACh, norepinephrine, dopamine, serotonin, and GABA, among others, resulting in a wide range of physiological effects.

Seventeen subunits of nAChRs have been reported to date, which are identified as $\alpha 2$-$\alpha 10$, $\beta 1$-$\beta 4$, $\gamma$, $\delta$ and $\epsilon$. From these subunits, nine subunits, $\alpha 2$ through $\alpha 7$ and $\beta 2$ through $\beta 4$, prominently exist in the mammalian brain. Many functionally distinct nAChR complexes exist, for example five $\alpha 7$ subunits can form a receptor as a homomeric functional pentamer or combinations of different subunits can form heteromeric receptors such as $\alpha 4\beta 2$ and $\alpha 3\beta 4$ receptors (Gotti, C. et al., *Prog. Neurobiol.*, 2004, 74: 363-396; Gotti, C. et al., *Biochemical Pharmacology*, 2009, 78: 703-711)

The homomeric $\alpha 7$ receptor is one of the most abundant NNRs, along with $\alpha 4\beta 2$ receptors, in the brain, wherein it is heavily expressed in the hippocampus, cortex, thalamic nuclei, ventral tegmental area and substantia nigra (Broad, L. M. et al., *Drugs of the Future*, 2007, 32(2): 161-170, Poorthuis R B, *Biochem Pharmacol.* 2009, 1; 78(7):668-76).

The role of $\alpha 7$ NNR in neuronal signaling has been actively investigated. The $\alpha 7$ NNRs have been demonstrated to regulate interneuron excitability and modulate the release of excitatory as well as inhibitory neurotransmitters. In addition, $\alpha 7$ NNRs have been reported to be involved in neuroprotective effects in experimental models of cellular damage (Shimohama, S., *Biol Pharm Bull.* 2009, 32(3):332-6). Studies have shown that $\alpha 7$ subunits, when expressed recombinant in-vitro, activate and desensitize rapidly, and exhibit relatively higher calcium permeability compared to other NNR combinations (Papke, R. L. et al., *J Pharmacol Exp Ther.* 2009, 329(2):791-807).

The NNRs, in general, are involved in various cognitive functions, such as learning, memory and attention, and therefore in CNS disorders, i.e., Alzheimer's disease (AD), Parkinson's disease (PD), attention deficit hyperactivity disorder (ADHD), Tourette's syndrome, schizophrenia, bipolar disorder, pain and tobacco dependence (Keller J. J. et al., *Behav. Brain Res.* 2005, 162: 143-52; Haydar, S. N. et al., *Curr Top Med Chem.* 2010; 10(2):144-52).

The $\alpha 7$ NNRs in particular, have also been linked to cognitive disorders including, for example, ADHD, autism spectrum disorders, AD, mild cognitive impairment (MCI), age associated memory impairment (AAMI) senile dementia, frontotemporal lobar degeneration, HIV associated dementia (HAD). HIV associated cognitive impairment (HIV-CI), Pick's disease, dementia associated with Lewy bodies, cognitive impairment associated with Multiple Sclerosis, Vascular Dementia, cognitive impairment in Epilepsy, cognitive impairment associated with fragile X, cognitive impairment associated with Friedreich's Ataxia, and dementia associated with Down's syndrome, as well as cognitive impairment associated with schizophrenia. In addition, $\alpha 7$-NNRs have been shown to be involved in the neuroprotective effects of nicotine both in vitro (Jonnala, R. B. et al., *J. Neurosci. Res.*, 2001, 66: 5665-572) and in vivo (Shimohama, S., *Brain Res.*, 1998, 779: 359-363) as well as in pain signalling. More particularly, neurodegeneration underlies several progressive CNS disorders, including, but not limited to, AD, PD, amyotrophic lateral sclerosis, Huntington's disease, dementia with Lewy bodies, as well as diminished CNS function resulting from traumatic brain injury. For example, the impaired function of $\alpha 7$ NNRs by beta-amyloid peptides linked to AD has been implicated as a key factor in development of the cognitive deficits associated with the disease (Liu, Q.-S., et al., *PNAS*, 2001, 98: 4734-4739). Thus, modulating the activity of $\alpha 7$ NNRs demonstrates promising potential to prevent or treat a variety of diseases indicated above, such as AD, other dementias, other neurodegenerative diseases, schizophrenia and neurodegeneration, with an underlying pathology that involves cognitive function including, for example, aspects of learning, memory, and attention (Thomsen, M. S. et al., *Curr Pharm Des.* 2010 January; 16(3):323-43; Olincy, A. et al., *Arch Gen Psychiatry.* 2006, 63(6):630-8: Deutsch, S. I., *Clin Neuropharmacol.* 2010, 33(3):114-20; Feuerbach, D., *Neuropharmacology* 2009, 56(1): 254-63).

The NNR ligands, including $\alpha 7$ ligands, have also been implicated in weight control, diabetis inflammation, obsessive-compulsive disorder (OCD), angiogenesis and as potential analgesics (Marrero, M. B. et al., *J. Pharmacol. Exp Ther.* 2010, 332(1):173-80; Vincler, M., *Exp. Opin. Invest. Drugs*, 2005, 14 (10): 1191-1 198; Rosas-Balina, M., *J. Intern Med.* 2009 285(6):663-79; Arias, H. R., *Int. J. Bochem. Cell Biol.* 2009, 41(7):1441-51; Tizabi, Y., *Biol Psychiatry.* 2002, 51(2): 164-71).

Nicotine is known to enhance attention and cognitive performance, reduced anxiety, enhanced sensory gating, and analgesia and neuroprotective effects when administered. Such effects are mediated by the non-selective effect of nicotine at multiple nicotinic receptor subtypes. However, nicotine also exerts adverse events, such as cardiovascular and gastrointestinal problems (Karaconji, I. B. et al., *Arh Hig Rada Toksikol.* 2005, 56(4):363-71). Consequently, there is a need to identify subtype-selective compounds that retain the beneficial effects of nicotine, or an NNR ligand, while eliminating or decreasing adverse effects.

Examples of reported NNR ligands are $\alpha 7$ NNR agonists, such as DMXB-A, SSR180711 and ABT-107, which have shown some beneficial effects on cognitive processing both in rodents and humans (H312: 1213-22; Olincy, A. et al., *Arch Gen Psychiatry.* 2006 63(6):630-8; Pichat, P., at al., *Neuropsychopharmacology.* 2007 32(1):17-34; Bitner, R. S., *J Phar-* macol Exp Ther. 2010 1; 334(3):875-86). In addition, modulation of α7 NNRs have been reported to improve negative symptoms in patients with schizophrenia (Freedman, R. et al., *Am J Psychiatry.* 2008 165(8):1040-7).

Despite the beneficial effects of NNR ligands, it remains uncertain whether chronic treatment with agonists affecting NNRs may provide suboptimal benefit due to sustained activation and desensitization of the NNRs, in particular the α7 NNR subtype. In contrast to agonists, administering a positive allosteric modulator (PAM) can reinforce endogenous cholinergic transmission without directly stimulating the target receptor. Nicotinic PAMs can selectively modulate the activity of ACh at NNRs, preserving the activation and deactivation kinetics of the receptor. Accordingly, α7 NNR-selective PAMs have emerged (Faghih, R., *Recent Pat CNS Drug Discov.* 2007, 2(2):99-106).

Consequently, it would be beneficial to increase α7 NNR function by enhancing the effect of the endogenous neurotransmitter acetylcholine via PAMs. This could reinforce the endogenous cholinergic neurotransmission without directly activating α7 NNRs, like agonists. Indeed, PAMs for enhancing channel activity have been proven clinically successful for GABAa receptors where benzodiazepines and barbiturates, behave as PAMs acting at distinct sites (Hevers, W. et al., *Mol. Neurobiol.,* 1998 18: 35-86).

To date, only a few NNR PAMs are known, such as 5-hydroxyindole (5-HI), ivermectin, galantamine, and SLURP-1, a peptide derived from acetylcholinesterase (AChE). Genistein, a kinase inhibitor was also reported to increase α7 responses. PNU-120596, a urea derivative, was reported to increase the potency of ACh as well as improve auditory gating deficits induced by amphetamine in rats. Also, NS1738, JNJ-1930942 and compound 6 have been reported to potentiate the response of ACh and exert beneficial effect in experimental models of sensory and cognitive processing in rodents. Other NNR PAMs include derivatives of quinuclidine, indole, benzopyrazole, thiazole, and benzoisothiazoles (Hurst, R. S. et al., *J. Neurosci.* 2005, 25: 4396-4405; Faghih, R., *Recent Pat CNS Drug Discov.* 2007, 2(2):99-106; Timmermann, O. B., *J. Pharmacol. Exp. Ther.* 2007, 323(1):294-307; Ng, H. J. et al., *Proc. Natl. Acad. Sci. USA.* 2007, 8; 104(19):8059-64; Dinklo, T., *J. Pharmacol. Exp. Ther.* 2011, 336(2):560-74).

WO 2009/043784 recites compounds of the overall structure

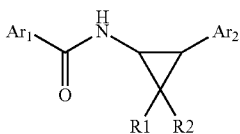

which compounds are said to be PAMs of the α7 NNR.

The α7 NNR PAMs presently known generally demonstrate weak activity, have a range of non-specific effects, or can only achieve limited access to the central nervous system where α7 NNRs are abundantly expressed. Accordingly, it would be beneficial to identify and provide new PAM compounds of α7 NNRs and compositions for treating diseases and disorders wherein α7 NNRs and involved. It would further be particularly beneficial if such compounds can provide improved efficacy of treatment while reducing adverse effects associated with compounds targeting neuronal nicotinic receptors by selectively modulating α7 NNRs.

WO 2010/137351 recites compounds of the overall structure

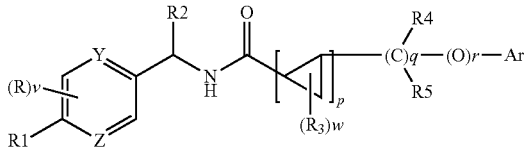

as calcium or sodium channel blockers. Compound examples disclosed in WO 2010/137351 are not intended to be included in the present invention.

Particularly the compounds (1S,2S)-2-Phenyl-cyclopropanecarboxylic acid {(S)-1-[5-(2,2,2-trifluoro-ethoxy)-pyridin-2-yl]-ethyl}-amide, (1S,2S)-2-(2-Chloro-4-fluoro-phenyl)-cyclopropanecarboxylic acid {(S)-1-[5-(2,2,2-trifluoro-ethoxy)-pyridin-2-yl]-ethyl}-amide and (1S,2S)-2-(2-Fluoro-4-methoxy-phenyl)-cyclopropanecarboxylic acid {(S)-1-[5-(2,2,2-trifluoro-ethoxy)-pyridin-2-yl]-ethyl}-amide are disclosed in WO 2010/137351 are disclaimed from the present invention

SUMMARY OF THE INVENTION

The objective of the present invention is to provide compounds that are positive allosteric modulators (PAMs) of the nicotinic acetylcholine receptor subtype α7.

The compounds of the present invention are defined by formula [I] below:

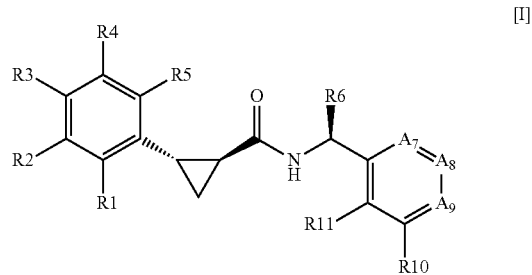

wherein R1, R2, R3, R4 and R5 are selected independently of each other from H, $C_{1-6}$alkyl, $C_{2-6}$alkenyl, $C_{2-6}$alkynyl, $C_{1-6}$alkoxy, cyano and halogen, wherein said $C_{1-6}$alkyl, $C_{2-6}$alkenyl and $C_{2-6}$alkynyl is optionally substituted with one or more substituents independently selected from chlorine and fluorine;

R6 is selected from $C_{1-6}$alkyl, $C_{2-6}$alkenyl, $C_{2-6}$alkynyl and $C_{1-6}$alkoxy, wherein said $C_{1-6}$alkyl, $C_{2-6}$alkenyl and $C_{2-6}$alkynyl is optionally substituted with one or more substituents independently selected from hydroxy, $C_{1-6}$alkoxy and fluorine;

A7 is C—R7 or N, A8 is C—R8 or N and A9 is C—R9 or N, provided that at least one of A7, A8 or and 9 is N and no more than two of A7, A8 and A9 is N;

R7, R8, R9, R10 and R11 are selected independently of each other from H, $C_{1-6}$alkyl, $C_{2-6}$alkenyl, $C_{2-6}$alkynyl, $C_{1-6}$alkoxy, cyano, NR12R13, $C_{1-6}$alkylsulfonyl, halogen and OR14, wherein said $C_{1-6}$alkyl, $C_{2-6}$alkenyl, $C_{2-6}$alkynyl or $C_{1-6}$alkoxy is optionally substituted with one or more substituents selected from chlorine, fluorine, $C_{1-6}$alkoxy, cyano and NR12R13;

R12 and R13 independently represent hydrogen, $C_{1-6}$alkyl, $C_{2-6}$alkenyl and $C_{2-6}$alkynyl;

R14 represents a monocyclic saturated ring moiety having 4-6 ring atoms wherein one of said ring atoms is O and the others are C;

or R9 and R10 may be linked together to form the moiety indicated below

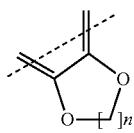

wherein n is 1, 2 or 3;
and pharmaceutically acceptable salts thereof;
with the proviso that the compound of formula [I] is other than
(1S,2S)-2-Phenyl-cyclopropanecarboxylic acid {(S)-1-[5-(2,2,2-trifluoro-ethoxy)-pyridin-2-yl]-ethyl}-amide;
(1S,2S)-2-(2-Chloro-4-fluoro-phenyl)-cyclopropanecarboxylic acid {(S)-1-[5-(2,2,2-trifluoro-ethoxy)-pyridin-2-yl]-ethyl}-amide;
(1S,2S)-2-(2-Fluoro-4-methoxy-phenyl)-cyclopropanecarboxylic acid {(S)-1-[5-(2,2,2-trifluoro-ethoxy)-pyridin-2-yl]-ethyl}-amide.

In one embodiment, the invention relates to a compound according to formula [I], and pharmaceutically acceptable salts thereof, for use as a medicament.

In one embodiment, the invention relates to a compound according to formula [I], and pharmaceutically acceptable salts thereof, for use in therapy.

In one embodiment, the invention relates to a compound according to formula [I], and pharmaceutically acceptable salts thereof, for use in the treatment of a disease or disorder selected from Psychosis; Schizophrenia; cognitive disorders; cognitive impairment associated with schizophrenia; Attention Deficit Hyperactivity Disorder (ADHD); autism spectrum disorders, Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's Disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain.

In one embodiment, the invention relates to a pharmaceutical composition comprising a compound according to formula [I] and pharmaceutically acceptable salts thereof, and one or more pharmaceutically acceptable carrier or excipient.

In one embodiment, the invention relates to a kit comprising a compound according to formula [I], and pharmaceutically acceptable salts thereof, together with a compound selected from the list consisting of acetylcholinesterase inhibitors; glutamate receptor antagonists; dopamine transport inhibitors; noradrenalin transport inhibitors; D2 antagonists, D2 partial agonists; PDE10 antagonists; 5-HT2A antagonists; 5-HT6 antagonists; KCNQ antagonists; lithium; sodium channel blockers and GABA signaling enhancers.

In one embodiment, the invention relates to a method for the treatment of a disease or disorder selected from Psychosis; Schizophrenia; cognitive disorders; cognitive impairment associated with schizophrenia; Attention Deficit Hyperactivity Disorder (ADHD); autism spectrum disorders, Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's Disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain, which method comprises the administration of a therapeutically-effective amount of a compound according to formula [I], and pharmaceutically acceptable salts thereof.

In one embodiment, the invention relates to the use of a compound according to formula [I], and pharmaceutically acceptable salts thereof, for the manufacture of a medicament for the treatment of a disease or disorder selected from Psychosis; Schizophrenia; cognitive disorders; cognitive impairment associated with schizophrenia; Attention Deficit Hyperactivity Disorder (ADHD); autism spectrum disorders, Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's Disease; Parkinson's disease (PD); obsessive-compulsive disorder (OCD); traumatic brain injury; epilepsy; post-traumatic stress; Wernicke-Korsakolf syndrome (WKS); post-traumatic amnesia; cognitive deficits associated with depression; diabetes, weight control, inflammatory disorders, reduced angiogenesis; amyotrophic lateral sclerosis and pain.

Definitions

In the present context, "optionally substituted" means that the indicated moiety may or may not be substituted, and when substituted is mono-, di-, or tri-substituted, such as with 1, 2 or 3 substituents. In some instances, the substituent is independently selected from the group consisting of $C_{1-6}$alkyl, $C_{2-6}$alkenyl, $C_{2-6}$alkynyl, phenyl, $C_{1-6}$alkoxy, hydroxy and halogen. It is understood that where no substituents are indicated for an "optionally substituted" moiety, then the position is held by a hydrogen atom.

In the present context, "alkyl" is intended to indicate a straight, branched and/or cyclic saturated hydrocarbon. In particular "$C_{1-6}$alkyl" is intended to indicate such hydrocarbon having 1, 2, 3, 4, 5 or 6 carbon atoms. Examples of $C_{1-6}$alkyl include methyl, ethyl, propyl, butyl, pentyl, hexyl, cyclopropyl, cyclobutyl, cyclopentyl, cyclohexyl, methylcyclopropyl, 2-methyl-propyl and tert-butyl. Examples of substituted $C_{1-6}$alkyl include e.g. fluoromethyl and hydroxymethyl.

In the present context, "alkenyl" is intended to indicate a non-aromatic, straight, branched and/or cyclic hydrocarbon comprising at least one carbon-carbon double bond. In particular "$C_{2-6}$alkenyl" is intended to indicate such hydrocarbon having 2, 3, 4, 5 or 6 carbon atoms. Examples of $C_{2-6}$alkenyl include ethenyl, 1-propenyl, 2-propenyl, 1-butenyl, 2-butenyl and 3-butenyl and cyclohexenyl.

In the present context, "alkynyl" is intended to indicate a non-aromatic, straight, branched and/or cyclic hydrocarbon comprising at least one carbon-carbon triple bond and optionally also one or more carbon-carbon double bonds. In particular "$C_{2-6}$alkynyl" is intended to indicate such hydrocarbon having 2, 3, 4, 5 or 6 carbon atoms. Examples of $C_{2-6}$alkynyl include ethynyl, 1-propynyl, 2-propynyl, 1-butynyl, 2-butynyl, 3-butynyl and 5-but-1-en-3-ynyl.

In the present context, "hydroxy" is intended to indicate —OH.

In the present context, "alkoxy" is intended to indicate a moiety of the formula —OR', wherein R' indicates alkyl as defined above. In particular "$C_{1-6}$alkoxy" is intended to indicate such moiety wherein the alkyl part has 1, 2, 3, 4, 5 or 6 carbon atoms. Examples of "$C_{1-6}$alkoxy" include methoxy, ethoxy, n-butoxy and tert-butoxy.

In the present context, "alkylsulfonyl" is intended to indicate —S(O)$_2$alkyl In particular $C_{1-6}$alkysulfonyl is intended to indicate such a moiety wherein the alkyl part has 1, 2, 3, 4, 5 or 6 carbon atoms. Particular mention is made of methylsulfonyl.

In the present context, a "monocyclic moiety" is intended to cyclic moiety comprising only one ring, said cyclic moiety can be saturated or unsaturated.

In the present context, the terms "halo" and "halogen" are used interchangeably and refer to fluorine, chlorine, bromine or iodine.

In the present context, the term "cyano" indicates the group —CN≡N, which consists of a carbon atom triple-bonded to a nitrogen atom.

In the present context, "ring atom" is intended to indicate the atoms constituting a ring, and ring atoms are selected from C, N, O and S. As an example, benzene and toluene both have 6 carbons as ring atoms whereas pyridine has 5 carbons and 1 nitrogen as ring atoms.

In the present context, "heteroatom" means a nitrogen, oxygen or sulfur atom.

In the present context, "deuterium" indicates the atomic isotope of hydrogen consisting of one proton and one neutron in its nucleus, and thus having an approximate weight of two (2). Deuterium is represented as D, d or $^2$H. An example of a substituent comprising deuterium is (2,2,2-d$_3$)-ethoxy wherein three of the hydrogens in ethoxy are the $^2$H isotopes.

In the present context, "enantiomeric excess" represents the % excess of a compound in a mixture of compound enantiomers. If for example an enantiomeric excess is 90% then the ratio of the compound to its enantiomer is 95:5 and if an enantiomeric excess is 95% then the ratio of the compound to its enantiomer is 97.5:2.5. Likewise, "diastereomeric excess" represents % excess of a compound in a mixture of compound diastereomers.

In the present context, pharmaceutically acceptable salts include pharmaceutically acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in Berge, S. M. et al., *J. Pharm. Sci.* 1977, 66, 2, which is incorporated herein by reference.

Examples of metal salts include lithium, sodium, potassium, magnesium salts and the like.

Examples of ammonium and alkylated ammonium sells include ammonium, methyl-, dimethyl-, trimethyl-, ethyl-, hydroxyethyl-, diethyl-, n-butyl-, sec-butyl-, tert-butyl-, tetramethylammonium salts and the like.

In the present context, pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier may include any sustained release material known in the art, such as glyceryl monostearate or glyceryl distearate, alone or mixed with a wax.

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the present invention. The patient to be treated is preferably a mammal, in particular a human being.

In the present context, the term "cognitive disorders" is intended to indicate disorders characterized by abnormalities in aspects of perception, problem solving, language, learning, working memory, memory, social recognition, attention and pre-attentional processing, such as by not limited to Attention Deficit Hyperactivity Disorder (ADHD), autism spectrum disorders, Alzheimer's disease (AD), mild cognitive impairment (MCI), age associated memory impairment (AAMI), senile dementia, vascular dementia, frontotemporal lobe dementia, Pick's disease, dementia associated with Lewy bodies, and dementia associated with Down's syndrome, cognitive impairment associated with Multiple Sclerosis, cognitive impairment in epilepsy, cognitive impairment associated with fragile X, cognitive impairment associated with neurofibromatosis, cognitive impairment associated with Friedreich's Ataxia, progressive supranuclear palsy (PSP), HIV associated dementia (HAD), HIV associated cognitive impairment (HIV-CI), Huntington's Disease, Parkinson's disease (PD), obsessive-compulsive disorder (OCD), traumatic brain injury, epilepsy, post-traumatic stress, Wernicke-Korsakoff syndrome (WKS), post-traumatic amnesia, cognitive deficits associated with depression as well as cognitive impairment associated with schizophrenia.

The cognitive enhancing properties of a compound can be assessed e.g. by the attentional set-shifting paradigm which is an animal model slowing assessment of executive functioning via intra-dimensional (ID) versus extra-dimensional (ED) shift discrimination learning. The study can be performed by testing whether the compound is attenuating "attentional performance impairment" induced by subchronic PCP administration in rats as described by Rodefer, J. S. et al., *Eur. J. Neurosci.* 2005, 21:1070-1076.

In the present context, the term "autism spectrum disorders" is intended to indicate disorders characterized by widespread abnormalities of social interactions and verbal and non-verbal communication, as well as restricted interests, repetitive behavior and attention, such as by not limited to autism. Asperger syndrome, Pervasive Developmental Disorder Not Otherwise Specified (PDD-NOS), Rett syndrome, Angelmann syndrome, fragile X, DiGeorge syndrome and Childhood Disintegrative Disorder.

In the present context, the term "inflammatory disorders" is intended to indicate disorders characterized by abnormalities in the immune system such as by not limited to, allergic reactions and myopathies resulting in abnormal inflammation as well as non-immune diseases with etiological origins in inflammatory processes are thought to include but not be limited to cancer, atherosclerosis, osteoarthritis, rheumatoid arthritis and ischaemic heart disease.

DETAILED DESCRIPTION OF THE INVENTION

The present inventors have found that certain new compounds are positive allosteric modulators (PAMs) of NNRs, and as such may be used in the treatment of various disorders.

PAMs of NNRs may be dosed in combination with other drugs in order to achieve more efficacious treatment in certain patient populations. An α7 NNR PAM may act synergistically with another drug, this has been described in animals for the combination of compounds affecting nicotinic receptors, including α7 NNRs and D2 antagonism (Wiker, C., *Int. J. Neuropsychopharmacol.* 2008, 11(6):845-50).

Thus, compounds of the present invention may be useful treatment in the combination with another drug e.g. selected from acetylcholinesterase inhibitors, glutamate receptor antagonists, dopamine transport inhibitors, noradrenaline transport inhibitors, D2 partial agonists, PDE10 antagonists, 5-HT2A antagonists, 5-HT6 antagonists and KCNQ antagonists, lithium, sodium channel blockers, GABA signalling enhancers.

In one embodiment, compounds of the present invention are used for treatment of patients who are already in treatment with another drug selected from the list above. In one embodiment, compounds of the present invention are adapted for administration simultaneous with said other drug. In one embodiment compounds of the present invention are adapted for administration sequentially with said other drug. In one embodiment, compounds of the present invention are used as the sole medicament in treatment of a patient. In one embodiment, compounds of the present invention are used for treatment of patients who are not already in treatment with another drug selected from the list above.

Embodiments According to the Invention

In the following, embodiments of the invention are disclosed. The first embodiment is denoted E1, the second embodiment is denoted E2 and so forth.

E1. A compound according to formula [I]

[I]

wherein R1, R2, R3, R4 and R5 are selected independently of each other from H, $C_{1-6}$alkyl, $C_{2-6}$alkenyl, $C_{2-6}$alkynyl, $C_{1-6}$alkoxy, cyano and halogen, wherein said $C_{1-6}$alkyl, $C_{2-6}$alkenyl and $C_{2-6}$alkynyl is optionally substituted with one or more substituents independently selected from chlorine and fluorine;

R6 is selected from $C_{1-6}$alkyl, $C_{2-6}$alkenyl, $C_{2-6}$alkynyl and $C_{1-6}$alkoxy, wherein said $C_{1-6}$alkyl, $C_{2-6}$alkenyl and $C_{2-6}$alkynyl is optionally substituted with one or more substituents independently selected from hydroxy, $C_{1-6}$alkoxy and fluorine;

A7 is C—R7 or N, A8 is C—R8 or N and A9 is C—R9 or N, provided that a least one of A7, A8 or and 9 is N and no more than two of A7, A8 and A9 is N;

R7, R8, R9, R10 and R11 are selected independently of each other from H, $C_{1-6}$alkyl, $C_{2-6}$alkenyl, $C_{2-6}$alkynyl, $C_{1-6}$alkoxy, cyano, NR12R13, $C_{1-6}$alkylsulfonyl, halogen and OR14, wherein said $C_{1-6}$alkyl, $C_{2-6}$alkenyl, $C_{2-6}$alkynyl or $C_{1-6}$alkoxy is optionally substituted with one or more substituents selected from chlorine, fluorine, $C_{1-6}$alkoxy, cyano and NR12R13;

R12 and R13 independently represent hydrogen, $C_{1-6}$alkyl, $C_{2-6}$alkenyl and $C_{2-6}$alkynyl;

R14 represents a monocyclic saturated ring moiety having 4-6 ring atoms wherein one of said ring atoms is O and the others are C;

or R9 and R10 may be linked together to form the moiety indicated below wherein n is 1, 2 or 3;
and pharmaceutically acceptable salts thereof;
with the proviso that the compound of formula [I] is other than
(1S,2S)-2-Phenyl-cyclopropanecarboxylic acid {(S)-1-[5-(2,2,2-trifluoro-ethoxy)-pyridin-2-yl]-ethyl}-amide;
(1S,2S)-2-(2-Chloro-4-fluoro-phenyl)-cyclopropanecarboxylic acid {(S)-1-[5-(2,2,2-trifluoro-ethoxy)-pyridin-2-yl]-ethyl}-amide;
(1S,2S)-2-(2-Fluoro-4-methoxy-phenyl)-cyclopropanecarboxylic acid {(S)-1-[5-(2,2,2-trifluoro-ethoxy)-pyridin-2-yl]-ethyl}-amide.

E2. The compound according to embodiment 1, wherein R1, R2, R3, R4 and R5 are selected independently of each other from H, methyl, fluorine and chlorine;

R6 is selected from methyl, hydroxymethyl, methoxymethyl and fluoromethyl;
R7, R8, R9, R10 and R11 are selected independently of each other from H, $C_{1-4}$alkyl, $C_{1-4}$alkoxy; cyano, —N(CH$_3$)$_2$, methylsulfonyl, fluorine, chlorine and OR14, wherein said $C_{1-4}$alkyl or $C_{1-4}$alkoxy is optionally substituted with one or more substituents selected from fluorine, $C_{1-4}$alkoxy and cyano;
R14 represents a monocyclic saturated ring moiety having 4-6 ring atoms wherein one of said ring atoms is O and the others are C;
or R9 and R10 may be linked together to form the moiety indicated below

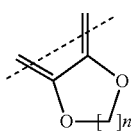

wherein n is 1 or 2.
E3. The compound according to any of embodiments 1-2, wherein R1, R2, R3, R4 and R5 are selected independently of each other from H, methyl, fluorine and chlorine.
E4. The compound according to any of embodiments 1-3, wherein four or more of R1, R2, R3, R4 and R5 are H.
E5. The compound according to embodiment 4, wherein all of R1, R2, R3, R4 and R5 are H.
E6. The compound according to any of embodiments 1-5, wherein R6 is selected from methyl, hydroxymethyl, methoxymethyl and fluoromethyl.
E7. The compound according to embodiment 6, wherein R6 is methyl.
E8. The compound according to embodiment 6, wherein R6 is hydroxymethyl.
E9. The compound according to embodiment 8, wherein R6 is methoxymethyl.
E10. The compound according to embodiment 6, wherein R6 is fluoromethyl.
E11. The compound according to any of embodiments 1-10, wherein R7, R8, R9, R10 and R11 are selected independently of each other from H, $C_{1-4}$alkyl, $C_{1-4}$alkoxy, cyano, —N(CH$_3$)$_2$, methylsulfonyl, fluorine, chlorine and OR14, wherein said $C_{1-4}$alkyl or $C_{1-4}$alkoxy is optionally substituted with one or more substituents selected from fluorine, $C_{1-4}$alkoxy and cyano;
R14 represents a monocyclic saturated ring moiety having 4-6 ring atoms wherein one of said ring atoms is O and the others are C;
or R9 and R10 may be linked together to form the moiety indicated below

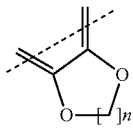

wherein n is 1 or 2;
E12. The compound according to any of embodiments 1 and 3-11, wherein R7, R8, R9, R10 and R11 are selected independently from H, $C_{1-6}$alkyl, $C_{2-6}$alkenyl, $C_{1-6}$alkynyl, $C_{1-6}$alkoxy, cyano or halogen, wherein said $C_{1-6}$alkyl, $C_{2-6}$alkenyl, $C_{2-6}$alkynyl or $C_{1-6}$alkoxy is optionally substituted with one or more substituents selected from fluorine, $C_{1-6}$alkoxy and cyano.
E13. The compound according to any of embodiments 1-12, wherein R7, R8, R9, R10 and R11 are selected independently from H, $C_{1-4}$alkyl, $C_{2-4}$alkenyl, $C_{2-4}$alkynyl, $C_{1-4}$alkoxy, cyano and halogen, wherein said $C_{1-4}$alkyl, $C_{2-4}$alkenyl, $C_{2-4}$alkynyl or $C_{1-4}$alkoxy is optionally substituted with one or more substituents selected from fluorine and $C_{1-4}$alkoxy.
E14. The compound according to any of embodiments 1-13, wherein one or more of the hydrogen atoms are represented by deuterium.
E15. The compound according to embodiment 14, wherein one or more of the hydrogen atoms in R7, R8, R9, R10 and R11 are represented by deuterium.
E16. The compound according to any of embodiments 14-15, wherein at least about 85% of the compound has a deuterium atom at each position designated as deuterium, and any atom not designated as deuterium is present at about its natural isotopic abundance.
E17. The compound according to embodiment 16, wherein at least about 90% of the compound has a deuterium atom at each position designated as deuterium, and any atom not designated as deuterium is present at about its natural isotopic abundance.
E18. The compound according to any of embodiments 1-17, wherein no more than one of A7, A8 or A9 is N.
E19. The compound according to any of embodiments 1-18, wherein A7 is N, A8 is C—R8 and A9 is C—R9.
E20. The compound according to embodiment 19, wherein R8, R10 and R11 all represent H.
E21. The compound according to any of embodiments 1-18, wherein A8 is N, A7 is C—R7 and A9 is C—R9.
E22. The compound according to embodiment 21, wherein R7, R10 and R11 all represent H.
E23. The compound according to any of embodiments 19-22, wherein R9 is selected from methyl, $C_{1-4}$alkoxy or cyano, wherein said methyl is optionally substituted with $C_{1-4}$alkoxy or one or more fluorine.
E24. The compound according to embodiment 23, wherein R9 represents $C_{1-4}$alkoxy and one or more of the hydrogen atoms in said $C_{1-4}$alkoxy are represented by deuterium.
E25. The compound according to any of embodiments 19-22, wherein R9 is OR14, wherein R14 represents a monocyclic saturated ring moiety having 4-6 ring atoms wherein one of said ring atoms is O and the others are C.
E26. The compound according to any of embodiments 1-18, wherein A9 is N, A7 is C—R7 and A8 is C—R8.
E27. The compound according to embodiment 26, wherein R7, R8 and R11 all represent H.
E28. The compound according to any of embodiments 26-27, wherein R10 is selected from methyl, $C_{1-4}$alkoxy or cyano, wherein said methyl is optionally substituted with $C_{1-4}$alkoxy or one or more fluorine.
E29. The compound according to embodiment 28, wherein R10 represents $C_{1-4}$alkoxy and one or more of the hydrogen atoms in said $C_{1-4}$alkoxy are represented by deuterium.
E30. The compound according to any of embodiments 1-17, wherein two of A7, A8 or A9 are N.
E31. The compound according to any of embodiments 1-30 having a diastereomeric excess of at least 80% such as at least 85%, such as at least 90%, such as at least 95%.
E32. The compound according to embodiment 1 selected from
1: (1S,2S)-2-Phenyl-cyclopropanecarboxylic acid [(S)-1-(6-isopropoxy-pyridin-3-yl)-ethyl]-amide;

2: (1S,2S)-2-Phenyl-cyclopropanecarboxylic acid [(S)-1-(5-methyl-pyridin-2-yl)-ethyl]-amide;
3: (1S,2S)-2-Phenyl-cyclopropanecarboxylic acid [(S)-1-(6-methoxy-pyridin-3-yl)-ethyl]-amide;
4: (1S,2S)-2-Phenyl-cyclopropanecarboxylic acid [(S)-1-(6-methyl-pyridin-3-yl)-ethyl]-amide;
5: (1S,2S)-2-Phenyl-cyclopropanecarboxylic acid [(S)-1-(6-cyano-pyridin-3-yl)-ethyl]-amide;
6: (1S,2S)-2-Phenyl-cyclopropanecarboxylic acid [(S)-1-(6-trifluoromethyl-pyridin-3-yl)-ethyl]-amide;
7: (1S,2S)-2-Phenyl-cyclopropanecarboxylic acid [(S)-1-(6-ethoxy-pyridin-3-yl)-ethyl]-amide;
8: (1S,2S)-2-Phenyl-cyclopropanecarboxylic acid [(S)-1-(6-ethyl-pyridin-3-yl)-ethyl]-amide;
9: (1S,2S)-2-Phenyl-cyclopropanecarboxylic acid [(S)-1-(6-methoxymethyl-pyridin-3-yl)-ethyl]-amide;
10: (1S,2S)-2-Phenyl-cyclopropanecarboxylic acid {(S)-1-[6-(2,2,2-trifluo-ethoxy)-pyridin-3-yl]-ethyl}-amide;
11: (1S,2S)-2-Phenyl-cyclopropanecarboxylic acid {(S)-1-[6-(2-methoxy-ethoxy)-pyridin-3-yl]-ethyl}-amide;
12: (1S,2S)-2-Phenyl-cyclopropanecarboxylic acid [(S)-1-(2-ethoxy-pyridin-4-yl)-ethyl]-amide;
13: (1S,2S)-2-Phenyl-cyclopropanecarboxylic acid ((S)-1-{6-[(S)-(tetrahydro-furan-3-yl)oxy]-pyridin-3-yl}-ethyl)-amide;
14: (1S,2S)-2-Phenyl-cyclopropanecarboxylic acid ((S)-1-{6-[(R)-(tetrahydro-furan-3-yl)oxy]-pyridin-3-yl}-ethyl)-amide;
15: (1S,2S)-2-Phenyl-cyclopropanecarboxylic acid ((S)-1-[1,3]dioxolo[4,5-b]pyridin-6-yl-ethyl)-amide;
16: (1S,2S)-2-Phenyl-cyclopropanecarboxylic acid [(S)-1-(2,3-dihydro-[1,4]dioxino[2,3-b]pyridin-7-yl)-ethyl]-amide;
17: (1S,2S)-2-Phenyl-cyclopropanecarboxylic acid [(S)-1-(2-ethoxy-pyrimidin-5-yl)-ethyl]-amide;
18: (1S,2S)-2-Phenyl-cyclopropanecarboxylic acid [(S)-1-(6-chloro-pyridin-3-yl)-ethyl]-amide;
19: (1S,2S)-2-Phenyl-cyclopropanecarboxylic acid {(S)-1-[6-(oxetan-3-yloxy)-pyridin-3-yl]-ethyl}-amide;
20: (1S,2S)-2-Phenyl-cyclopropanecarboxylic acid [(S)-1-(6-cyanomethoxy-pyridin-3-yl)-ethyl]-amide;
21: (1S,2S)-2-Phenyl-cyclopropanecarboxylic acid [(R)-2-hydroxy-1-(6-propoxy-pyridin-3-yl)-ethyl]-amide;
22: (1S,2S)-2-Phenyl-cyclopropanecarboxylic acid [(R)-2-hydroxy-1-(6-trifluoromethyl-pyridin-3-yl)-ethyl]-amide;
23: (1S,2S)-2-Phenyl-cyclopropanecarboxylic acid [(R)-1-(5-cyano-pyridin-2-yl)-2-hydroxy-ethyl]-amide;
24: (1S,2S)-2-Phenyl-cyclopropanecarboxylic acid [(R)-2-hydroxy-1-(6-methoxy-pyridin-3-yl)-ethyl]-amide;
25: (1S,2S)-2-Phenyl-cyclopropanecarboxylic acid [(R)-2-hydroxy-1-(6-methyl-pyridin-3-yl)-ethyl]-amide;
26: (1S,2S)-2-Phenyl-cyclopropanecarboxylic acid [(R)-2-hydroxy-1-(6-isopropoxy-pyridin-3-yl)-ethyl]-amide;
27: (1S,2S)-2-(3-Fluoro-phenyl)-cyclopropanecarboxylic acid [(R)-1-(6-ethoxy-pyridin-3-yl)-2-hydroxy-ethyl]-amide;
28: (1S,2S)-2-(4-Fluoro-phenyl)-cyclopropanecarboxylic acid [(R)-1-(6-ethoxy-pyridin-3-yl)-2-hydroxy-ethyl]-amide;
29: (1S,2S)-2-(3-Fluoro-phenyl)-cyclopropanecarboxylic acid [(R)-2-hydroxy-1-(6-propoxy-pyridin-3-yl)-ethyl]-amide;
30: (1S,2S)-2-(4-Fluoro-phenyl)-cyclopropanecarboxylic acid [(R)-2-hydroxy-1-(6-propoxy-pyridin-3-yl)-ethyl]-amide;
31: (1S,2S)-2-Phenyl-cyclopropanecarboxylic acid [(R)-1-(6-(2,2,2-$d_3$)-ethoxy-pyridin-3-yl)-2-hydroxy-ethyl]-amide;
32: (1S,2S)-2-(3-Fluoro-phenyl)-cyclopropanecarboxylic acid [(R)-1-(6-(1,1-$d_2$)-ethoxy-pyridin-3-yl)-2-hydroxy-ethyl]-amide;
33: (1S,2S)-2-Phenyl-cyclopropanecarboxylic acid [(R)-1-(6-ethoxy-pyridin-3-yl)-2-hydroxy-ethyl]-amide;
34: (1S,2S)-2-(4-Fluoro-phenyl)-cyclopropanecarboxylic acid [(R)-1-(6-(1,1,2,2,2-$d_5$)-ethoxy-pyridin-3-yl)-2-hydroxy-ethyl]-amide;
35: (1S,2S)-2-(4-Fluoro-phenyl)-cyclopropanecarboxylic acid [(R)-1-(6-(2,2,2-$d_3$)-ethoxy-pyridin-3-yl)-2-hydroxy-ethyl]-amide;
36: (1S,2S)-2-Phenyl-cyclopropanecarboxylic acid [(R)-1-(6-(1,1-$d_2$)-ethoxy-pyridin-3-yl)-2-hydroxy-ethyl]-amide;
37: (1S,2S)-2-(4-Fluoro-phenyl)-cyclopropanecarboxylic acid [(R)-1-(6-(1,1-$d_2$)-ethoxy-pyridin-3-yl)-2-hydroxy-ethyl]-amide;
38: (1S,2S)-2-Phenyl-cyclopropanecarboxylic acid [(R)-1-(6-(1,1,2,2,2-$d_5$)-ethoxy-pyridin-3-yl)-2-hydroxy-ethyl]-amide;
39: (1S,2S)-2-(3-Fluoro-phenyl)-cyclopropanecarboxylic acid [(R)-1-(6-(2,2,2-$d_3$)-ethoxy-pyridin-3-yl)-2-hydroxy-ethyl]-amide;
40: (1S,2S)-2-Phenyl-cyclopropanecarboxylic acid [(R)-1-(6-cyclobutoxy-pyridin-3-yl)-2-hydroxy-ethyl]-amide;
41: (1S,2S)-2-(3-Fluoro-phenyl)-cyclopropanecarboxylic acid [(R)-1-(6-cyclobutoxy-pyridin-3-yl)-2-hydroxy-ethyl]-amide;
42: (1S,2S)-2-(4-Fluoro-phenyl)-cyclopropanecarboxylic acid [(R)-1-(6-cyclobutoxy-pyridin-3-yl)-2-hydroxy-ethyl]-amide;
43: (1S,2S)-2-Phenyl-cyclopropanecarboxylic ((R)-2-hydroxy-1-{6-[(R)-(tetrahydro-furan-3-yl)oxy]-pyridin-3-yl}-ethyl)-amide;
44: (1S,2S)—N-[(1R)-2-hydroxy-1-[6-[(3S)-tetrahydrofuran-3-yl]oxy-3-pyridyl]ethyl]-2-phenyl-cyclopropanecarboxamide;
45: (1S,2S)-2-((Z)-1-Methylene-penta-2,4-dienyl-cyclopropanecarboxylic acid {(R)-2-hydroxy-1-[(6-(tetrahydro-pyran-4-yloxy)-pyridin-3-yl]-ethyl}-amide;
46: (1S,2S)-2-Phenyl-cyclopropanecarboxylic acid [(R)-1-(6-ethoxy-pyridin-3-yl)-2-methoxy-ethyl]-amide;
47: (1S,2S)—N-[(1R)-2-methoxy-1-[6-[(3R)-tetrahydrofuran-3-yl]oxy-3-pyridyl]ethyl]-2-phenyl-cyclopropanecarboxamide;
48: (1S,2S)—N-[(1R)-2-methoxy-1-[6-[(3S)-tetrahydrofuran-3-yl]oxy-3-pyridyl]ethyl]-2-phenyl-cyclopropanecarboxamide;
49: (1S,2S)-2-Phenyl-cyclopropanecarboxylic acid {(R)-2-methoxy-1-[6-(tetrahydro-pyran-4-yloxy)-pyridin-3-yl]-ethyl}-amide;
50: (1S,2S)-2-Phenyl-cyclopropanecarboxylic acid {(S)-1-[6-(oxetan-3-yloxy)-pyridin-3-yl]-ethyl}-amide;
51: (1S,2S)-2-Phenyl-cyclopropanecarboxylic acid [(S)-1-(6-ethanesulfonyl-pyridin-3-yl)-ethyl]-amide;
52: (1S,2S)-2-Phenyl-cyclopropanecarboxylic acid [(R)-1-(5-ethoxy-pyridin-2-yl)-2-hydroxy-ethyl]-amide;
and pharmaceutically acceptable salts of any of these compounds.

E33. A compound according to any of embodiments 1-32, for use as a medicament.

E34. A compound according to any of embodiments 1-32, for use in therapy.

E35. A compound according to any of embodiments 1-32, for use in the treatment of a disease or disorder selected from Psychosis; Schizophrenia; cognitive disorders; cognitive impairment associated with schizophrenia; Attention Deficit Hyperactivity Disorder (ADHD); autism spectrum disorders, Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's Disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain.

E36. The compound according to embodiment 35, wherein said a disease or disorder is selected from schizophrenia; AD; ADHD; autism spectrum disorders; PD; amyotrophic lateral sclerosis; Huntington's disease; dementia associated with Lewy bodies and pain.

E37. The compound according to embodiment 36, wherein said disease or disorder is selected from schizophrenia; AD; ADHD and autism spectrum disorders.

E38. The compound according to embodiment 37, wherein said disease or disorder is selected from negative and/or cognitive symptoms of schizophrenia.

E39. The compound according to any of embodiments 1-32, for use concomitantly or sequentially with a therapeutically effective amount of a compound selected from the list consisting of acetylcholinesterase inhibitors; glutamate receptor antagonists; dopamine transport inhibitors; noradrenaline transport inhibitors; D2 antagonists; D2 partial agonists; PDE10 antagonists; 5-HT2A antagonists; 5-HT6 antagonists; KCNQ antagonists; lithium; sodium channel blockers and GABA signaling enhancers in the treatment of a disease or disorder according to any of embodiments 35-38.

E40. A pharmaceutical composition comprising a compound according to any of embodiments 1-32, and one or more pharmaceutically acceptable carrier or excipient.

E41. The composition according to embodiment 40, which composition additionally comprises a second compound selected from the list consisting of acetylcholinesterase inhibitors; glutamate receptor antagonists; dopamine transport inhibitors; noradrenaline transport inhibitors; D2 antagonists; D2 partial agonists; PDE10 antagonists; 5-HT2A antagonists; 5-HT6 antagonists; KCNQ antagonists; lithium; sodium channel blockers and GABA signaling enhancers.

E42. The composition according to embodiment 41, wherein said second compound is an acetylcholinesterase inhibitor.

E43. A kit comprising a compound according to any of embodiments 1-32, together with a second compound selected from the list consisting of acetylcholinesterase inhibitors; glutamate receptor antagonists; dopamine transport inhibitors; noradrenaline transport inhibitors; D2 antagonists; D2 partial agonists; PDE10 antagonists: 5-HT2A antagonists; 5-HT6 antagonists; KCNQ antagonists; lithium; sodium channel blockers and GABA signaling enhancers.

E44. The kit according to embodiment 43, wherein said second compound is an acetylcholinesterase inhibitor.

E45. A method for the treatment of a disease or disorder selected from Psychosis; Schizophrenia; cognitive disorders; cognitive impairment associated with schizophrenia; Attention Deficit Hyperactivity Disorder (ADHD); autism spectrum disorders, Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's Disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain, which method comprises the administration of a therapeutically effective amount of a compound according to any of embodiments 1-32 to a patient in need thereof.

E46. The method according to embodiment 45, wherein said disease or disorder is selected from schizophrenia; AD; ADHD; autism spectrum disorders; PD; amyotrophic lateral sclerosis; Huntington's disease; dementia associated with Lewy bodies and pain.

E47. The method according to embodiment 46, wherein said disease or disorder is selected from schizophrenia; AD; ADHD and autism spectrum disorders.

E48. The method according to embodiment 47, wherein said treatment comprises the treatment of negative and/or cognitive symptoms of schizophrenia.

E49. The method according to any of embodiments 45-48, wherein said treatment further comprises the administration of a therapeutically effective amount of a second compound selected from the list consisting of acetylcholinesterase inhibitors; glutamate receptor antagonists; dopamine transport inhibitors; noradrenaline transport inhibitors; D2 antagonists; D2 partial agonists; PDE10 antagonists; 5-HT2A antagonists; 5-HT6 antagonists; KCNQ antagonists; lithium; sodium channel blockers and GABA signaling enhancers.

E50. The method according to embodiment 49, wherein said second compound is an acetylcholinesterase inhibitor.

E51. Use of a compound according to any of embodiments 1-32, for the manufacture of a medicament for the treatment of a disease of disorder selected from Psychosis; Schizophrenia; cognitive disorders; cognitive impairment associated with schizophrenia; Attention Deficit Hyperactivity Disorder (ADHD); autism spectrum disorders, Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's Disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain.

E52. The use according to embodiment 51, wherein said disease or disorder is selected from schizophrenia; AD; ADHD; autism spectrum disorders; PD; amyotrophic lateral sclerosis; Huntington's disease; dementia associated with Lewy bodies and pain.

E53. The use according to embodiment 52, wherein said disease or disorder is selected from schizophrenia; AD; ADHD and autism spectrum disorders.

E54. The use according to embodiment 53, wherein said disease is the positive, negative and/or cognitive symptoms of schizophrenia.

E55. The use according to any of embodiments 51-54, wherein said manufacture further comprises the use of a second compound selected from the list consisting of acetylcholinesterase inhibitors; glutamate receptor antagonists;

dopamine transport inhibitors; noradrenaline transport inhibitors; D2 antagonists; D2 partial agonists; PDE10 antagonists: 5-HT2A antagonists; 5-HT6 antagonists: KCNQ antagonists; lithium; sodium channel blockers and GABA signaling enhancers.

E56. The use according to embodiment 55, wherein said second compound is an acetylcholinesterase inhibitor.

The compounds of the invention may exist in unsolvated as well as in solvated forms in which the solvent molecules are selected from pharmaceutically acceptable solvents such as water, ethanol and the like. In general, such solvated forms are considered equivalent to the unsolvated forms for the purposes of this invention.

Included in this invention are also isotopically labeled compounds, which are identical to those claimed in formula [I], wherein one or more atoms are represented by an atom of the same element having an atomic mass or mass number different from the atomic mass or mass number usually found in nature (e.g., $^2$H, $^3$H, $^{11}$C, $^{13}$C, $^{15}$N, $^{18}$F and the like). Particular mention is made of $^2$H substituted compounds i.e. compounds wherein one or more H atoms are represented by deuterium. In one embodiment of the invention one or more of the hydrogen atoms of the compound of formula [I] are represented by deuterium. It is recognized that elements are present in natural isotopic abundances in most synthetic compounds, and result in inherent incorporation of deuterium. However, the natural isotopic abundance of hydrogen isotopes such as deuterium is immaterial (about 0.015%) relative to the degree of stable isotopic substitution of compounds indicated herein. Thus, as used herein, designation of an atom as deuterium at a position indicates that the abundance of deuterium is significantly greater than the natural abundance of deuterium. Any atom not designated as a particular isotope is intended to represent any stable isotope of that atom, as will be apparent to the ordinarily skilled artisan.

In one embodiment, designation of a position as "D" in a compound has a minimum deuterium incorporation of greater than about 60% at that position such as greater than about 70% at that position such as greater than about 80% at that position such as greater than about 85% at that position. In a further embodiment, designation of a position as "D" in a compound has a minimum deuterium incorporation of greater than about 90% at that position such as greater than about 95% at that position such as greater than about 97% at that position such as greater than about 99% at that position.

The compounds of the present invention have three asymmetric centers with fixed stereochemistry indicated by the arrows below.

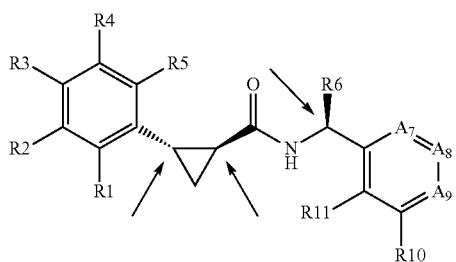

The compounds of the present invention can be manufactured from two chiral intermediates with one and two asymmetric centers, respectively, as illustrated by the examples below.

In this context is understood that when specifying the enantiomeric form of the intermediate; then the intermediate is in enantiomeric excess, e.g. essentially in a pure, mono-enantiomeric form. Accordingly, the resulting compounds of the invention are having a diastereomeric excess of at least 80%. One embodiment of the invention relates to a compound of the invention having a diastereomeric excess of at least 80% such as at least 85%, such as at least 90%, preferably at least 95% or at least 97% with reference to the three assymetric centers indicated above.

Dependent on the individually substituents R1-R14, the compounds of the present invention may furthermore have one or more additional asymmetric centers. It is intended that any optical isomers (i.e. enantiomers or diastereomers), in the form of separated, pure or partially purified optical isomers and any mixtures thereof including racemic mixtures, i.e. a mixture of stereoisomers, which have emerged because of asymmetric centers in any of substituents R1-R14, are included within the scope of the invention.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co. Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include suppositories, sprays, ointments, cremes, gels, inhalants, dermal patches, implants, etc.

In one embodiment, the compound of the present invention is adminstered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention pre to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

The compounds of formula I may be prepared by methods described below, together with synthetic methods known in the art of organic chemistry, or modifications that are familiar to those of ordinary skill in the art. The starting materials used herein are available commercially or may be prepared by routine methods known in the art, such as those method described in standard reference books such as "Compendium of Organic Synthetic Methods, Vol. I-XII" (published with Wiley-Interscience). Preferred methods include, but are not limited to, those described below.

The schemes are representative of methods useful in synthesizing the compounds of the present invention. They are not to constrain the scope of the invention in any way.

Methods of Preparation of the Compounds of the Invention.

The compounds of the invention with formula I can be prepared from intermediate III and II as described in Scheme 1.

Scheme 1

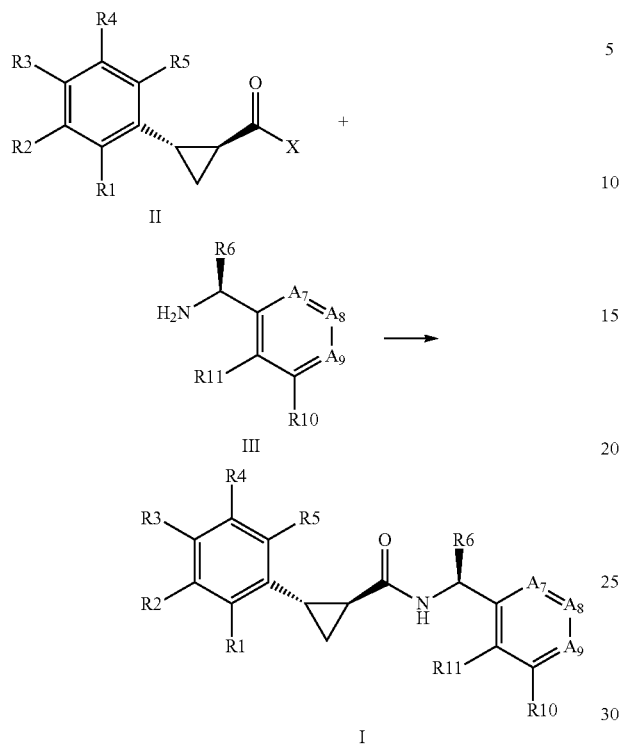

Scheme 2. Preparation of the (1S, 2S) enantiomer of formula II.

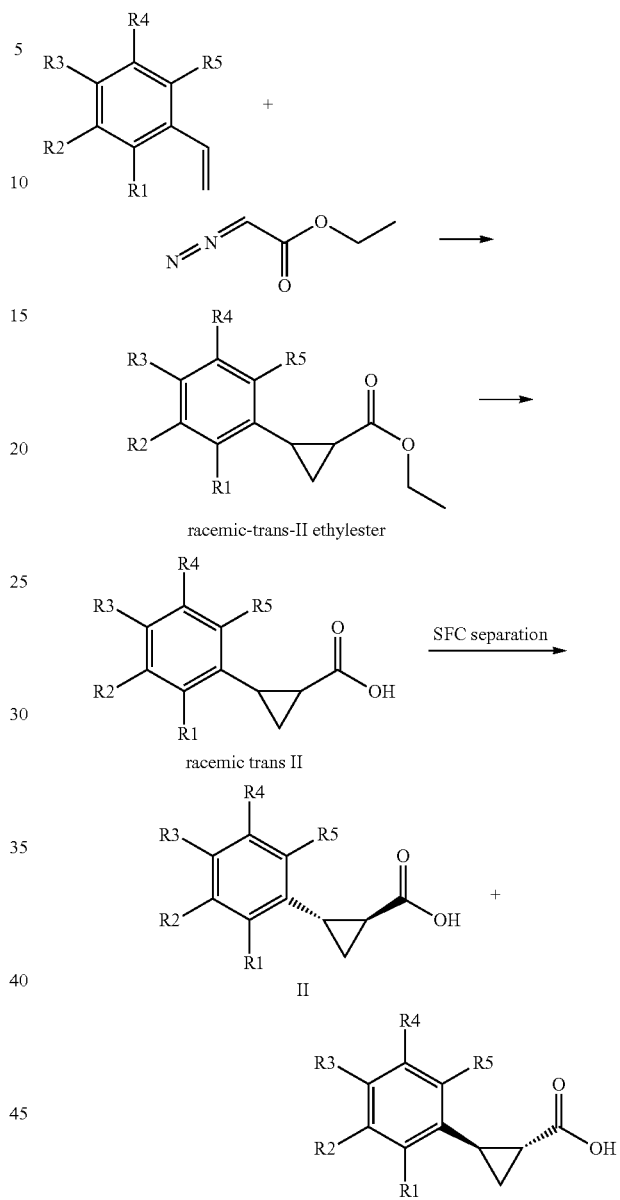

If X is a hydroxyl, the carboxylic acid II and the amine III can be condensed to form the amide I using standard peptide coupling chemistry, e.g. as described in the textbook *Synthetic Peptides A user's Guide* (Edited by Gregory A. Grant, W. H. Freeman and company (1992) ISBN 0-7167-7009-1) or as described in the textbook *Houben-Weyl Volume E22a Synthesis of peptides* (George Thiemes Verlag Stuttgart (2003) 4$^{th}$ ed.). One example of this amide formation is the use of the coupling reagent HATU (O-(benzotriazol-1-yl)-N,N,N',N'-tetramethyluronium hexafluorophosphate). Typically, one eq. of II is reacted with one eq. of HATU in the presence of two eq. of a tertiary amine e.g. triethylamine in a suitable solvent e.g. DMF. After a short period of time (e.g. five minutes) this mixture is reacted with one eq. of III to form I. Another example of this amide formation uses 1-hydroxybenzotriazole together with the water soluble carbodiimide EDC (CAS 25952-53-8) and triethyl amine in a suitable solvent e.g. THF. These reactions are usually performed at room temperature or between 0° C. and 50° C.

If X is a chloride (e.g. prepared from the carboxylic acid II, X=OH, using thionyl chloride) III can be reacted with II to form I in the presence of a tertiary amine in a suitable solvent. Alternatively, the carboxylic acid chloride (II, X=Cl) can be reacted with N-hydroxy succinimide to produce the HOSU ester which can be isolated and then reacted with III to produce I.

Methods of Preparation of the Intermediates of the Invention.

The Intermediates of the invention with formula II are either commercially available or can be prepared as described in Scheme 2.

Ethyldiazoacetate can be reacted with the styrene in Scheme II to produce the racemic-trans II ethyl ester. This ester can then be hydrolyzed to racemic trans II which can then be separated into the two enantiomers using SFC. Alternatively, racemic trans II can be resolved into the two enantiomers by known methods as described in the textbook "Enantiomers. Racemates and Resolutions" (J. Jaques, et al., John Wiley and sons, New York (1981)).

Another preparation of the compounds with formula II is described in Scheme 3. This method has been described in detail in WO2012/037258

Scheme 3. Preparation of the (1S, 2S) enantiomer of formula II.

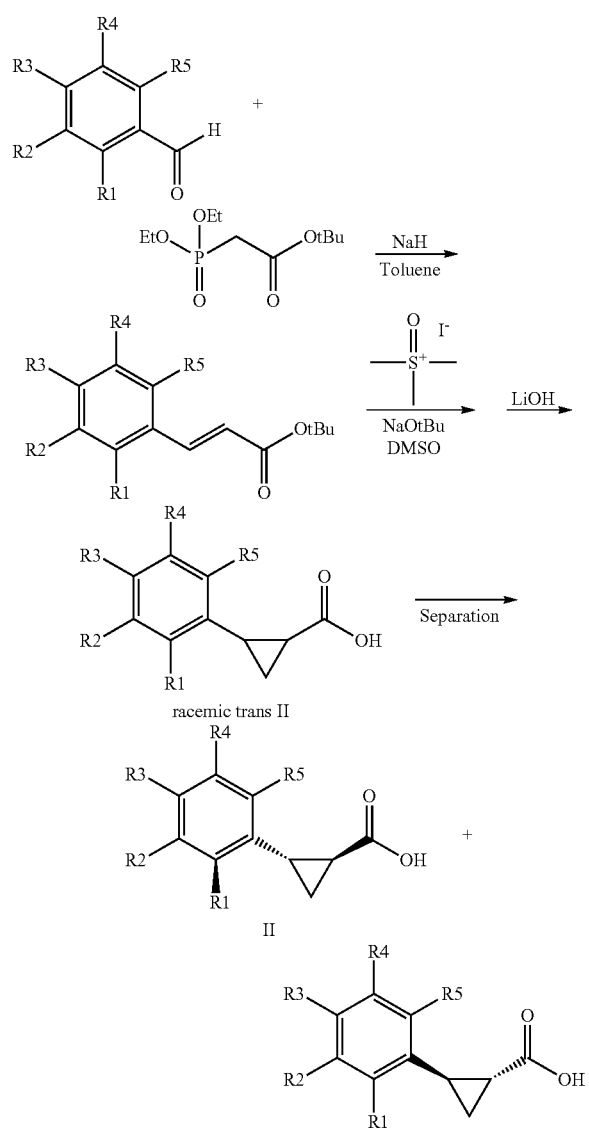

The benzaldehyde shown in Scheme 3 can be reacted with the anion of (Diethoxyphosphoryl)-acetic acid tert-butyl ester to produce the unsaturated ester shown. Cylopropanation followed by hydrolysis then produces Racemic trans II, which can be separated as described above.

The Intermediates of the invention with formula III are either commercially available or can be prepared as described in Scheme 4 in which $R_6$ is $CH_2OH$.

Scheme 4. Preparation of the chiral amines of formula III, with $R_6$ = $CH_2OH$. The method is described in: Barrow, J. C. et al. Tetrahedron Letters (2001) 2051.

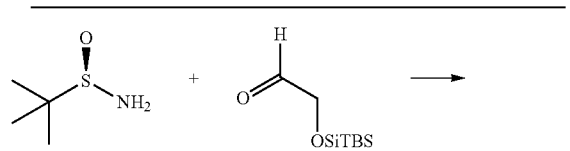

-continued

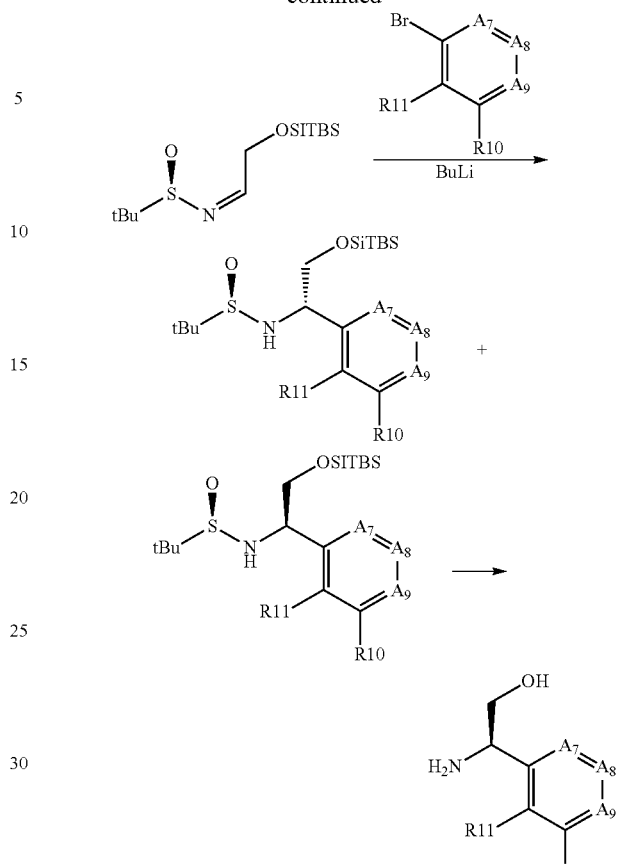

(R)-(+)-2-methyl-2-propanesulfinamide can be reacted with (tert-butyldimethylsilyloxy)acetaldehyde as described in the literature (Barrow, J. C. et al. Tetrahedron Letters (2001) 2051) to produce the sulfinimine shown in Scheme 4. 1,2-addition of an organometallic (e.g. a Grignard reagent or an aryllithiumreagent (shown in Scheme 4) reagent to this sulfinyl imines then gives the two diastereomeric protected amino alcohols shown in scheme 4. These isomers can be separated e.g. by silica gel chromatography and the protecting groups are then removed under acidic conditions.

Another method using enantiopure tert-butanesulfinamide is shown in Scheme 5 (Robak, M., Herbage, M., Ellman, Chem. Rev. 2010, 110, 3600-3740 and references cited herein). For simplicity, the method is only illustrated for $R_6$=$CH_3$, but the method is not limited to $R_6$=$CH_3$.

Scheme 5. Preparation of the chiral amines of formula III, with $R_6$ = $CH_3$. The method is described in: Robak, M., Herbage, M., Ellman, Chem. Rev. 2010, 110, 3600-3740 and references cited herein.

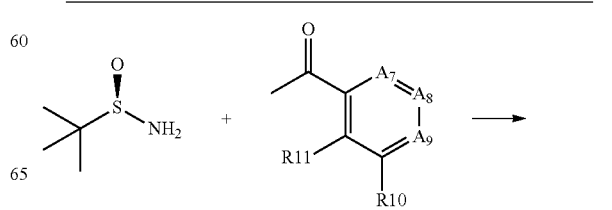

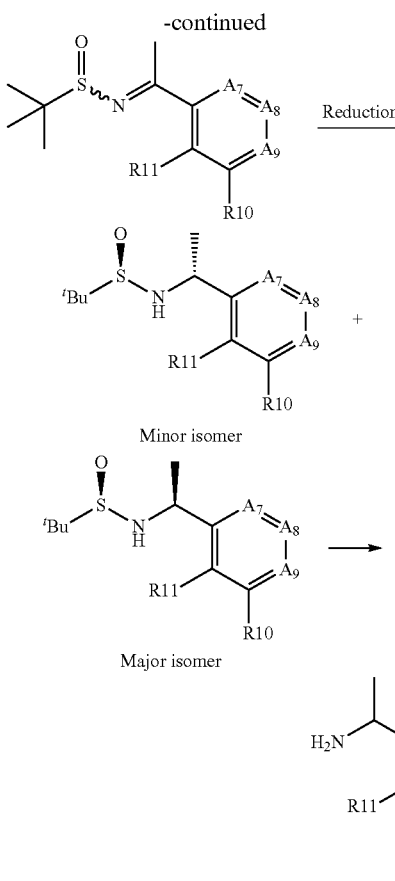

Minor isomer

Major isomer

III (R)-(+)-2-methyl-2-propanesulfinamide can be reacted with a suitable ketone and titanium(IV)ethoxide In a suitable solvent e.g. THF under heating conditions to produce the sulfinyl imine shown in scheme 5. This imine can be reduced, with some selectivity using a reducing agent (e.g. L-selectride) in a suitable solvent (e.g. THF) at a suitable temperature (e.g. −70° C.) to produce the major and the minor isomer shown in Scheme 5. The major isomer can be isolated by e.g. silica gel chromatography and the chiral auxiliary can then be removed with acid (e.g. HCl in water to produce III).

EXAMPLES

The invention will be illustrated by the following non-limiting examples.

Abbreviations

AcOH=acetic acid. $\alpha_D$=specific optical rotation. Aq=Aqueous. $BBr_3$=boron tribromide (used as DCM solution; Aldrich 17,893-4). $Boc_2O$=Boc anhydride/di-t-butyl dicarbonate (e.g. Aldrich 19,913-3). Brine=saturated aqueous solution of sodium chloride. $CDCl_3$ deuterated chloroform (e.g. Aldrich 225789). Celite=filter-aid. $CH_3I$=methyl iodide/iodomethane (e.g. Aldrich 28,956-6). $Cs_2CO_3$=cesium carbonate (Aldrich 441902). DCM=dichloromethane. DMF=dimethyl formamide. DMSO=dimethyl sulfoxide. $d_6$-DMSO=deutorated dimethyl sulfoxide (e.g. Aldrich 296147). ELSD=evaporative light scattering detection. $Et_3N$=triethyl amine. EtOAc=ethyl acetate. 99% EtOH=absolute ethanol. $Et_2O$=diethyl ether. h=hours. HATU=O-(7-Azabenzotriazol-1-yl)-N,N,N',N'-tetramethyluronium hexaflourophosphate. HBTU=2-(1H-Benzotriazol-1-yl)-1,1,3,3-tetramethyluronium hexafluorophosphate. i=iso. $K_2CO_3$=potassium carbonate (e.g. Aldrich 20,961-9). LDA=lithium di-i-propylamide (used as a THF/heptane/ethylbenzene solution; Fluka 62491). LC/MS=high-performance liquid chromatography/mass spectrometer. LAH=lithium aluminium hydride (used as a 1M THF solution; Aldrich 21,277-6). MeOH=methanol. min=minutes. $NaCNBH_3$=sodium cyanoborohydride (Aldrich 15,615-9). NaH=sodium hydride (used as a 60% dispersion; Aldrich 45,291-2). NaOH=aqueous solution of sodium hydroxide. Pd/C=palladium-on-charcoal (e.g. Aldrich 20,569-9). PTSA=para-toluene sulfonic acid hydrate (e.g. Aldrich 40,288-5). rt=room temperature. RT=retention time. sat. $NaHCO_3$=saturated aqueous solution of sodium hydrogen carbonate. sat. $NH_4Cl$=Saturated aqueous solution of ammonium chloride. SFC=supercritical flash chromatography. TFA=trifluoroacetic acid. THF=tetrahydrofuran (dried over 4 Å molecular sieves). TLC=thin layer chromatography.

Chemical names were obtained using the software MDL ISIS/DRAW 2.5 from MDL information systems Spectroscopic Methods.

Method A:

LC-MS were run on a Sciex API150EX equipped with APPI-source operating in positive ion mode. The HPLC consisted of Shimadzu LC10-ADvp LC pumps, SPD-M20A PDA detector (operating at 254 nm) and SCL-10A system controller. Autosampler was Gilson 215, Column oven was a Jones Chromatography 7990R and ELS detector was a Sedere Sedex 85.

LC-conditions: The column was a Waters Symmetry C-18, 4.6×30 mm, 3.5 μm operating at 60° C. with 3.0 mL/min of a binary gradient consisting of water+0.05% TFA (A) and methanol+0.05% TFA (B).

Gradient:

| | |
|---|---|
| 0.01 min | 17% B |
| 0.27 min | 28% B |
| 0.53 min | 39% B |
| 0.80 min | 50% B |
| 1.07 min | 59% B |
| 1.34 min | 68% B |
| 1.60 min | 78% B |
| 1.87 min | 86% B |
| 2.14 min | 93% B |
| 2.38 min | 100% B |
| 2.40 min | 17% B |
| 2.80 min | 17% B |

Total run time: 2.8 min.
The retention times ($t_R$) are expressed in minutes based on UV-trace at 254 nm.

Method B:

LC-MS were run on Waters Acquity UPLC-MS consisting of Waters Acquity including column mamager, binary solvent manager, sample organizer, PDA detector (operating at 254 nM). ELS detector, and SQD-MS equipped with APPI-source operating in positive ion mode.

LC-conditions: The column was Acquity UPLC BEH C18 1.7 μm; 2.1×50 mm operating at 60° C. with 1.2 ml/min of a binary gradient consisting of water+0.05% trifluroacetic acid (A) and acetonitrile+5% water+0.035% trifluoroacetic acid. (B)

Gradient:

| | |
|---|---|
| 0.00 min | 10% B |
| 1.00 min | 100% B |
| 1.01 min | 10% B |
| 1.15 min | 10% B |

Total run time: 12 min.

The retention times ($t_R$) are expressed in minutes based on UV-trace at 254 nm.

Method C:

Preparative supercritical fluid chromatography (SFC) was performed on a Berger Multigram II operating at 50 mL/min at 35° C. and 100 bar backpressure using stacked injections. The column was a ChiralpakAD 5 u, 250×21 mm. The eluent was $CO_2$ (70%) and ethanol (30%).

Method D:

Preparative supercritical fluid chromatography (SFC) was performed on a Thar SFC-80 operating at 60 g/min at 35° C. and 140 bar backpressure using stacked injections. The column was a ChiralPakAD-H (250×30 mm). The eluent was $CO_2$ (88%) and Ethanol (12%).

Method E:

Preparative supercritical fluid chromatography (SFC) was performed on a Thar SFC-200 operating at 100 g/min at 35° C. and 140 bar backpressure using stacked injections. The column was a ChiralPakAD-H (250×30 mm). The eluent was $CO_2$ (90%) and Ethanol (10%).

Method F:

Enantiomeric excess (ee) was determined on an Aurora Fusion A5 SFC system operating at 3 ml/min at 40° C. and 100 bar backpressure. The column was a Chiralpak AD (150×4.6 mm). The eluent was $CO_2$ (70%) and ethanol+0.1% diethyl amine (30%).

$^1$H NMR spectra were recorded at 500.13 MHz on a Bruker Avance DRX-500 instrument at T=303.3 K or at 600 MHz on a Bruker Avance AV-III-600 instrument. Chemical shift values are expressed in ppm-values relative to tetramethylsilane unless noted otherwise. The following abbreviations or their combinations are used or multiplicity of NMR signals: s=singlet, d=doublet, m=multiplet and br=broad.

Preparation of Intermediates

Preparation of Bromopyridines.

IM1: 5-Bromo-2-isopropoxy-pyridine

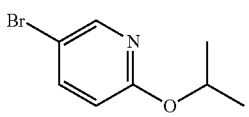

60% NaH in oil (1.5:1, Sodium hydride:Mineral Oil, 5.20 g) was added in two portions to isopropyl alcohol (150 mL) at room temperature under $N_2$. The mixture was stirred at 60° C. for 30 min. 5-bromo-2-chloropyridine (10.00 g, 51.96 mmol) was added in two portions and the mixture was stirred at reflux 4 h and than at 80° C. overnight. The solution was concentrated in vacuo. Water (50 mL) and EtOAc (50 mL) was added and the layers were separated. The aqueous layer was extracted with EtOAc (50 mL). The combined organic layers were washed with brine, dried over $MgSO_4$, filtered and the solvent was removed in vacuo. The crude product was subjected to flash chromatography (silica, 0-50% EtOAc in heptanes) to give the title compound as a clear oil (8.74 g, 78%). $^1$H NMR (600 MHz, DMSO) δ 8.17 (s, 1H), 7.61 (dd, 1H), 6.59 (d, 1H), 5.23 (m, 1H), 1.33 (s, 6H).

IM2: 5-Bromo-2-(2,2,2-trifluoro-ethoxy)-pyridine

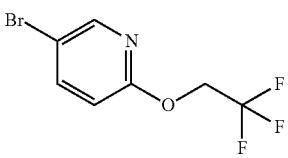 [SMILES: FC(F)(F)COc1ccc(Br)cn1]

Prepared analogously to IM1 to give the title compound as a colorless liquid (2.78 g, 54%) sufficiently pure for the next step.

IM3: 5-Bromo-2-propoxy-pyridine

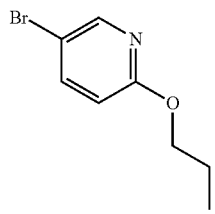

Potassium tert-butoxide (1.85 g, 16.5 mmol) was added to a mixture of 5-bromo-2-chloropyridine (2.89 g, 15.0 mmol) and 1-propanol (1.230 mL, 16.5 mmol) in THF (15 mL). The reaction mixture was heated at 120° C. for 30 minutes in a microwave reactor. The mixture was poured into a mixture of water (50 mL) and EtOAc (100 mL). The organic layer was washed with brine, dried over $MgSO_4$ and evaporated to dryness. Flash chromatography (silica, 0-20% EtOAc in heptanes) gave the title compound as a yellow oil (3.13 g, 97%) sufficiently pure for the next step.

IM4: 5-Bromo-2-(2,2,2-$d_3$)-ethoxy-pyridine

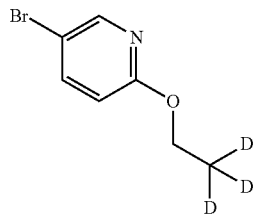 [SMILES: [2H]C([2H])([2H])COc1ccc(Br)cn1]

Prepared analogously to IM3 using commercially available 2,2,2-$d_3$-ethanol (Sigma-Aldrich, catalog no 329347) to give the title compound as a colorless oil (2.53 g, 82%) sufficiently pure for the next step.

IM5: 5-Bromo-2-(1,1,2,2,2-d₅)-ethoxy-pyridine

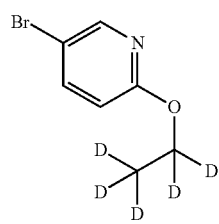 [SMILES: [2H]C([2H])([2H])C([2H])([2H])Oc1ccc(Br)cn1]

Prepared analogously to IM3 using commercially available 1,1,2,2,2-d₅-ethanol (Sigma-Aldrich, catalog no 489338) to give the title compound as a colorless oil (1.16 g, 87%) sufficiently pure for the next step.

IM6: 5-Bromo-2-(1,1-d₂)-ethoxy-pyridine

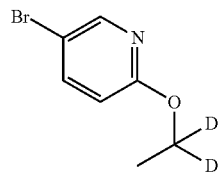

Prepared analogously to IM3 using commercially available 1,1-d₂-ethanol (Sigma-Aldrich, catalog no 347434) to give the title compound as a colorless oil (2.61 g, 85%) sufficiently pure for the next step.

IM7: 5-Bromo-2-(2-methoxy-ethoxy)-pyridine

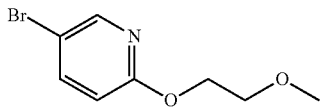

2-Methoxyethanol (5.12 mL, 85.0 mmol) was dissolved in 1,4-dioxane (125 ml). Potassium tert-butoxide (7.00 g, 62.4 mmol) was added under $N_2$. The mixture was stirred for 10 minutes. 5-Bromo-2-chloropyridine (10.0 g, 52.0 mmol) was added and the resulting mixture was refluxed for 2 hours. The mixture was poured into brine and extracted with EtOAc. The organic layer was washed with brine, dried over $MgSO_4$ and evaporated to dryness. Purification by flash chromatography (silica, heptanes/EtOAc 4:1) gave the title compound as a colorless oil (8.74 g, 73%) sufficiently pure for the next step.

IM8: 5-Bromo-2-methoxymethyl-pyridine

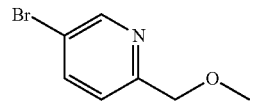

To a solution of 5-bromopyridine-2-carbaldehyde (5.00 g, 26.9 mmol) dissolved in a mixture of ethanol (75 mL) and THF (25 mL) was added sodium borohydride (0.407 g, 10.8 mmol) in small portions. After 45 minutes 0.5 mL water was added and the mixture and evaporated to dryness. The oily residue was subjected to flash chromatography (silica, EtOAc/EtOH/Et3N 90:5:5) to give (5-bromo-pyridin-2-yl)-methanol (4.81 g, 86%) as pale-yellow oil.

A solution of this (5-bromo-pyridin-2-yl)-methanol (4.80 g, 23.0 mmol) in DMF (25 mL) was added drop wise over 5 minutes to a slurry of sodium hydride (1.10 g, 27.8 mmol) in DMF (50 mL) at 0° C. under $N_3$. The mixture was stirred for 15 minutes before the drop wise addition of a solution of methyl iodide (1.57 mL, 25.3 mmol) in DMF (25 mL). The mixture was allowed to reach room temperature and was then stirred overnight. The mixture was poured into brine and extracted with EtOAc. The combined organic layers were thoroughly washed with brine, dried over $MgSO_4$ and evaporated to dryness to give the title compound as a yellow oil (4.77 g, 98%) sufficiently pure for the next step.

IM9: 5-Bromo-2-cyclobutoxy-pyridine

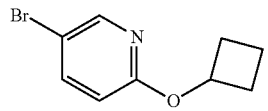

Prepared analogously to IM3 using commercially available cyclobutanol to give the title compound as a clear oil (2.72 g, 80%) sufficiently pure for the next step.

IM10: 5-Bromo-2-[(R)-(tetrahydrofuran-3-yl)oxy]-pyridine

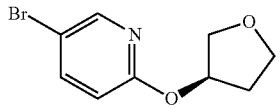 [SMILES: Brc1ccc(O[C@@H]2CCOC2)nc1]

To a solution of 5-bromo-2-chloropyridine (10 g, 52.1 mmol) in 100 mL of DMF was added commercially available (R)-(−)-3-hydroxytetrahydrofuran (6.87 g, 78.1 mmol) and $Cs_2CO_3$ (33.85 g, 0.104 mol), the resulting mixture was heated 90° C. for 36 hours. The solvent was concentrated and the residue was extracted with EtOAc (500 ml), washed with water (200 ml). The organic layer was dried over $Na_2SO_4$, concentrated and purified by chromatography on silica gel (eluting with Petrol ether: EtOAc=100:1) to afford 5-Bromo-2-[(R)-(tetrahydro-furan-3-yl)oxy]-pyridine (5.9 g, yield:

47%) as a solid. ¹HNMR (CDCl₃ 400 MHz): δ8.15 (d, J=2.4 Hz, 1H), 7.61-7.64 (m, 1H), 6.64 (d, J=8.8 Hz, 1H), 5.47-5.50 (m, 1H), 3.85-4.02 (m, 4H), 2.07-2.28 (m, 2H), $[\alpha]_D^{20}$=+18.5 (C=0.189, CHCl₃).

IM11: 5-Bromo-2-[(S)-(tetrahydro-furan-3-yl)oxy]-pyridine

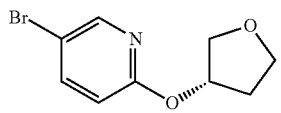 [SMILES: Brc1ccc(O[C@H]2CCOC2)nc1]

Prepared analogously to IM10 using commercially available (S)-(+)-3-hydroxytetrahydrofuran to afford 5-Bromo-2-[(S)-(tetrahydro-furan-3-yl)oxy]-pyridine
(9.62 g, yield: 51%) as a solid. ¹HNMR (CDCl₃ 400 MHz): δ8.16 (d, J=2.4 Hz, 1H), 7.62-7.65 (m, 1H), 6.64-6.66 (m, 1H), 5.48-5.52 (m, 1H), 3.99-4.03 (m, 2H), 3.86-3.97 (m, 2H), 2.20-2.29 (m, 1H), 2.08-2.15 (m, 1H). $[\alpha]_D^{20}$=20.7 (C=0.21, CHCl₃).

IM12: 5-Bromo-2-(tetrahydro-pyran-4-yloxy)-pyridine

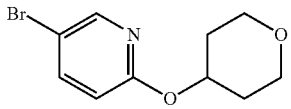 [SMILES: Brc1ccc(OC2CCOCC2)nc1]

Prepared analogously to IM3 using commercially available tetrahydro-4-pyranol to give the title compound sufficiently pure for the next step.

IM13: 6-Bromo-[1,3]dioxolo[4,5-b]pyridine

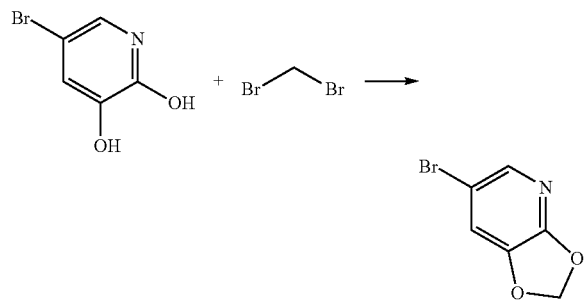

To a suspension of 5-Bromo-pyridine-2,3-diol (10.0 g, 52.63 mmol, commercially available, CAS 34206-49-0) in NMP (100 mL) was added K₂CO₃ (21.97 g, 158 mmol) and dibromo methane (10.97 g, 63.16 mmol). The reaction mixture was heated to 90° C. for 16 h. EtOAc was added and the salts were filtered off. Water was added, the phases were separated and the aq layer was extracted with more ethyl acetate. The combined organic layers was dried over anhydrous Na₂SO₄ and concentrated under vacuo to get the crude compound. The crude compound was purified by silica gel chromatography (eluent 5% ethyl acetate in petrol ether). Yield of 6-Bromo-[1,3]dioxolo[4,5-b]pyridine 2.2 g (21%) pure by ¹H NMR (400 MHz, DMSO) δ 7.71 (d, 1H, J=2 Hz), 7.55 (d, 1H, J=2 Hz), 6.20 (s, 2H). Mp 69-71 C.

IM14: 7-Bromo-2,3-dihydro-[1,4]dioxino[2,3-b]pyridine

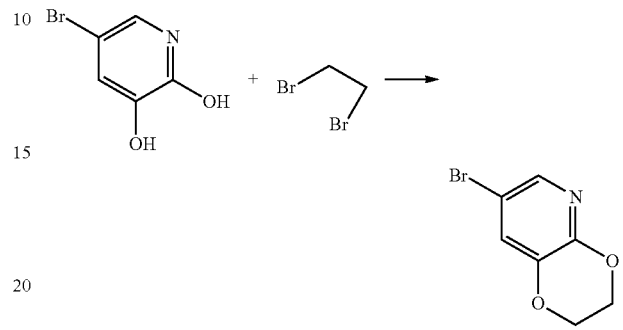

To a suspension of 5-Bromo-pyridine-2,3-diol (10.0 g, 52.63 mmol, commercially available, CAS 34206-49-0) in DMF (150 mL) was added K₂CO₃ (21.78 g, 158 mmol) and 1,2-dibromo ethane (11.87 g, 63.2 mmol). The reaction mixture was heated to 100° C. for 5 h. The reaction mixture was cooled to rt and poured into ice cold water EtOAc was added and the phases were separated and the aq layer was extracted with more ethyl acetate. The combined organic layers was dried over anhydrous Na₂SO₄ and concentrated under vacuo to get the crude compound. The crude compound was purified by silica gel chromatography (eluent 10% ethyl acetate in petrol ether). Yield of 6-Bromo-[1,3]dioxolo[4,5-b]pyridine 2.2 g (18%) pure by ¹H NMR (400 MHz, DMSO) δ 7.85 (d, 1H, J=2 Hz), 7.59 (d, 1H, J=2 Hz), 4.41 (m, 2H), 4.27 (m, 2H).

Acetylation of Pyridines.

IM15: 1-(6-Chloro-pyridin-3-yl)-ethanone

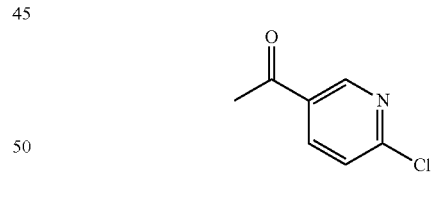

A round bottomed flask was charged with 5-bromo-2-chloropyridine (5.30 g, 27.6 mmol) in THF under N₂ and cooled at 0° C. A solution of 1 M iso-propylmagnesiumchloride-lithium chloride complex in THF (40 mL) was added drop wise over 15 min. After 70 min N-methoxy-N-methylacetamide (4.1 mL, 38 mmol) was added drop wise. After stirring for 5 min at 0° C. the cooling bath was removed. The mixture was left stirring overnight and was then quenched by the addition of 100 mL saturated aqueous NH₄Cl solution. The mixture was extracted with 3×100 mL EtOAc. The combined organic layers were washed with water followed by brine and dried over MgSO$_4$. Evaporation of the volatiles at 80° C. 10 mbar for 1 h gave the title compound (3.596 g, 84) sufficiently pure for the next step.

IM16: 1-(6-Iso-propoxy-pyridin-3-yl)-ethenone

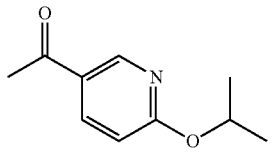

A round-bottomed flask was charged with 5-bromo-2-iso-propoxypyridine (IM1) (5.00 g, 23.1 mmol) in THF (100) under N$_2$ and cooled in an acetone/dry-ice bath to –66° C. (Internal temperature). A solution of 2.5 M n-butyllithium in hexane (10.1 mL, 25.3 mmol) was added drop wise over 10 minutes at keeping the internal temperature below –55° C. The mixture was stirred at –65° C. for 15 minutes. N-methoxy-N-methylacetamide (3.07 mL, 28.9 mmol) dissolved in THF (10 mL) was then added drop wise over 10 minutes while keeping the internal temperature below –65° C. Alter stirring for 1 h the mixture was allowed to reach room temperature. The mixture was poured into saturated aqueous NH$_4$Cl solution and extracted with EtOAc. The combined organic layers were washed with brine, dried over MgSO$_4$ and evaporated to dryness. Flash chromatography (silica, heptanes/EtOAc 4:1) gave the title compound as a colorless oil (3.20 g, 77%) sufficiently pure for the next step.

IM17: 1-(6-Methoxymethyl-pyridin-3-yl)-ethenone

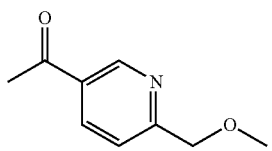

Prepared analogously to IM16 from IM8 to give the title compound as a colorless liquid (0.379 g, 17%) sufficiently pure for the next step.

IM18: 1-[6-(2,2,2-Trifluoro-ethoxy)-pyridin-3-yl]-ethenone

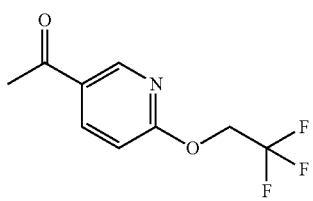

Prepared analogously to IM16 from IM2 to give the title compound as a colorless liquid (1.234 g, 48%) sufficiently pure for the next step.

IM19: 1-[6-(2-Methoxy-ethoxy)-pyridin-3-yl]-ethanone

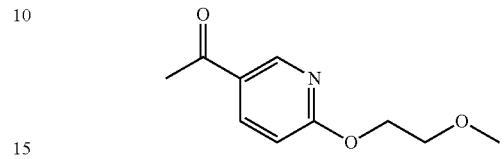

Prepared analogously to IM16 from IM7 to give the title compound as a colorless liquid (2.13 g, 57%) sufficiently pure for the next step.

IM20: 1-(2-Ethoxy-pyridin-4-yl)-ethanone

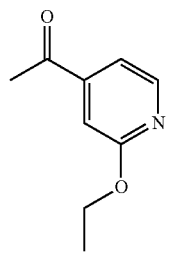

Prepared analogously to IM16 from commercially available 4-bromo-2-ethoxy-pyridine, Synchem OHG catalog no CT091 to give the title compound as a colorless liquid (1.20 g, 49%) sufficiently pure for the next step.

IM21: 1-[1,3]Dioxolo[4,5-b]pyridin-6-yl-ethanone

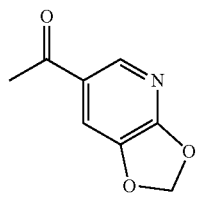

A round-bottomed flask was charged with 6-Bromo-[1,3] dioxolo[4,5-b]pyridine IM13 (1.74 g, 8.61 mmol) in DMF (25 ml) under N$_2$ and tributyl(1-ethoxyvinyl)tin (3.65 ml, 10.8 mmol) was added. Tetrakistriphenylphosphine-palladium(0) (0.50 g, 0.43 mmol) was added and the solution was stirred at 65° C. overnight. The mixture was added to water and EtOAc and the phases were separated. The org phase was washed with brine, dried (MgSO4) filtered and was rotovaped. The residue was dissolved in THF (100 ml), and a mixture of water (15 ml) and conc. HCl (2.5 ml) was added and the solution was stirred at rt 5 min. The solution was added to brine and sat NaHCO3 solution was added until the solution was slightly alkaline. The org Phase was extracted with EtOAc and the phases were separated. The org phase was washed with brine, dried (MgSO4) filtered and was rotovaped. The residue was redissolved in THF (10 ml) EtOAc (20 ml) and heptanes (20 ml). The mixture was concentrated until 25 ml remained and cooled in ice. A solid precipitated and was collected by filtration. Yield: 0.942 g (66%) of IM21. 1H-NMR (500 MHz, DMSO) δ 8.47 (s, 1H), 8.54 (s, 1H), 6.27 (s, 2H), 2.53 (s, 3H).

IM22: 1-(2,3-Dihydro-[1,4]dioxino[2,3-b]pyridin-7-yl)-ethenone

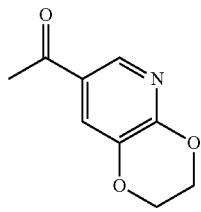

Prepared analogously to IM21 from with 7-Bromo-2,3-dihydro-[1,4]dioxino[2,3-b]pyridine (3.00 g, 13.9 mmol) to give the title compound as a white powder (1.84 g, 74%). 1H-NMR (500 MHz, DMSO) δ 8.47 (s, 1H), 8.54 (s, 1H), 6.27 (s, 2H), 2.53 (s, 3H).

IM23: 1-(6-Ethyl-pyridin-3-yl)-ethanone

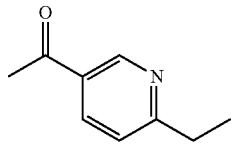

A dry round bottomed flask was charged with 1-(6-chloro-3-pyridinyl)-1-ethanone (IM15) (3.596 g, 23.11 mmol) and [1,1'-bis(diphenylphosphino)ferrocene]-dichloropalladium(II) (1.694 g, 2.315 mmol) in THF (100 mL) under $N_2$. A 1 M solution of diethyl zinc in hexane (35 mL, 35 mmol) was added drop wise to this mixture followed by N,N-dimethylaminoethanol (0.50 mL, 5.0 mmol). The mixture was heated to reflux for 30 minutes. The mixture was cooled to room temperature and then quenched by the addition of saturated aqueous $NH_4Cl$ solution (100 mL). The mixture was filtered through a plug of celite. The aqueous layer was extracted with EtOAc (3×100 mL). The combined organic layers were washed with water, brine and then dried over $Mg_2SO_4$. Flash Chromatography (120 g silica, 0-40% EtOAc in heptanes) gave the title compound as a yellow oil (0.699 g, 20%) sufficiently pure for the next step.

Preparation of Chiral Amines.

Chiral amines were made, if not commercially available, according to well-described procedure for either 1,2-stereoselective reduction of sulfinyl mines or 1,2-stereoselective addition of organometallic reagents to sulfinyl imines. These methods have been described by Chellucci, G., Baldino, S., Chessa, S., Pinna, G., Soccolini, S., *Tetrahedron Asymmetry* 2006, 17, 3163-3169, Evans, J., Ellman, J., *J. Org. Chem.* 2003, 68, 9948-9957 and Robak, M., Herbage, M., Ellman, J., *Chem. Rev.* 2010, 110, 3600-3740 and references cited herein.

IM24: (S)-1-(6-isopropoxy-pyridin-3-yl)-ethylamine

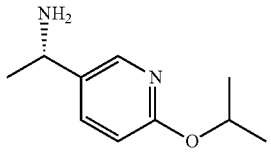

Step 1: Formation of Sulfinyl Imine:

1-(6-iso-propoxy-pyridin-3-yl)-ethanone IM16 (3.20 g, 17.8 mmol) was dissolved in THF (55 mL) under $N_2$. R(+)-2-methyl-2-propanesulfinamide (2.21 g, 18.2 mmol) and titanium(IV)ethoxide (7.40 mL, 35.7 mmol) was added. The mixture was refluxed for 24 hours. The mixture was allowed to reach room temperature. The mixture was diluted with EtOAc (200 mL) and poured into ice/brine. The resulting slurry was filtered through Celite. The organic layer was washed with brine, dried over $MgSO_4$ and evaporated to dryness. Flash chromatography (silica, heptanes/EtOAc 2:1) gave (R)-2-methyl-propane-2-sulfinic acid [1-(6-isopropoxy-pyridin-3-yl)-ethylidene]-amide (4.04 g, 80%) as a yellow oil sufficiently pure for the next step.

Step 2: Reduction of the Imine:

A round-bottomed flask was charged with (R)-2-methyl-propane-2-sulfinic acid [1(6-isopropoxy-pyridin-3-yl)-ethylidene]-amide (4.00 g, 14.2 mmol) in THF (50 mL) under $N_2$ and cooled to –66° C. (internal temperature). A 1.00 M solution of L-Selectride in THF (29.0 mL, 29.0 mmol) was added drop wise over 15 minutes. The mixture was stirred at –70° C. for 1 hour. The cold mixture was poured into saturated aqueous $NH_4Cl$ solution. The mixture was extracted with EtOAc. The combined organic layers were washed with brine, dried over $MgSO_4$ and evaporated to dryness. Flash chromatography (silica, EtOAc) gave (R)-2-methyl-propane-2-sulfinic acid [(S)-1-(6-isopropoxy-pyridin-3-yl)-ethyl]-amide (2.91 g, 72%) as a colorless powder. Diastereomeric excess >95% based on $^1H$ NMR.

Step 3: Removal of Chiral Auxiliary:

(R)-2-Methyl-propane-2-sulfinic acid [(S)-1-(6-isopropoxy-pyridin-3-yl)-ethyl]-amide (2.90 g, 10.2 mmol) was dissolved in methanol (48 mL). A mixture of 12.0 M HCl in water (4.25 mL) and water (4.25 mL) was added drop wise over 3 minutes. The mixture was stirred at room temperature overnight. The mixture was evaporated to dryness. The oily residue was subjected to flash chromatography (silica, EtOAc/EtOH/triethylamine 90:5:5) on a short column to give (S)-1-(6-isopropoxy-pyridin-3-yl)ethylamine IM24 (1.71 g, 93%) as a pale-yellow oil sufficiently pure for the next step. The overall yield from 1-(6-isopropoxy-pyridin-3-yl)-ethanone IM16 was 54%.

IM25: (S)-1-(6-Ethyl-pyridin-3-yl)-ethylamine

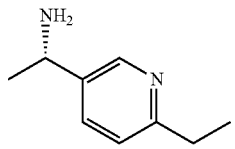

Prepared analogously to IM24 from IM23 to give the title compound sufficiently pure for the next step.

IM26: (S)-1-(6-Methoxymethyl-pyridin-3-yl)-ethylamine

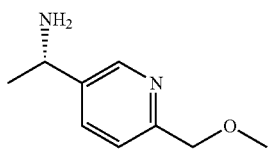

Prepared analogously to IM24 to give the title compound sufficiently pure for the next step.

IM27: (S)-1-[6-(2,2,2-Trifluoro-ethoxy)-pyridin-3-yl]-ethylamine

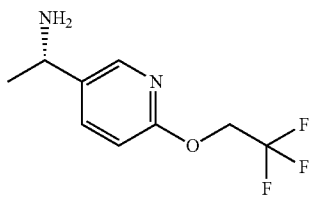

Prepared analogously to IM24 to give the title compound sufficiently pure for the next step.

IM28: (S)-1-[6-(2-Methoxy-ethoxy)-pyridin-3-yl]-ethylamine

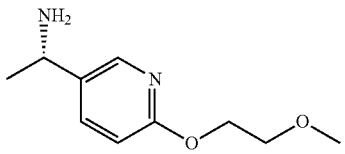

Prepared analogously to IM24 to give the title compound sufficiently pure for the next step.

IM29: (S)-1-(2-Ethoxy-pyridin-4-yl)-ethylamine

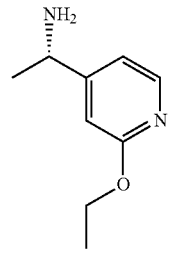

Prepared analogously to IM24 to give the title compound sufficiently pure for the next step.

IM30: (S)-1-{6-[(S)-(Tetrahydro-furan-3-yl)oxy]-pyridin-3-yl}-ethylamine

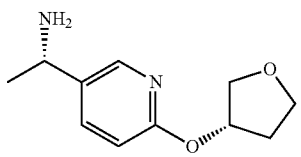

Prepared analogously to IM24 to give the title compound sufficiently pure for the next step.

IM31: (S)-1-{6-[(R)-(Tetrahydro-furan-3-yl)-oxy]-pyridin-3-yl}-ethylamine

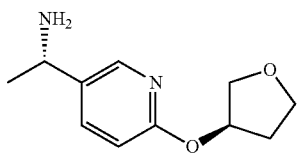

Prepared analogously to IM24 to give the title compound sufficiently pure for the next step.

IM32: (S)-1-[1,3]Dioxolo[4,5-b]pyridin-6-yl-ethylamine

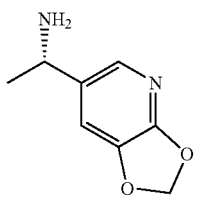

Prepared analogously to IM24 to give the title compound sufficiently pure for the next step.

IM33: (S)-(2,3-Dihydro-[1,4]dioxino[2,3-b]pyridin-7-yl)-ethylamine

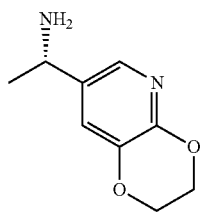

Prepared analogously to IM24 to give the title compound sufficiently pure for the next step.

IM34: (S)-1-(2-Ethoxy-pyrimidin-5-yl)-ethylamine

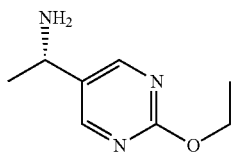

Prepared analogously to IM24 to give the title compound sufficiently pure for the next step.

IM35: 2-[5-((S)-1-Amino-ethyl)-pyridin-2-yloxy]-ethanol

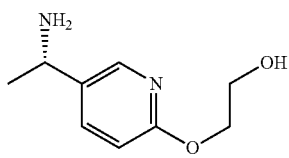

Prepared analogously to IM24 to give the title compound sufficiently pure for the next step.

IM36: (R)-2-Amino-2-(6-propoxy-pyridin-3-yl)-ethanol

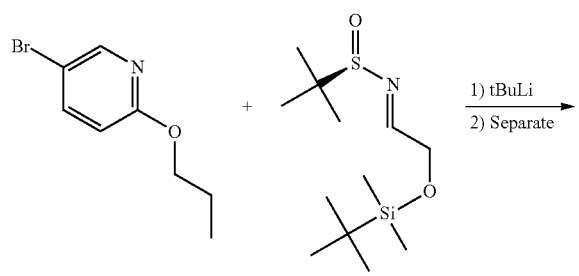

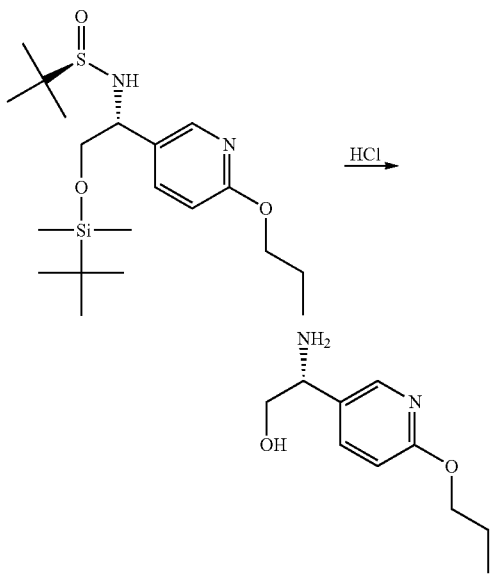

Step 1:

A 1.7 M solution of tert-butyllithium in pentane (15.2 mL, 25.8 mmol) was added drop wise to a stirring solution of 5-bromo-2-propoxypyridine IM3 (2.54 g, 11.8 mmol) dissolved in dry THF (29.4 mL) at −78° C. under Ar. The solution was subsequently stirred at this temperature for 30 min. A solution of (R)-2-methyl-propene-2-sulfinic acid [2-(tert-butyl-dimethyl-silanyloxy)-ethylidene]-amide IM49 (3.26 g, 11.8 mmol) in dry THF (15 mL) was then added drop wise at −78° C. and the solution was stirred at this temperature for 30 min. The cooling bath was removed and the mixture was allowed to reach room temperature overnight. The mixture was quenched with saturated aqueous $NH_4Cl$ solution (75 mL) and EtOAc (150 mL). The phases were separated and the organic layer was washed with brine and then dried over $MgSO_4$. Flash chromatography (silica, 10-100% EtOAc in heptanes) gave (R)-2-Methyl-propane-2-sulfinic acid [(R)-2-(tert-butyl-dimethyl-silanyloxy)-1-(6-propoxy-pyridin-3-yl)-ethyl]-amide, the fastest eluding isomer, as a clear oil (2.33 g, 48%) sufficiently pure for the next step. Diastereomeric excess >95% based on $^1$H NMR.

Step 2:

A 2.00 M solution of hydrogen chloride in diethyl ether (28 mL, 56 mmol) was added to a stirred solution of [(R)-2-(tert-butyl-dimethyl-silanyloxy)-1-(6-propoxy-pyridin-3-yl)-ethyl]-amide (2.33 g, 5.62 mmol) dissolved in MeOH (11 mL) at 0° C. under Ar. After the addition was completed the cooling bath was removed and the solution was stirred at room temperature overnight. The mixture was then evaporated to dryness and the residue was suspended in methylene chloride and transferred to a short silica gel column. After eluding with EtOAc:EtOH:$Et_3N$ (90:5:5) (R)-2-Amino-2-(6-propoxy-pyridin-3-yl)-ethanol. IM36, was obtained as an oil (0.813 g, 74%). The overall yield from 5-bromo-2-propoxy-pyridine IM3 was 36%.

¹H NMR (600 MHz, CDCl₃) δ 8.61 (s, 1H), 8.60 (dd, 1H), 7.71 (d, 1H), 4.22 (t, 2H), 4.06 (m, 1H), 3.72 (m, 1H), 3.60 (m, 1H), 1.78 (m, 2H), 1.24 (m, 1H), 1.02 (m, 4H).

IM37: (R)-2-Amino-2-(6-isopropoxy-pyridin-3-yl)-ethanol

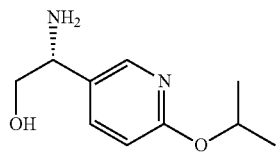

Prepared analogously to IM36 to give the title compound sufficiently pure for the next step (1.07 g, 36% overall yield from IM1).

IM38: (R)-2-Amino-2-(6-ethoxy-pyridin-3-yl)-ethanol

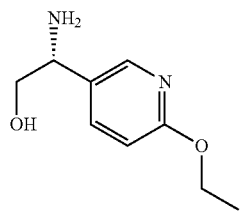

Prepared analogously to IM36 to give the title compound sufficiently pure for the next step (0.360 g, 35% overall yield from commercially available 5-bromo-2-ethoxy-pyridine, Apollo catalog no OR13065).

IM39: (R)-2-Amino-2-(6-(1,1,2,2,2-d₅)-ethoxy-pyridin-3-yl)-ethanol

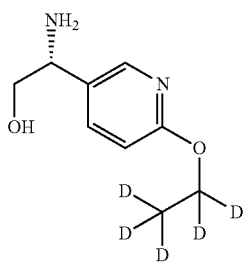 [SMILES: [2H]C([2H])([2H])C([2H])([2H])Oc1ccc([C@@H](N)CO)cn1]

Prepared analogously to IM36 to give the title compound sufficiently pure for the next step (0.500 g, 22% overall yield from IM5).

IM40: (R)-2-Amino-2-(6-(2,2,2-d₃)-ethoxy-pyridin-3-yl)-ethanol

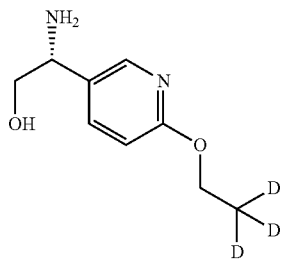 [SMILES: [2H]C([2H])([2H])COc1ccc([C@@H](N)CO)cn1]

Prepared analogously to IM36 to give the title compound sufficiently pure for the next step (0.647 g, 30% overall yield from IM4).

IM41: (R)-2-Amino-2-(6-(1,1-d₂)-ethoxy-pyridin-3-yl)-ethanol

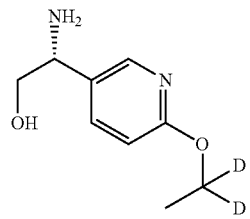

Prepared analogously to IM36 to give the title compound sufficiently pure for the next step (0.380 g, 18% overall yield from IM6).

IM42: (R)-2-Amino-2-{6-[(S)-tetrahydro-furan-3-yl)oxy]-pyridin-3-yl}-ethanol

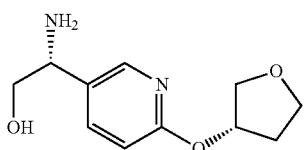

Prepared analogously to IM36 to give the title compound sufficiently pure for the next step.

IM43: (R)-2-Amino-2-{6-[(R)-(tetrahydro-furan-3-yl)oxy]-pyridin-3-yl}-ethanol

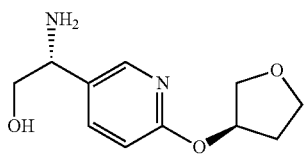 [SMILES: N[C@@H](CO)c1ccc(O[C@@H]2CCOC2)nc1]

Prepared analogously to IM36 to give the title compound sufficiently pure for the next step.

IM44: (R)-2-Amino-2-(6-cyclobutoxy-pyridin-3-yl)-ethanol

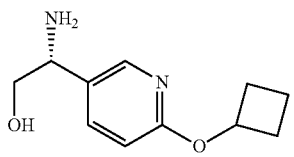 [SMILES: N[C@@H](CO)c1ccc(OC2CCC2)nc1]

Prepared analogously to IM36 to give the title compound sufficiently pure for the next step.

IM45: (R)-2-Amino-2-[6-(tetrahydro-pyran-4-yloxy)-pyridin-3-yl]-ethanol

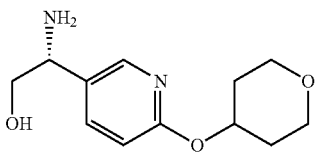 [SMILES: N[C@@H](CO)c1ccc(OC2CCOCC2)nc1]

Prepared analogously to IM36 to give the title compound sufficiently pure for the next step.
Preparation of Carboxylic Acids.

IM46: (1S,2S)-2-Phenyl-cyclopropanecarboxylic acid

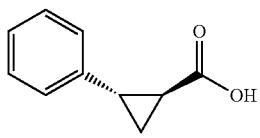 [SMILES: O=C(O)[C@H]1C[C@@H]1c1ccccc1]

Commercially available, racemic trans 2-phenyl-cyclopropanecarboxylic acid (Sigma-Aldrich, catalog no P22354) was subjected to chiral SFC separation, method C to give IM46 as an oil that slowly solidified upon standing. Enantiomeric purity 95% ee (Method F). Specific optical rotation +300.9° $[\alpha]_D^{20}$ (C=1% EtOH). (Lit: +389° $[\alpha]_D^{20}$ (C=0.61, CHCl$_3$) Kozikowski et al., *J. Med. Chem.* 2009, 52, 1885-1902). (Lit: +311.7° $[\alpha]_D^{20}$ (C=1.776, EtOH) Walboruky et al., *Tetrahedron* 1964, 20, 1695-1699.)

IM47: (1S,2S)-2-(3-Fluoro-phenyl)-cyclopropanecarboxylic acid

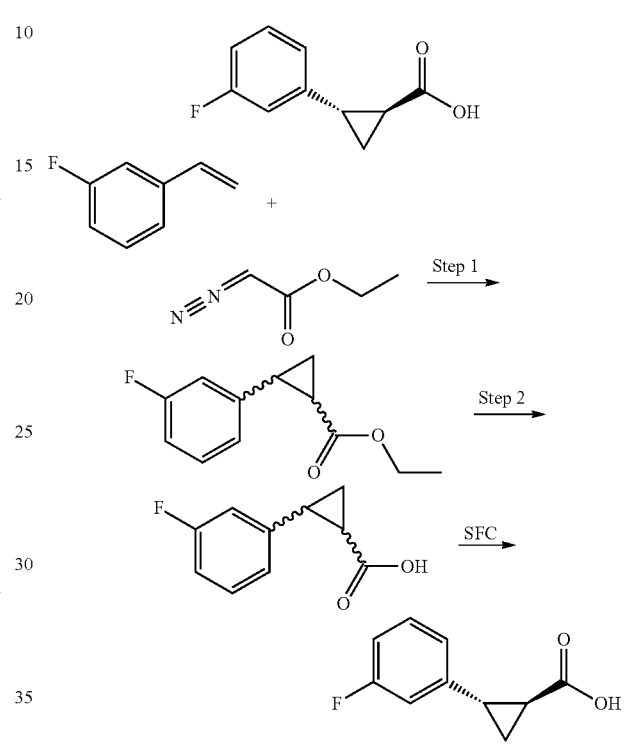

A round-bottomed flask was charged with 3-fluorostyrene (13.0 g, 0.107 mol) in anhydrous methylene chloride (130 mL). To this mixture was added rhodium acetate dimer (1.30 g, cat amount). A solution of ethyldiazoacetate (33.28 g, 0.291 mol) in anhydrous methylene chloride (130 mL) was added to the reaction via a syringe pump over 5 h and stirred at room temperature for 1 h in darkness. The reaction mixture was filtered through a plug of celite, which was washed with water followed by brine. The organic layer Was dried over Na$_2$SO$_4$ and evaporated to dryness. Flash chromatography (silica, EtOAc/petroleum ether 1:9) gave rac-trans 2-(3-fluoro-phenyl)-cyclopropanecarboxylic acid ethyl ester (13.0 g, 59%) as a colorless liquid sufficiently pure for the next step.
Step 2:
To a solution of rac-trans 2-(3-fluoro-phenyl)-cyclopropanecarboxylic acid ethyl ester (13.0 g, 0.062 mol) in MeOH (310 mL) was added a solution of KOH (35.0 g, 0.625 mol) in MeOH (150 mL) at 0° C. After addition of the base the reaction mixture was stirred at room temperature for 18 h. The reaction mixture was poured into water and extracted with methylene chloride (2×50 mL). The aqueous layer was acidified with 10% HCl. The resulting mixture was extracted with methylene chloride (2×150 mL). The combined organic layers were dried over Na$_2$SO$_4$ and evaporated to dryness to give rac-trans-2-(3-fluoro-phenyl)-cyclopropanecarboxylic acid as colorless crystals (9.5 g, 85%). Separation of the isomers by chiral SFC (Method D) gave the title compound (1S,2S)-2-(3-fluoro-phenyl)-cyclopropanecarboxylic acid IM47 as colorless crystals (3.27 g, 17% overall yield from 3-fluorostyrene) sufficiently pure for the next step. Specific optical rotation +263.4° $[\alpha]_D^{20}$ (C=1% MeOH)

IM48:
(1S,2S)-2-(4-Fluoro-phenyl)-cyclopropanecarboxylic acid

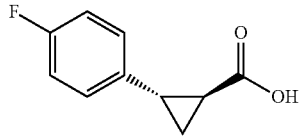 [SMILES: O=C(O)[C@H]1C[C@@H]1c1ccc(F)cc1]

Prepared analogously to IM48 using SFC method E to give the title compound sufficiently pure for the next step (3.1 g, 13% overall yield from 4-fluorostyrene). Specific optical rotation +263.2° $[\alpha]_D^{20}$ (C=1% MeOH)
Other Intermediates.

IM49: (R)-2-Methyl-propane-2-sulfinic acid [2-(tert-butyl-dimethyl-silanyloxy)-ethylidene]-amide

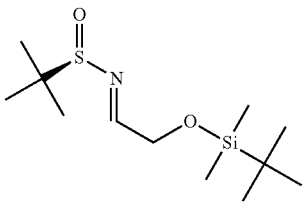 [SMILES: CC(C)(C)[S@@](=O)/N=C/CO[Si](C)(C)C(C)(C)C]

(R)-(+)-2-methyl-2-propanesulfinamide (8.70 g, 71.8 mmol), pyridinium p-toluenesulfonate (0.902 g, 3.59 mmol) and MgSO₄ (43.2 g, 359 mmol) was suspended in methylene chloride (25 mL). A solution of (tert-butyldimethylsilyloxy)acetaldehyde (25.0 g, 144 mmol) dissolved in methylene chloride (10 mL) was added drop wise at room temperature. The reaction was stirred at room temperature overnight. The mixture was evaporated to dryness. Flash chromatography (silica, EtOAc/heptanes 1:4) gave the title compound as an oil that slowly solidified upon standing (18.3 g, 92%) sufficiently pure for the next step.

Example 1

Preparation of Example Compounds of the Invention

Compound 1: (1S,2S)-2-Phenyl-cyclopropanecarboxylic acid [(S)-1-(6-isopropoxy-pyridin-3-yl)-ethyl]-amide

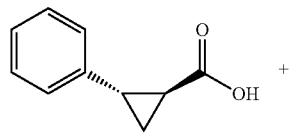

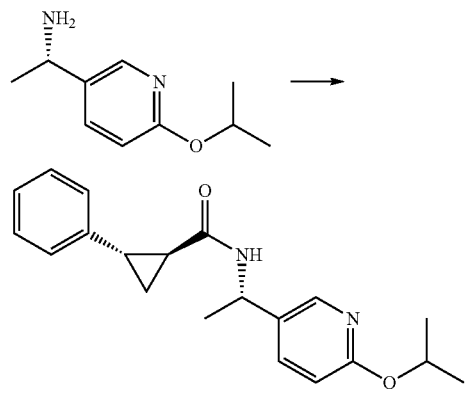

Trans-2-phenyl-1-cyclopropanecarboxylic acid IM46 (0.590 g, 3.64 mmol) was dissolved in DMF (15.0 mL). N,N,N',N'-tetramethyl-O-(7-azabenzotriazol-1-yl)uronium hexafluorophosphate (1.38 g, 3.63 mmol) was added. Triethylamine (1.10 mL, 7.89 mmol) was then added and the mixture was stirred for 15 minutes at room temperature. This mixture was added drop wise to a solution of (S)-1-(6-isopropoxy-pyridin-3-yl)-ethylamine IM24 (0.655 g, 3.63 mmol) dissolved in DMF (15.0 mL) over 2 minutes. The mixture was stirred at room temperature over night. The mixture was evaporated to dryness. The residue was transferred to a silica gel column and eluded with EtOAc/heptanes 1:1 to give Compound 1 as a solid. This solid was dissolved in EtOAc (50 mL) and to this solution was slowly added heptanes (50 mL). The mixture was concentrated to approx. 25 mL in vacuo and this solution was cooled in an ice/water bath. A white precipitate formed. The solids was collected by filtration and dried in vacuo to give the title compound as colorless crystals (0.794 g, 67%). LC-MS (m/z) 325.4 (MH+), $t_R$=1.51 min (method A). ¹H NMR (500 MHz, DMSO) δ 8.57-8.50 (m, 1H), 8.06 (br s, 1H), 7.65-7.57 (m, 1H), 7.30-7.24 (m, 2H), 7.20-7.14 (m, 1H), 7.10 (d, J=7.5 Hz, 2H), 6.69 (d, J=8.5 Hz, 1H), 5.25-5.16 (m, 1H), 4.98-4.88 (m, 1H), 2.24-2.15 (m, 1H), 1.94-1.88 (m, 1H), 1.41-1.32 (m, 4H), 1.26 (d, J=6.2 Hz, 6H), 1.20 (ddd, J=8.5, 6.1, 4.1 Hz, 1H). Diastereomeric excess >95% based on ¹H NMR.

Compound 2: (1S,2S)-2-Phenyl-cyclopropanecarboxylic acid [(S)-1-(5-methyl-pyridin-2-yl)-ethyl]-amide

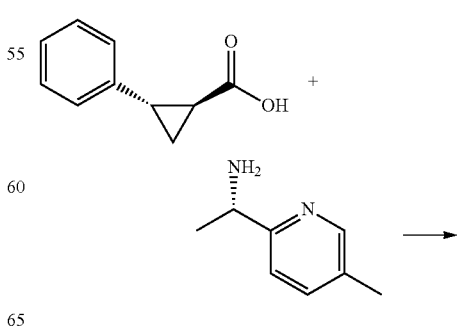

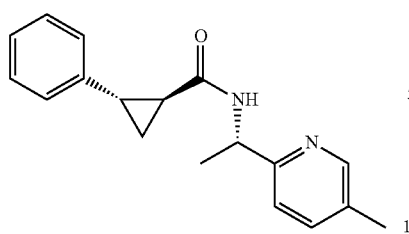

N-(3-Dimethylaminopropyl)-N'-ethylcarbodiimide hydrochloride (0.709 g, 3.70 mmol) and 1-hydroxybenzotriazole (0.667 g, 4.93 mmol) were added to a stirred mixture of IM46 (0.60 g, 3.70 mmol) and commercially available (S)-1-(5-methyl-pyridin-2-yl)-ethylamine hydrochloride (Supplier Netchem Inc., Catalog No 528193) (0.426 g, 2.47 mmol) and N,N-diisopropylethylamine (0.859 ml, 4.93 mmol) in THF (25 ml). The solution was stirred at rt overnight. Water was added and the mixture was extracted with EtOAc (3×80 ml). The combined organic phases were washed with brine, dried over MgSO4, filtered and the solvent was evaporated of in vac. The crude product was purified by silica gel chromatography (EtOAc in heptanes 1:1). Yield of Compound 2: 110 mg (16%). LC-MS (m/z) 281.1 (MH+), $t_R$=0.91 min (method A).

Compound 3: (1S,2S)-2-Phenyl-cyclopropanecarboxylic acid [(S)-1-(6-methoxy-pyridin-3-yl)-ethyl]-amide

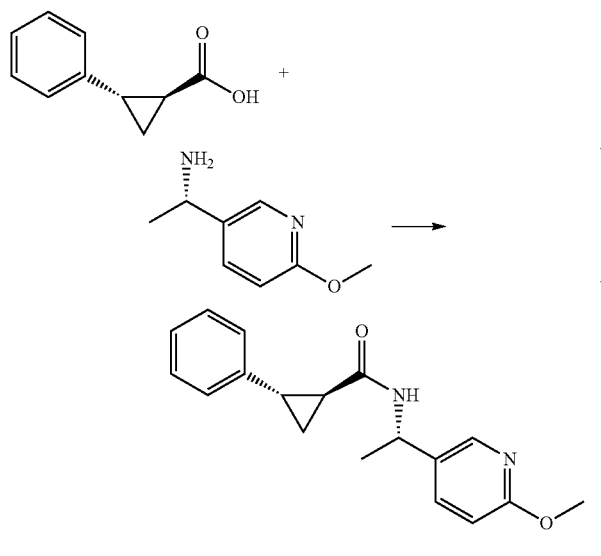

Prepared analogously to Compound 1 using IM46 and commercially available (S)-1-(6-methoxy-pyridin-3-yl)-ethylamine (Supplier Netchem Inc., Catalog No 517706). Yield=0.88 g (66%). $^1$H NMR (500 MHz, DMSO) δ 8.55 (d, 1H), 8.10 (s, 1H), 7.63 (d, 1H), 7.27 (m, 2H), 7.17 (m, 1H), 7.10 (d, 2H), 6.78 (d, 1H), 4.93 (m, 1H), 3.72 (s, 3H), 2.21 (m, 1H), 1.90 (m, 1H), 1.37 (m, 4H), 1.20 (m, 1H). LC-MS (m/z) 297.4 (MH+), $t_R$=1.36 min (method A).

Compound 4: (1S,2S)-2-Phenyl-cyclopropanecarboxylic acid [(S)-1-(6-methyl-pyridin-3-yl)-ethyl]-amide

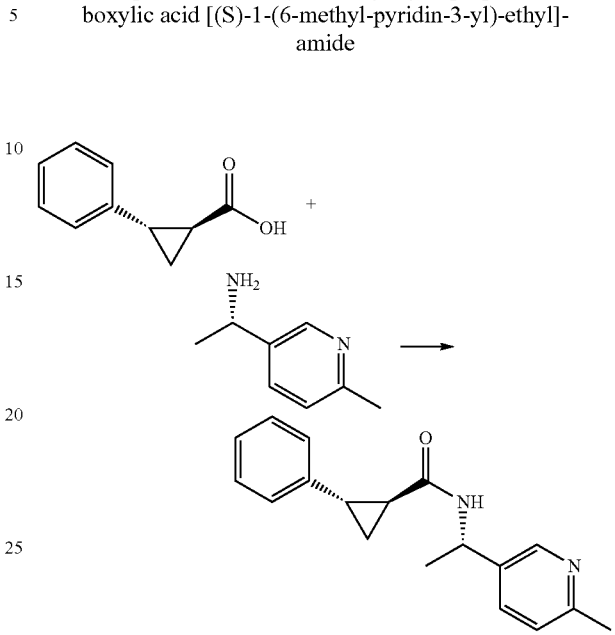

Prepared analogously to Compound 1 using IM46 and commercially available (S)-1-(6-methyl-pyridin-3-yl)-ethylamine (Supplier Netchem Inc., Catalog No 519526). Yield=0.27 g (21%). $^1$H NMR (600 MHz, DMSO) δ 8.61 (d, 1H), 8.37 (s, 1H), 7.57 (d, 1H), 7.26 (m, 2H), 7.16 (m, 2H), 7.09 (d, 2H), 4.92 (m, 1H), 2.41 (s, 3H), 2.19 (m, 1H), 1.91 (m, 1H), 1.36 (m, 4H), 1.20 (m, 1H). LC-MS (m/z) 251.2 (MH+), $t_R$=0.88 min (method A).

Compound 5: (1S,2S)-2-Phenyl-cyclopropanecarboxylic acid [(S)-1-(6-cyano-pyridin-3-yl)-ethyl]-amide

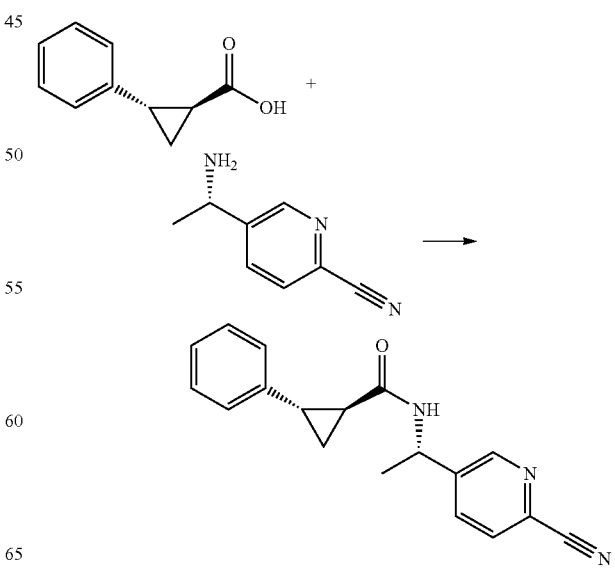

Prepared analogously to Compound 2 using IM46 and commercially available 5-((S)-1-amino-ethyl)-pyridine-2-carbonitrile hydrochloride (Supplier Netchem Inc., Catalog No 549493). Yield=0.104 g (20%). %). $^1$H NMR (600 MHz, DMSO) δ 8.76 (d, 1H), 8.71 (s, 1H), 8.02 (d, 1H), 7.94 (d, 1H), 7.29 (m, 2H), 7.19 (m, 1H), 7.12 (d, 2H), 5.03 (m, 1H), 2.21 (m, 1H), 1.92 (m, 1H), 1.40 (d, 3H), 1.37 (m, 1H), 1.23 (m, 1H). LC-MS (m/z) 292.0 (MH+), $t_R$=1.31 min (method A).

Compound 6: (1S,2S)-2-Phenyl-cyclopropanecarboxylic acid [(S)-1-(6-trifluoromethyl-pyridin-3-yl)-ethyl]-amide

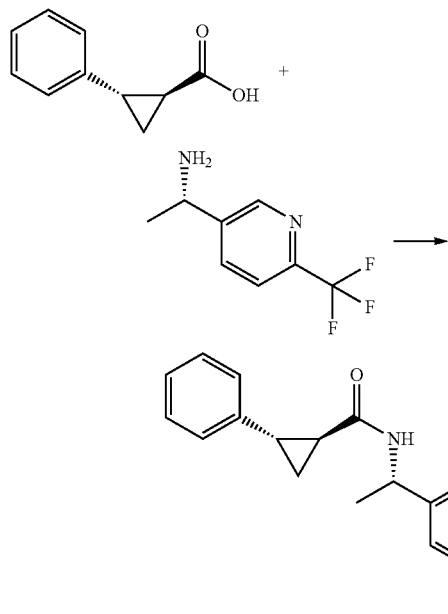

Prepared analogously to Compound 2 using IM46 and commercially available (S)-1-(6-trifluoromethyl-pyridin-3-yl)-ethylamine hydrochloride. (Supplier Netchem Inc., Catalog No 517662). Yield=0.33 g (55%). %). $^1$H NMR (500 MHz, DMSO) δ 8.77 (d, 1H), 8.72 (s, 1H), 7.99 (d, 1H), 7.88 (d, 1H), 7.27 (m, 2H), 7.17 (m, 1H), 7.13 (d, 2H), 5.05 (m, 1H), 2.20 (m, 1H), 1.93 (m, 1H), 1.41 (d, 3H), 1.37 (m, 1H), 1.23 (m, 1H). LC-MS (m/z) 335.2 (MH+), $t_R$=1.59 min (method A).

Compound 7: (1S,2S)-2-Phenyl-cyclopropanecarboxylic acid [(S)-1-(6-ethoxy-pyridin-3-yl)-ethyl]-amide

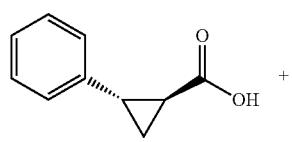

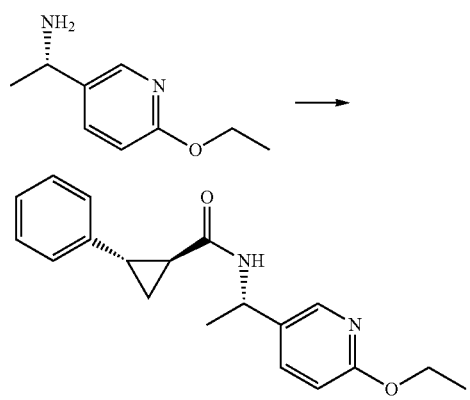

Prepared analogously to Compound 2 using IM46 and commercially available (S)-1-(6-ethoxy-pyridin-3-yl)-ethylamine hydrochloride (Supplier Sial Gmbh, Catalog No 528261-HCl, Lot no LNA098). Yield=0.30 g (39%). $^1$H NMR (500 MHz, DMSO) δ 8.54 (d, 1H), 8.08 (s, 1H), 7.82 (d, 1H), 7.27 (m, 2H), 7.16 (m, 1H), 7.12 (d, 2H), 8.73 (d, 1H), 4.92 (m, 1H), 4.25 (q, 2H), 2.20 (m, 1H), 1.91 (m, 1H), 1.35 (m, 4H), 1.30 (t, 3H), 1.19 (m, 1H). LC-MS (m/z) 311.4 (MH+), $t_R$=1.45 min (method A).

Compound 8: (1S,2S)-2-Phenyl-cyclopropanecarboxylic acid [(S)-1-(6-ethyl-pyridin-3-yl)-ethyl]-amide

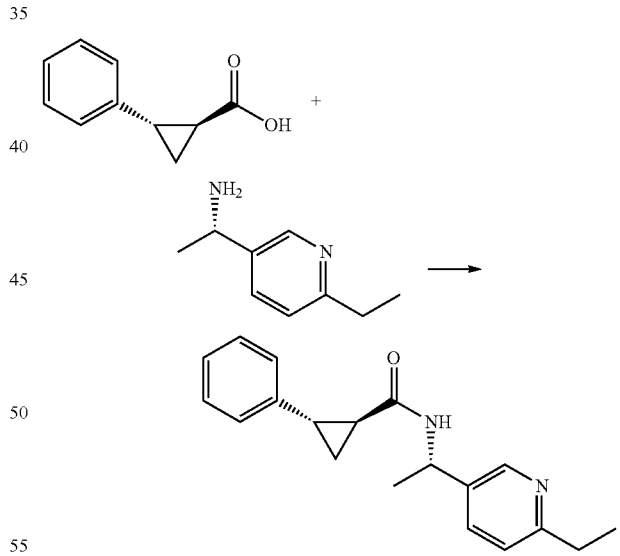

Prepared analogously to Compound 1 using IM46 and IM25. Yield=0.44 g (65%). $^1$H NMR (500 MHz, DMSO) δ 8.51 (d, 1H), 8.41 (s, 1H), 7.27-7.14 (m, 4H), 7.10 (d, 2H), 4.96 (m, 1H), 2.72 (q, 2H), 2.20 (m, 1H), 1.92 (m, 1H), 1.38 (m, 4H), 1.21 (m, 4H). LC-MS (m/z) 295.1 (MH+). $t_R$=0.90 ml (method A).

Compound 9: (1S,2S)-2-Phenyl-cyclopropanecarboxylic acid [(S)-1-(6-methoxymethyl-pyridin-3-yl)-ethyl]-amide

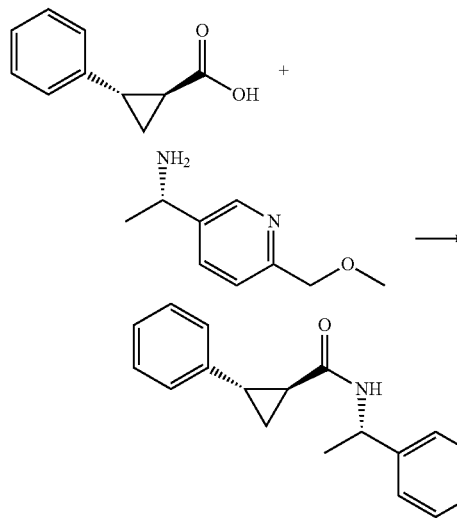

Prepared analogously to Compound 1 using IM46 and IM26. Yield=0.18 g (40%). ¹H NMR (500 MHz, DMSO) δ 8.63 (d, 1H), 8.10 (s, 1H), 7.71 (d, 1H), 7.37 (d, 1H), 7.27 (m, 2H), 7.17 (m, 1H), 7.10 (d, 2H), 4.97 (m, 1H), 3.37 (s, 3H), 2.21 (m, 1H), 1.93 (m, 1H), 1.39 (m, 4H), 1.20 (m, 1H). LC-MS (m/z) 311.3 (MH+). $t_R$=0.98 min (method A).

Compound 10: (1S,2S)-2-Phenyl-cyclopropanecarboxylic acid {(S)-1-[6-(2,2,2-trifluoro-ethoxy)-pyridin-3-yl]-ethyl}-amide

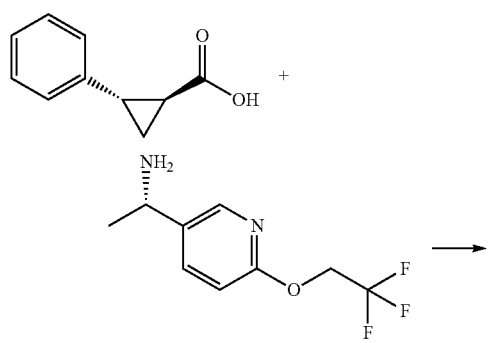

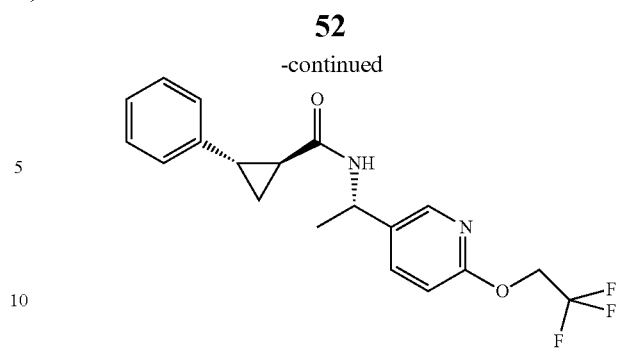

Prepared analogously to Compound 1 using IM46 and IM27. Yield=0.695 g (50%). ¹H NMR (500 MHz, DMSO) δ 8.62 (d, 1H), 8.12 (s, 1H), 7.73 (d, 1H), 7.27 (m, 2H), 7.15 (m, 1H), 7.10 (d, 2H), 6.95 (d), 4.97 (m, 3H), 2.20 (m, 1H), 1.91 (m, 1H), 1.37 (m, 4H), 1.20 (m, 1H). LC-MS (m/z) 385.3 (MH+), $t_R$=1.78 min (method A).

Compound 11: (1S,2S)-2-Phenyl-cyclopropanecarboxylic acid {(S)-1-[6-(2-methoxy-ethoxy)-pyridin-3-yl]-ethyl}-amide

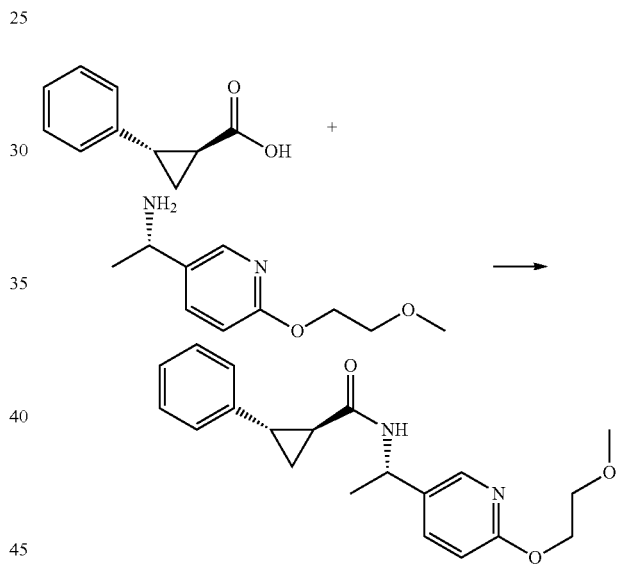

Prepared analogously to Compound 1 using IM46 and IM28. Yield=0.758 g (30%). ¹H NMR (500 MHz, DMSO) δ 8.57 (d, 1H), 8.08 (s, 1H), 7.65 (d, 1H), 7.26 (m, 2H), 7.17 (m, 1H), 7.10 (d, 2H), 6.78 (d, 1H), 4.92 (m, 2H), 4.32 (m, 2H), 3.62 (m, 2H), 3.27 (s, 3H), 2.20 (m, 1H), 1.89 (m, 1H), 1.37 (m, 4H), 1.20 (m, 1H). LC-MS (m/z) 341.0 (MH+), $t_R$=1.33 min (method A).

Compound 12: (1S,2S)-2-Phenyl-cyclopropanecarboxylic acid [(S)-1-(2-ethoxy-pyridin-4-yl)-ethyl]-amide

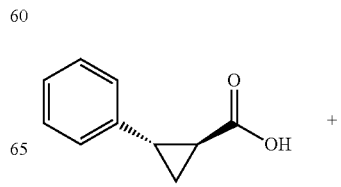

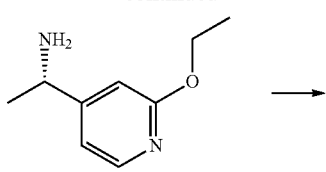

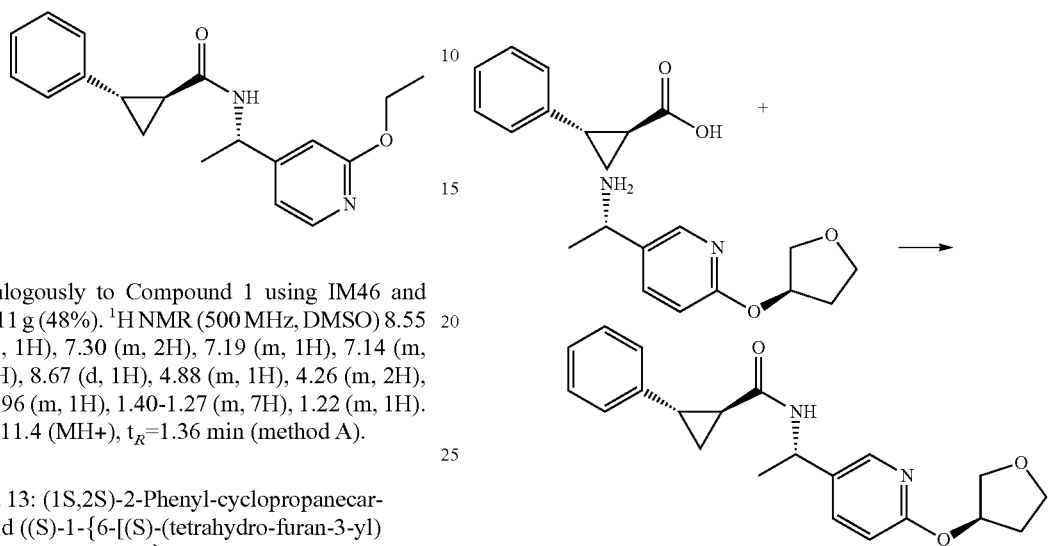

Prepared analogously to Compound 1 using IM46 and IM29. Yield=0.11 g (48%). ¹H NMR (500 MHz, DMSO) 8.55 (d, 1H), 8.06 (s, 1H), 7.30 (m, 2H), 7.19 (m, 1H), 7.14 (m, 2H), 6.90 (d, 1H), 8.67 (d, 1H), 4.88 (m, 1H), 4.26 (m, 2H), 2.20 (m, 1H), 1.96 (m, 1H), 1.40-1.27 (m, 7H), 1.22 (m, 1H). LC-MS (m/z) 311.4 (MH+), $t_R$=1.36 min (method A).

Compound 13: (1S,2S)-2-Phenyl-cyclopropanecarboxylic acid ((S)-1-{6-[(S)-(tetrahydro-furan-3-yl)oxy]-pyridin-3-yl}-ethyl)-amide

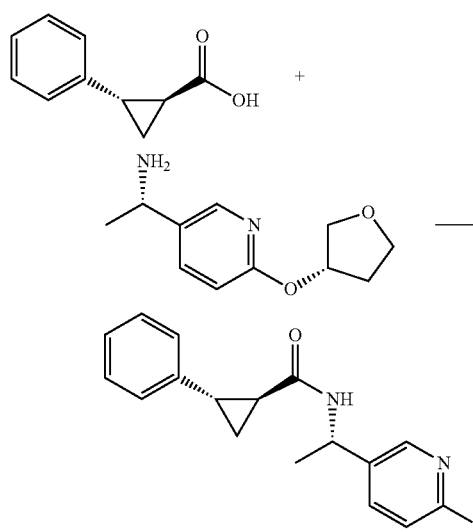

Prepared analogously to Compound 1 using IM46 and IM30. Yield=0.983 g (62%). 1H-NMR (500 MHz, DMSO) δ 8.55 (d, 1H), 8.09 (s, 1H), 7.64 (d, 1H), 7.27 (m, 2H), 7.16 (m, 1H), 7.11 (d, 2H), 6.78 (d, 1H), 5.48 (m, 1H) 4.96 (m, 1H), 3.92 (m, 1H), 3.85 (m, 1H), 3.74 (m, 2H), 2.21 (m, 2H), 1.95 (m, 2H), 1.37 (m, 4H), 1.19 (m, 1H). LC-MS (m/z) 353.3 (MH+), $t_R$=1.45 min (method A).

Compound 14: (1S,2S)-2-Phenyl-cyclopropanecarboxylic acid ((S)-1-{6-[(R)-(tetrahydro-furan-3-yl)oxy]-pyridin-3-yl}-ethyl)-amide Prepared analogously to Compound 1 using IM46 and IM31. Yield 0.696 g (62%). 1H-NMR (500 MHz, DMSO) δ 8.56 (d, 1H), 8.08 (s, 1H), 7.63 (d, 1H), 7.27 (m, 2H), 7.15 (m, 1H), 7.10 (d, 2H), 6.78 (d, 1H), 5.47 (m, 1H) 4.92 (m, 1H), 3.91 (m, 1H), 3.84 (m, 1H), 3.73 (m, 2H), 2.20 (m, 2H), 1.95 (m, 2H), 1.37 (m, 4H), 1.20 (m, 1H). LC-MS (m/z) 353.3 (MH+), $t_R$=1.45 min (method A).

Compound 15: (1S,2S)-2-Phenyl-cyclopropanecarboxylic acid ((S)-1-[1,3]dioxolo[4,5-b]pyridin-6-yl-ethyl)-amide

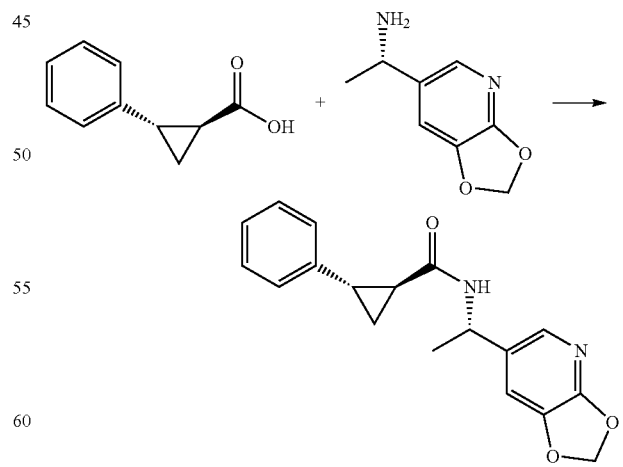

Prepared analogously to Compound 1 using IM46 and IM32. Yield=0.572 g (42%). 1H-NMR (500 MHz, DMSO) δ 8.54 (d, 1H), 7.52 (s, 1H), 7.27 (m, 2H), 7.20-7.15 (m, 2H), 7.10 (d, 2H), 6.11 (s, 2H), 4.91 (m, 1H), 2.20 (m, 1H), 1.88

(m, 1H), 1.35 (m, 4H), 1.20 (m, 1H). LC-MS (m/z) 311.1 (MH+), $t_R$=0.61 min (method B).

Compound 16: (1S,2S)-2-Phenyl-cyclopropanecarboxylic acid [(S)-1-(2,3-dihydro-[1,4]dioxino[2,3-b]pyridin-7-yl)-ethyl]-amide

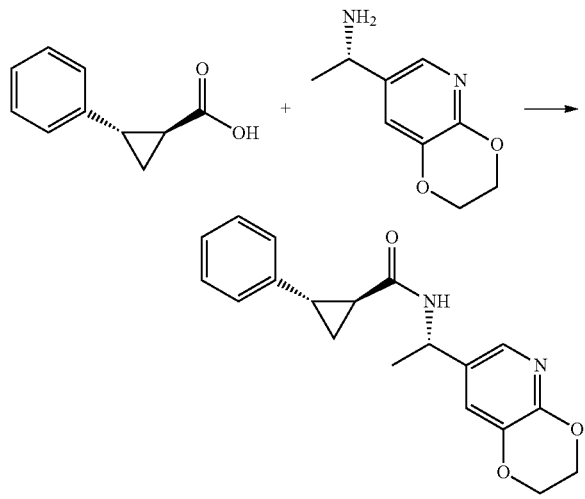

Prepared analogously to Compound 1 using IM46 and IM33. Yield=0.877 g (39%). 1H-NMR (500 MHz, DMSO) δ 8.52 (d, 1H), 7.68 (s, 1H), 7.27 (m, 2H), 7.22 (s, 1H), 7.18 (m, 1H), 7.10 (d, 2H), 4.92 (m, 1H), 4.37 (d, 2H), 4.22 (d, 2H), 2.20 (m, 1H), 1.90 (m, 1H), 1.35 (m, 4H), 1.20 (m, 1H). LC-MS (m/z) 325.5 (MH+). $t_R$=1.28 min (method A).

Compound 17: (1S,2S)-2-Phenyl-cyclopropanecarboxylic acid [(S)-1-(2-ethoxy-pyrimidin-5-yl)-ethyl]amide

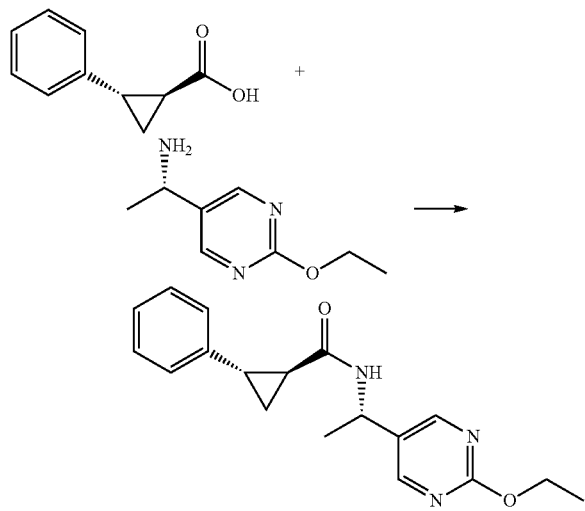

Prepared analogously to Compound 1 using IM46 and IM34. Yield=0.195 g (32%). 1H-NMR (600 MHz, DMSO) δ 8.53 (d, 1H), 8.52 (s, 2H), 7.26 (m, 2H), 7.16 (s, 1H), 7.10 (d, 2H), 4.92 (m, 1H), 4.32 (m, 2H), 2.20 (m, 1H), 1.88 (m, 1H), 1.40 (d, 3H), 1.35 (m, 1H), 1.31 (t, 3H), 1.20 (m, 1H). LC-MS (m/z) 312.2 (MH+), $t_R$=0.62 min (method B).

Compound 18: (1S,2S)-2-Phenyl-cyclopropanecarboxylic acid [(S)-1-(6-chloro-pyridin-3-yl)-ethyl]-amide

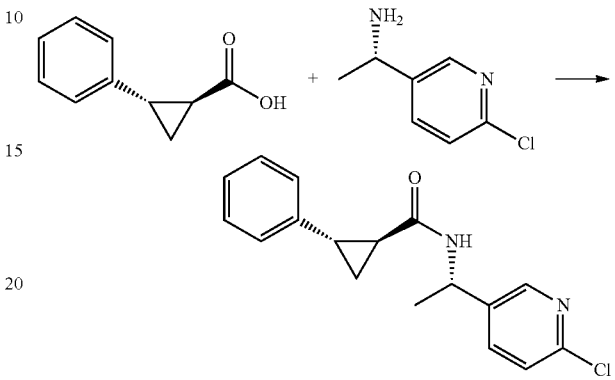

Prepared analogously to Compound 1 using IM46 and commercially available (S)-1-(6-Chloro-pyridin-3-yl)-ethylamine (Aurora building blocks catalogue nr A06.81-4.555). Yield=1.40 g (71%), 1H-NMR (500 MHz, DMSO) δ 8.68 (d, 1H), 8.36 (s, 1H), 7.78 (d, 1H), 7.48 (d, 1H), 7.28 (m, 2H), 7.18 (m, 1H), 7.11 (d, 2H), 4.99 (m, 1H), 2.20 (m, 1H), 1.92 (m, 1H), 1.37 (m, 4H), 120 (m, 1H). LC-MS (m/z) 301.2 and 303.1 (MH+), $t_R$=0.87 min (method B).

Compound 19: (1S,2S)-2-Phenyl-cyclopropanecarboxylic acid {(S)-1-[6-(oxetan-3-yloxy)-pyridin-3-yl]-ethyl)}-amide

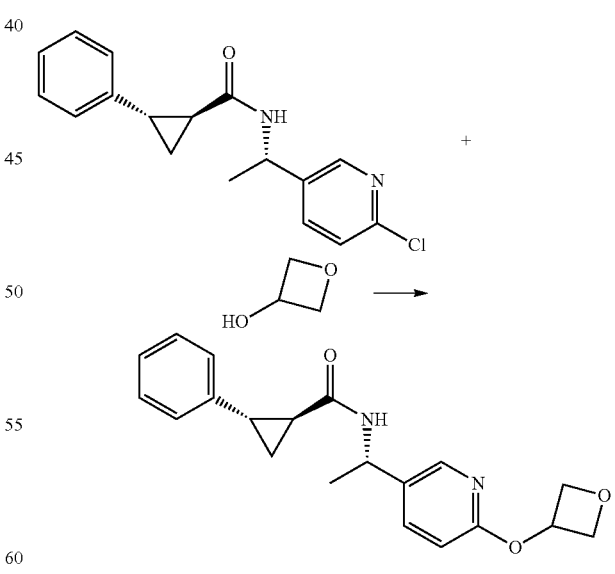

(1S,2S)-2-Phenyl-cyclopropanecarboxylic acid [(S)-1-(6-chloro-pyridin-3-yl)-ethyl]-amide (Compound 18) (2.00 g, 6.65 mmol) was dissolved in DMF (50 ml). Oxetan-3-ol (4.00 g, 54 mmol) and dicesium carbonate (16.2 g, 49.9 mmol) were added and the mixture was heated at 100° C. ON. The mixture was poured out into brine and extracted with EtOAc.

The organic layer was washed with brine, dried (MgSO4) and was filtered and then evaporated to dryness. The residue was transferred to a silica gel column end eluded with EtOAc/heptanes 1:1 to give Compound 19 as a solid. This solid was dissolved in a mixture of THF (10 ml), EtOAc (20 mL) and heptanes (10 ml). The mixture was concentrated to approx. 15 mL in vacuo and this solution was cooled in an ice/water bath. A white precipitate formed. The solids was collected by filtration and dried in vacuo to give the title compound as colorless crystals (0.097 g, 4%). %). 1H-NMR (500 MHz, DMSO) δ 8.55 (d, 1H), 8.04 (s, 1H), 7.70 (d, 1H), 7.25 (m, 2H), 7.15 (m, 1H), 7.10 (d, 2H), 6.87 (d, 1H), 5.52 (m, 1H), 4.95 (m, 1H), 4.87 (m, 2H), 4.53 (m, 2H), 2.20 (m, 1H), 1.90 (m, 1H), 1.37 (m, 4H), 1.21 (m, 1H). LC-MS (m/z) 339.2 (MH+), $t_R$=0.63 min (method B). Mp=151-153 C.

Compound 20: (1S,2S)-2-Phenyl-cyclopropanecarboxylic acid [(S)-1-(6-cyanomethoxy-pyridin-3-yl)-ethyl]-amide

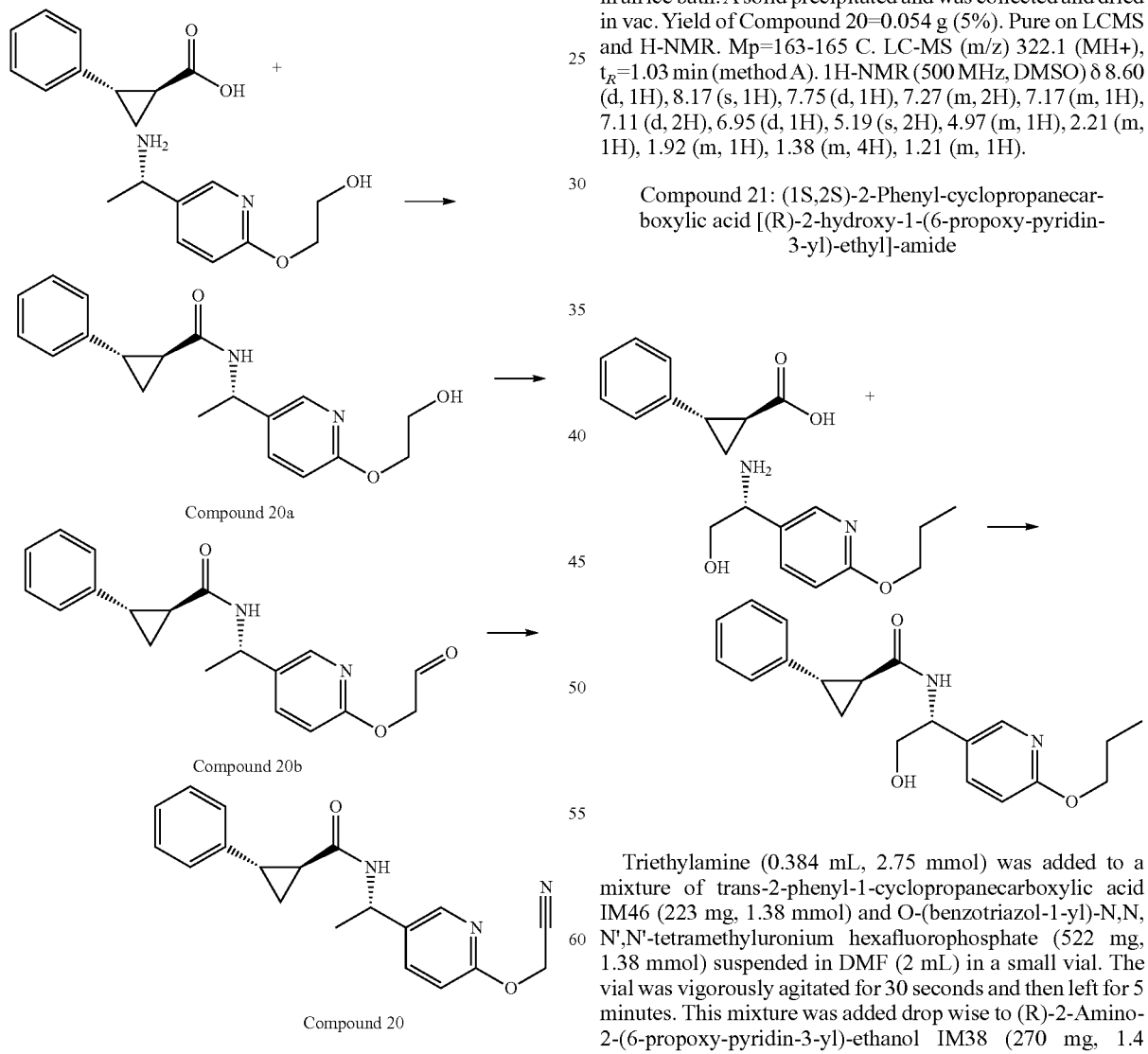

Compound 20a was prepared analogously to Compound 1 using IM46 and IM35 for the first step. Yield of Compound 20a=1.50 g 71%). Pure on TLC (Eluent EtOAc. Rf=0.5). This material (1.50 g, 4.36 mmol) was dissolved in a mixture of DMSO (50 ml) and THF (50 ml) and 1-Hydroxy-1,2-benziodoxol-3(1H)-one 1-Oxide (1.34 g, 4.8 mmol) was added and the mixture was stirred at rt overnight. The mixture was added to a mixture of brine and EtOAc and the phases were separated. The organic phases was dried over MgSO$_4$ and was rotovaped. The crude product was purified by silica gel chromatography (Eluent EtOAc). Yield of Compound 20b=1.08 g (72%). Pure on TLC (Eluent EtOAc, Rf=0.7). This material (1.05 g, 3.24 mmol) was dissolved in THF (10 ml), and MeCN (50 ml) and added drop wise to a solution of 1-Hydroxy-1,2-benziodoxol-3(1H)-one 1-Oxide (1.36 g, 4.86 mmol) in ammonia in water (13 M, 25 ml) and THF (5 ml) and MeCN (5 ml). The mixture was stirred at rt ON.

The organic phases was dried over MgSO4 and was rotovaped. The crude product was purified by silica gel chromatography (Eluent EtOAc in heptanes 4:1) to give 177 mg impure product. This material was THF (10 ml) and EtOAc (10 ml) and heptanes (10 ml) were added. The mixture was rotovaped until aprox 10 ml solvent was left and then cooled in an ice bath. A solid precipitated and was collected and dried in vac. Yield of Compound 20=0.054 g (5%). Pure on LCMS and H-NMR. Mp=163-165 C. LC-MS (m/z) 322.1 (MH+), $t_R$=1.03 min (method A). 1H-NMR (500 MHz, DMSO) δ 8.60 (d, 1H), 8.17 (s, 1H), 7.75 (d, 1H), 7.27 (m, 2H), 7.17 (m, 1H), 7.11 (d, 2H), 6.95 (d, 1H), 5.19 (s, 2H), 4.97 (m, 1H), 2.21 (m, 1H), 1.92 (m, 1H), 1.38 (m, 4H), 1.21 (m, 1H).

Compound 21: (1S,2S)-2-Phenyl-cyclopropanecarboxylic acid [(R)-2-hydroxy-1-(6-propoxy-pyridin-3-yl)-ethyl]-amide Triethylamine (0.384 mL, 2.75 mmol) was added to a mixture of trans-2-phenyl-1-cyclopropanecarboxylic acid IM46 (223 mg, 1.38 mmol) and O-(benzotriazol-1-yl)-N,N,N',N'-tetramethyluronium hexafluorophosphate (522 mg, 1.38 mmol) suspended in DMF (2 mL) in a small vial. The vial was vigorously agitated for 30 seconds and then left for 5 minutes. This mixture was added drop wise to (R)-2-Amino-2-(6-propoxy-pyridin-3-yl)-ethanol IM38 (270 mg, 1.4 mmol) dissolved in DMF (3 mL). After 1 h the mixture was poured into a mixture of EtOAc (40 mL) and brine (20 mL). The organic layer was dried over MgSO$_4$ and evaporated to dryness. Flash chromatography (silica, 10-100% EtOAc in heptanes) gave the title compound as a white solid (0.134 g, 29%). LC-MS (m/z) 341.0 (MH+), $t_R$=1.52 min (method A). 1H-NMR (800 MHz, DMSO) δ 8.53 (d, J=8.2 Hz, 1H), 8.04 (br a, 1H), 7.64-7.57 (m, 1H), 7.30-7.23 (m, 2H), 7.19-7.14 (m, 1H), 7.10 (d, J=7.3 Hz, 2H), 6.74 (d, J=8.5 Hz, 1H), 4.96-4.90 (m, 1H), 4.88-4.80 (m, 1H), 4.16 (t, J=6.7 Hz, 2H), 3.61-3.49 (m, 2H), 2.23-2.15 (m, 1H), 2.04-1.95 (m, 1H), 1.74-1.64 (m, 2H), 1.40-1.32 (m, 1H), 1.23-1.13 (m, 1H), 0.84 (t, J=7.4 Hz, 3H).

Compound 22: (1S,2S)-2-Phenyl-cyclopropanecarboxylic acid [(R)-2-hydroxy-1-(6-trifluoromethyl-pyridin-3-yl)-ethyl]-amine

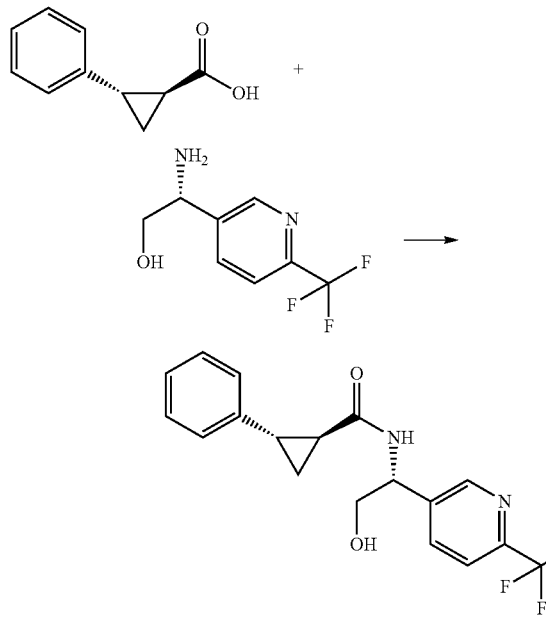

N-(3-Diethylaminopropyl)-N'-ethylcarbodiimide hydrochloride (0.39 g, 2.03 mmol) and 1-hydroxybenzotriazole (0.366 g, 2.71 mmol) were added to a stirred mixture of IM46 (0.22 g, 1.36 mmol) and commercially available (R)-2-amino-2-(6-trifluoromethyl-pyridin-3-yl)-ethanol hydrochloride (Supplier Netchem Inc., Catalog No 517882) (0.494 g, 2.03 mmol) and N,N-diisopropylethylamine (0.472 ml, 2.71 mmol) in THF (20 ml). The solution was stirred at rt overnight. Water was added and the mixture was extracted with EtOAc (3×80 ml). The combined organic phases were washed with brine, dried over MgSO$_4$, filtered and the solvent was evaporated of in vac. The crude product was purified by silica gel chromatography (EtOAc in heptanes 10:1). Yield of Compound 22 475 mg (78%). 1H-NMR (500 MHz, DMSO) δ 8.77 (d, 1H), 8.74 (s, 1H), 8.00 (d, 1H), 7.88 (d, 1H), 7.27 (m, 2H), 7.18 (m, 1H), 7.13 (d, 2H), 5.04 (m, 2H), 3.64 (m, 2H), 2.22 (m, 1H), 2.07 (m, 1H), 1.37 (m, 1H), 1.37 (m, 1H), 1.23 (m, 1H). LC-MS (m/z) 351.1 (MH+), $t_R$=1.51 min (method A).

Compound 23: (1S,2S)-2-Phenyl-cyclopropanecarboxylic acid [(R)-(5-cyano-pyridin-2-yl)-2-hydroxy-ethyl]-amide

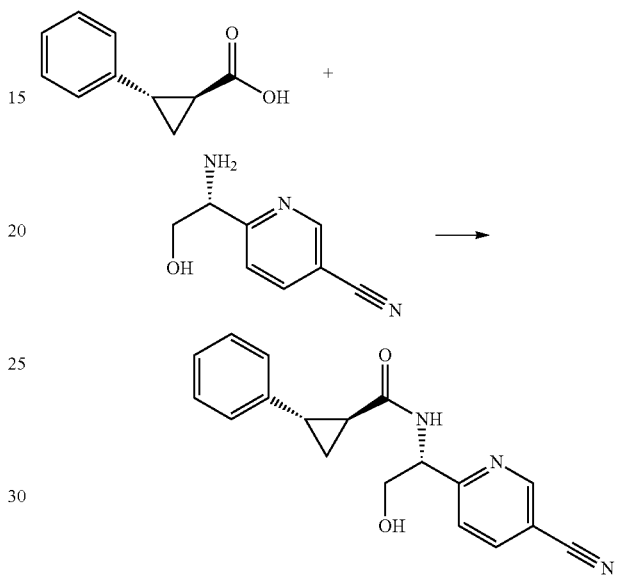

Prepared analogously to Compound 22 using IM46 and commercially available 6-((R)-1-amino-2-hydroxy-ethyl)-nicotinonitrile (Suppler Netchem Inc., Catalog No 549885). Yield of Compound 23 230 mg (61%). 1H-NMR (500 MHz, DMSO) δ 8.97 (s, 1H), 8.72 (d, 1H), 8.26 (d, 1H), 7.52 (d, 1H), 7.27 (m, 2H), 7.18 (t, 1H), 7.11 (d, 2H), 5.05-4.95 (m, 2H), 3.70 (m, 2H), 2.20 (m, 1H), 2.17 (m, 1H), 1.36 (m, 1H), 1.20 (m, 1H). LC-MS (m/z) 308.1 (MH+). $t_R$=1.21 min (method A).

Compound 24: (1S,2S)-2-Phenyl-cyclopropanecarboxylic acid [(R)-2-hydroxy-1-(6-methoxy-pyridin-3-yl)-ethyl]-amide

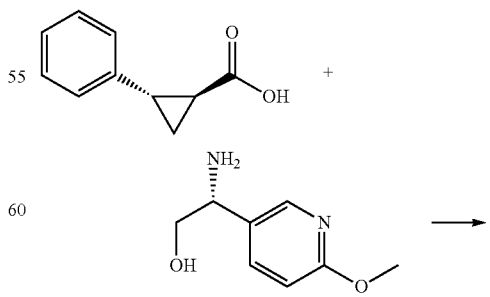

-continued

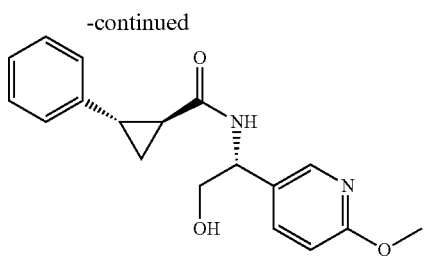

Prepared analogously to Compound 22 using IM46 and commercially available (R)-2-Amino-2-(6-methoxy-pyridin-3-yl)-ethanol (Supplier Netchem Inc., Catalog No 517926). Yield of Compound 24=763 mg (22%). 1H-NMR (500 MHz, DMSO) δ 8.53 (d, 1H), 8.09 (s, 1H), 7.63 (d, 1H), 7.27 (m, 2H), 7.15 (m, 1H), 7.12 (m, 2H), 6.77 (d, 1H), 4.95 (m, 2H), 4.85 (m, 2H), 3.83 (s, 3H), 3.57 (m, 2H), 2.21 (m, 1H), 2.00 (m, 1H), 1.37 (m, 1H), 1.19 (m, 1H). LC-MS (m/z) 313.1 (MH+), $t_R$=1.53 min (method A).

Compound 25: (1S,2S)-2-Phenyl-cyclopropanecarboxylic acid [(R)-2-hydroxy-1-(6-methyl-pyridin-3-yl)-ethyl]-amide

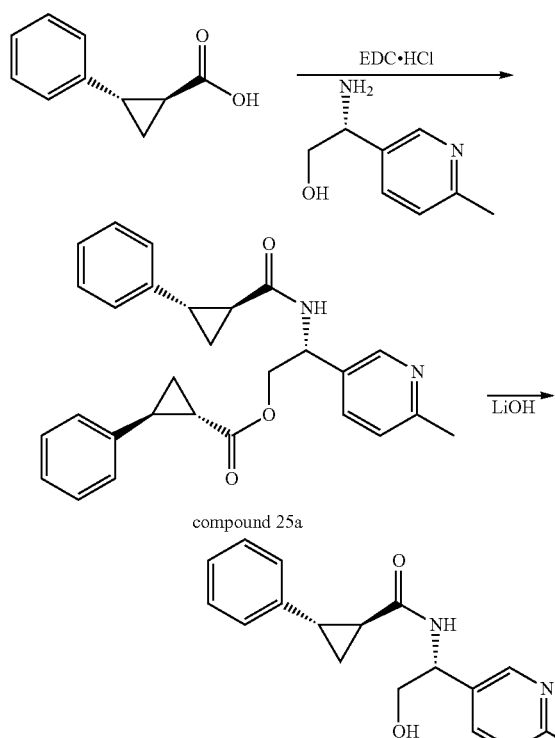

compound 25a

N-(3-Dimethylaminopropyl)-N'-ethylcarbodiimide hydrochloride (0.318 g, 1.65 mmol) and 1-hydroxybenzotriazole (0.223 g, 1.65 mmol) were added to a stirred mixture of IM46 (0.18 g, 1.1 mmol) and commercially available (R)-2-Amino-2-(6-methyl-pyridin-3-yl)-ethanol dihydro-chloride (Supplier Netchem Inc., Catalog No 549945) (0.128 g, 1.21 mmol) and N,N-diisopropylethylamine (0.575 ml, 3.30 mmol) in THF (10 ml). The solution was stirred at rt overnight. Water was added and the mixture was extracted with EtOAc. The organic phase was rotovaped to produce 140 mg of Compound 25a. LC-MS (m/z) 441.4 (MH+), $t_R$=1.44 min (method A). Compound 25a was dissolved in THF and LiOH (1M) was added and the mixture was stirred 30 min. A solid precipitated and was isolated by filtration and dried in vac. Yield of Compound 25=110 mg (34%). 1H-NMR (500 MHz, DMSO) a 8.53 (d, 1H), 8.09 (s, 1H), 7.63 (d, 1H), 7.27 (m, 2H), 7.15 (m, 1H), 7.12 (m, 2H), 6.77 (d, 1H), 4.95 (m, 2H), 4.85 (m, 2H), 3.83 (s, 3H), 3.57 (m, 2H), 2.21 (m, 1H), 2.00 (m, 1H), 1.37 (m, 1H), 1.19 (m, 1H). LC-MS (m/z) 297.3 (MH+). $t_R$=0.78 min (method A).

Compound 26: (1S,2S)-2-Phenyl-cyclopropanecarboxylic acid [(R)-2-hydroxy-1-(6-isopropoxy-pyridin-3-yl)-ethyl]-amide

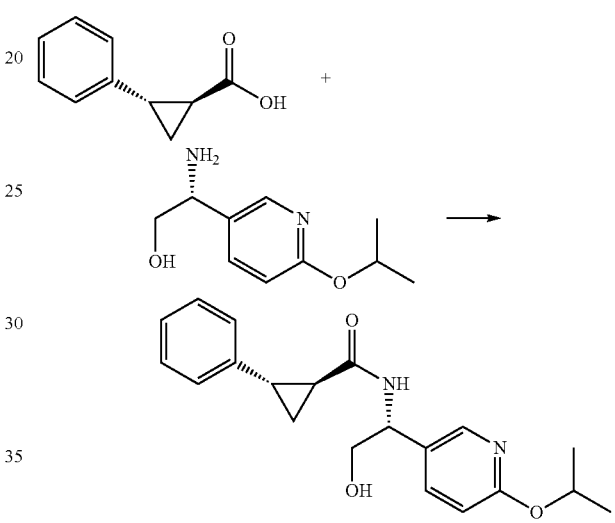

Prepared analogously to Compound 21 using IM46 and IM37. Yield of Compound 26=667 mg (77%). 1H-NMR (600 MHz, DMSO) δ 8.52 (d, 1H), 8.03 (s, 1H), 7.60 (d, 1H), 7.25 (m, 2H), 7.15 (m, 1H), 7.10 (d, 2H), 6.67 (d, 1H), 5.20 (m, 1H), 4.92 (t, 1H), 4.83 (m, 1H), 3.55 (m, 2H), 2.20 (m, 1H), 2.00 (m, 1H), 1.35 (m, 1H), 1.24 (d, 6H), 1.19 (m, 1H). LC-MS (m/z) 341.0 (MH+), $t_R$=1.45 min (method A).

Compound 27: (1S,2S)-2-(3-Fluoro-phenyl)-cyclopropanecarboxylic acid [(R)-1-(6-ethoxy-pyridin-3-yl)-2-hydroxy-ethyl]-amide

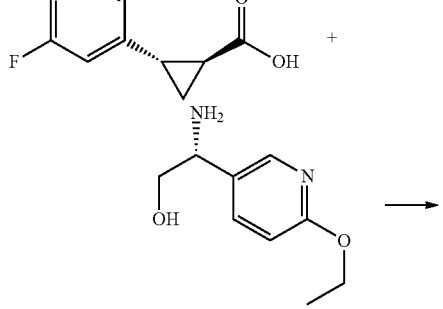

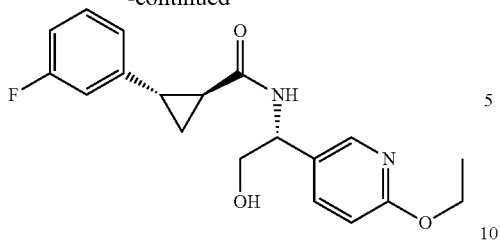

Prepared analogously to Compound 21 using IM47 and IM38. Yield of Compound 27=90 mg (19%). 1H-NMR (600 MHz, DMSO) δ 8.53 (d, 1H), 8.05 (s, 1H), 7.62 (m, 1H), 7.28 (m, 1H), 6.97 (m, 3H), 6.73 (d, 1H), 4.83 (m, 1H), 4.24 (m, 2H), 3.55 (m, 2H), 2.22 (m, 1H), 2.03 (m, 1H), 1.37 (m, 1H), 1.28 (t, 3H), 1.22 (m, 1H). LC-MS (m/z) 345.0 (MH+), $t_R$=0.63 min (method B).

Compound 28: (1S,2S)-2-(4-Fluoro-phenyl)-cyclopropanecarboxylic acid [(R)-1-(6-ethoxy-pyridin-3-yl)-2-hydroxy-ethyl]-amide

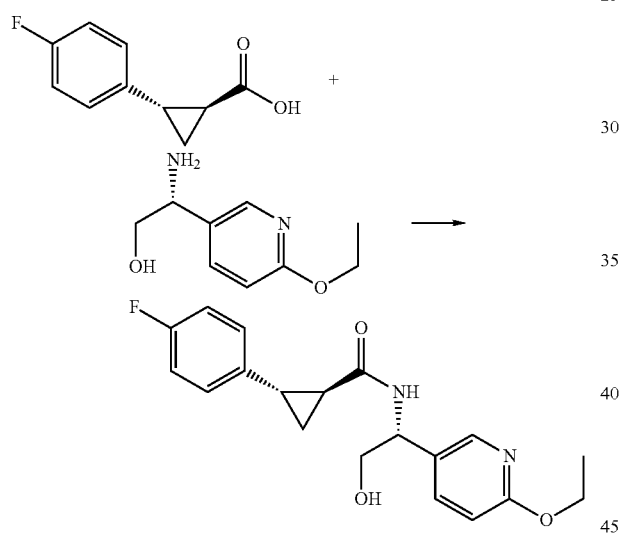

Prepared analogously to Compound 21 using IM48 and IM38. Yield of Compound 28=93 mg while solid. (54%). 1H-NMR (600 MHz, DMSO) δ 8.56 (d, 1H), 8.07 (s, 1H), 7.82 (m, 1H), 7.18 (m, 2H), 7.12 (m, 2H), 6.77 (d, 1H), 4.93 (t, 1H), 4.83 (m, 1H), 4.25 (dd, 2H), 3.52 (m, 2H), 2.27 (m, 1H), 1.97 (m, 1H), 1.30 (m, 4H), 1.15 (m, 1H). LC-MS (m/z) 345.0 (MH+), LC-MS (m/z) 345.0 (MH+), $t_R$=1.36 min (method A).

Compound 29: (1S,2S)-2-(3-Fluoro-phenyl)-cyclopropanecarboxylic acid [(R)-2-hydroxy-1-(6-propoxy-pyridin-3-yl)-ethyl]-amide

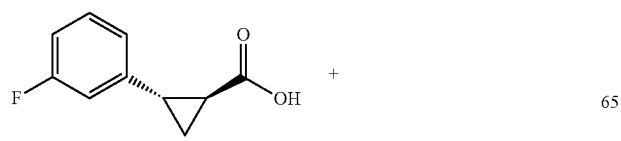

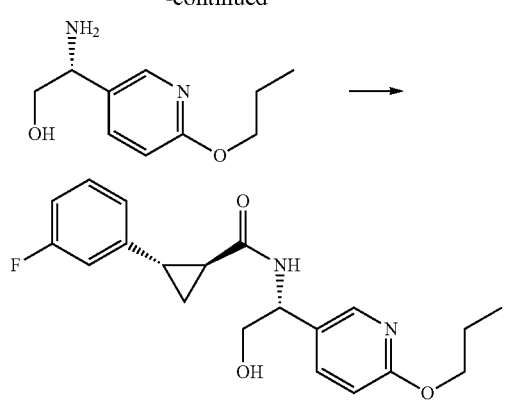

Prepared analogously to Compound 21 using IM47 and IM36. Yield=150 mg (30%). 1H-NMR (600 MHz, DMSO) δ 8.53 (d, 1H), 8.03 (s, 1H), 7.62 (d, 1H), 7.29 (m, 1H), 6.95 (m, 3H), 6.74 (d, 1H), 4.93 (m, 1H), 4.84 (m, 1H), 4.16 (t, 2H), 3.55 (m, 2H), 2.23 (m, 1H), 2.03 (m, 1H), 1.68 (m, 2H), 1.37 (m, 1H), 1.25 (m, 1H), 0.93 (t, 3H). LC-MS (m/z) 359.1 (MH+), $t_R$=1.57 min (method A).

Compound 30: (1S,2S)-2-(4-Fluoro-phenyl-cyclopropanecarboxylic acid [(R)-2-hydroxy-1-(5-propoxy-pyridin-3-yl)-ethyl]-amide

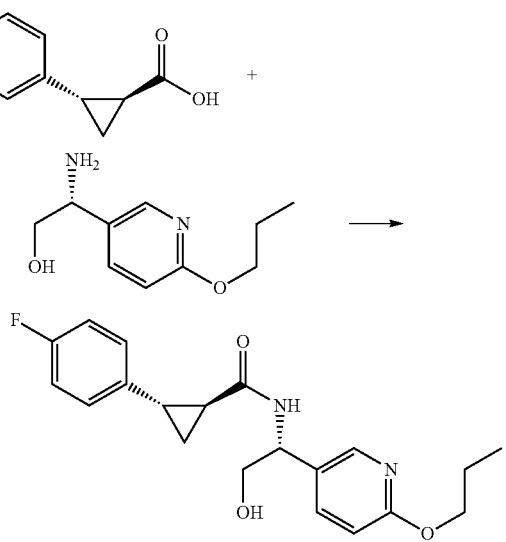

Prepared analogously to Compound 21 using IM48 and IM36. Yield 176 mg (36%). 1H-NMR (600 MHz, DMSO) δ 8.52 (d, 1H), 8.05 (s, 1H), 7.63 (d, 1H), 7.14 (m, 2H), 7.09 (m, 2H), 6.74 (d, 1H), 4.92 (t, 1H), 4.85 (m, 1H), 4.15 (t, 2H), 3.55

(m, 2H), 2.22 (m, 1H), 1.97 (m, 1H), 1.70 (m, 2H), 1.34 (m, 1H), 1.18 (m, 1H), 0.92 (t, 3H).

Compound 31: (1S,2S)-2-Phenyl-cyclopropanecarboxylic acid [(R)-1-(6-(2,2,2-d$_3$)-ethoxy-pyridin-3-yl)-2-hydroxy-ethyl]-amide

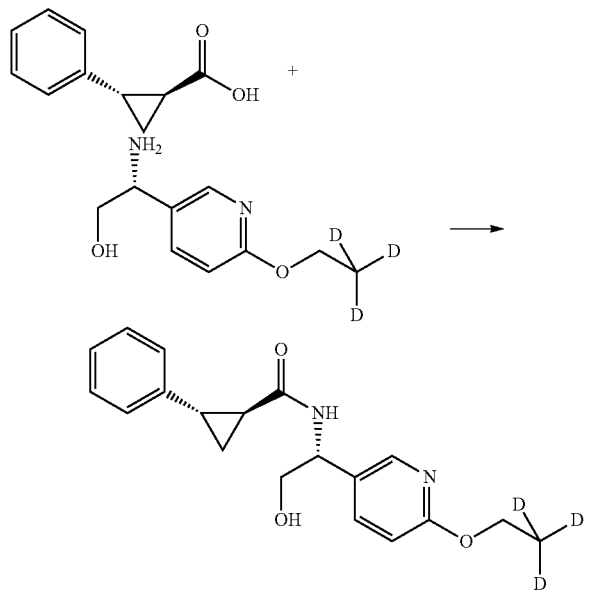

Prepared analogously to Compound 21 using IM46 and IM40. Yield=785 mg (66%). 1H-NMR (600 MHz, CDCl$_3$) δ 8.62 (s, 1H), 7.52 (d, 1H), 7.26 (m, 2H), 7.20 (m, 1H), 7.08 (d, 2H), 6.71 (d, 1H), 6.27 (m, 1H), 5.05 (m, 1H), 4.31 (s, 2H), 3.91 (m, 2H), 2.51 (m, 2H), 1.67 (m, 2H), 1.31 (m, 1H). LC-MS (m/z) 330.3 (MH+), $t_R$=1.32 min (method A).

Compound 32: (1S,2S)-2-(3-Fluoro-phenyl)-cyclopropanecarboxylic acid [(R)-1-(6-(1,1-d$_2$)-ethoxy-pyridin-3-yl)-2-hydroxy-ethyl]-amide

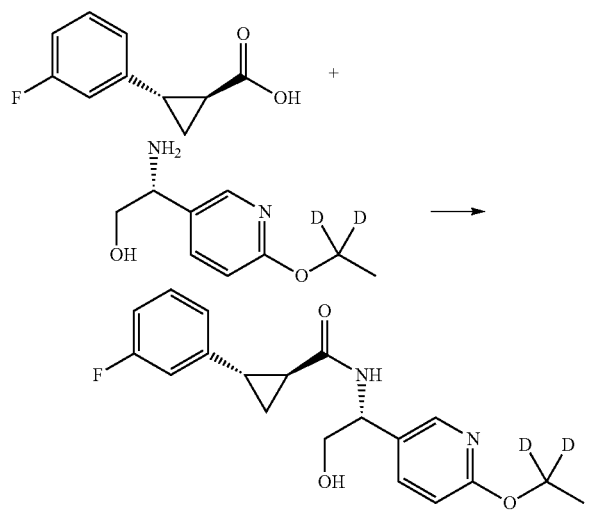

Prepared analogously to Compound 21 using IM47 and IM41. Yield=104 mg (44%). 1H-NMR (600 MHz, DMSO) δ 8.52 (d, 1H), 8.03 (s, 1H), 7.61 (m, 1H), 7.29 (m, 1H), 6.97 (m, 3H), 6.72 (d, 1H), 4.93 (m, 1H), 4.85 (m, 1H), 3.55 (m, 2H), 2.22 (m, 1H), 2.02 (m, 1H), 1.37 (m, 1H), 1.25 (m, 4H). LC-MS (m/z) 347.2 (MH+), $t_R$=0.64 min (method A).

Compound 33: (1S,2S)-2-Phenyl-cyclopropanecarboxylic acid [(R)-1-(6-ethoxy-pyridin-3-yl)-2-hydroxy-ethyl]-amide

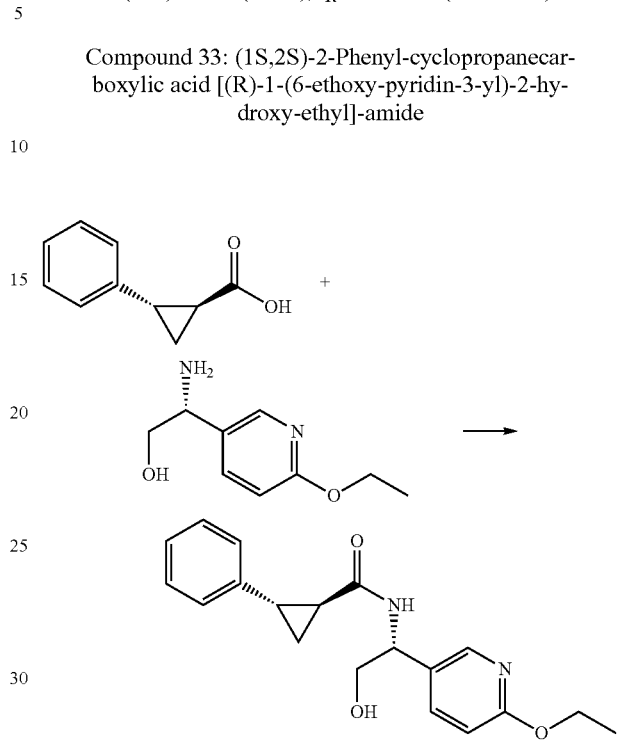

Prepared analogously to Compound 22 using IM46 and IM38. Yield=90 mg (28%). 1H-NMR (600 MHz, DMSO) δ 8.53 (d, 1H), 8.06 (s, 1H), 7.52 (m, 1H), 7.26 (m, 2H), 7.16 (m, 1H), 7.10 (d, 2H), 6.73 (d, 1H), 4.95 (t, 1H), 4.87 (m, 1H), 4.25 (m, 2H), 3.55 (m, 2H), 2.20 (m, 1H), 2.02 (m, 1H), 1.36 (m, 1H), 1.28 (t, 3H), 1.20 (m, 1H). LC-MS (m/z) 327.4 (MH+), $t_R$=0.57 min (method B).

Compound 34: (1S,2S)-2-(4-Fluoro-phenyl)-cyclopropanecarboxylic acid [(R)-1-(6-(1,1,2,2,2-d$_5$)-ethoxy-pyridin-3-yl)-2-hydroxy-ethyl]-amide

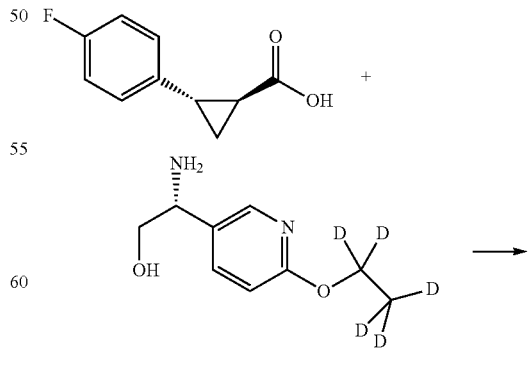

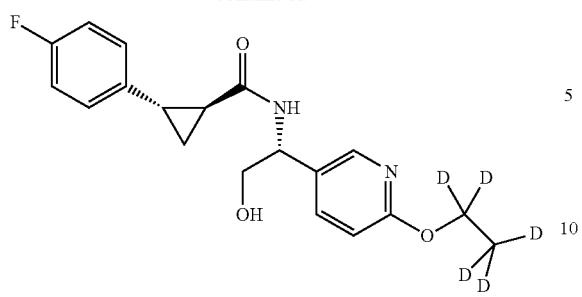

Prepared analogously to Compound 21 using IM48 and IM39. Yield=130 mg (41%). 1H-NMR (600 MHz, DMSO) δ 8.53 (d, 1H), 8.06 (s, 1H), 7.62 (m, 1H), 7.14 (m, 2H), 7.10 (m, 2H), 6.73 (d, 1H), 4.95 (br s, 1H), 4.84 (m, 1H), 3.55 (m, 2H), 2.22 (m, 1H), 1.96 (m, 1H), 1.34 (m, 1H), 1.18 (m, 1H). LC-MS (m/z) 350.2 (MH+), $t_R$=1.41 min (method A).

Compound 35: (1S,2S)-2-(4-Fluoro-phenyl)-cyclopropanecarboxylic acid [(R)-1-(6-(2,2,2-d$_3$)-ethoxypyridin-3-yl)-2-hydroxy-ethyl]-amide

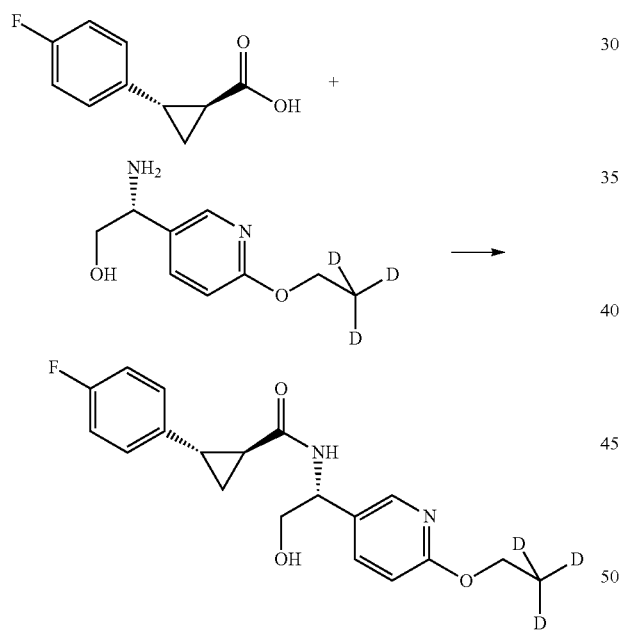

Prepared analogously to Compound 21 using IM48 and IM40. Yield=144 mg (41%). 1H-NMR (600 MHz, DMSO) δ 8.53 (d, 1H), 6.08 (s, 1H), 7.63 (m, 1H), 7.13 (m, 2H), 7.10 (m, 2H), 6.73 (d, 1H), 4.97 (br s, 1H), 4.86 (m, 1H), 4.24 (s, 2H), 3.57 (m, 2H), 2.23 (m, 1H), 1.97 (m, 1H), 1.37 (m, 1H), 1.20 (m, 1H). LC-MS (m/z) 347.9 (MH+), $t_R$=1.39 min (method A).

Compound 36: (1S,2S)-2-Phenyl-cyclopropanecarboxylic acid [(R)-1-(6-(1,1-d$_2$)-ethoxy-pyridin-3-yl)-2-hydroxy-ethyl]-amide

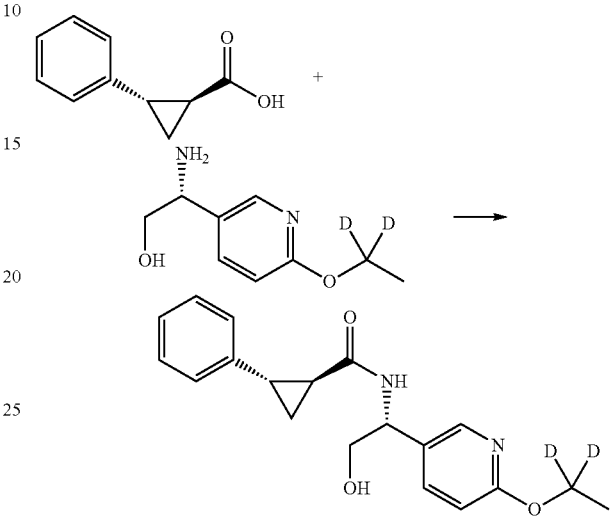

Prepared analogously to Compound 21 using IM46 and IM41. Yield=148 mg (67%). 1H-NMR (600 MHz, DMSO) δ 8.52 (d, 1H), 8.05 (s, 1H), 7.61 (d, 1H), 7.50 (m, 2H), 7.15 (m, 1H), 7.10 (d, 2H), 6.72 (d, 1H), 4.94 (t, 1H), 4.85 (m, 1H), 3.55 (m, 2H), 2.18 (m, 1H), 1.97 (m, 1H), 1.35 (m, 1H), 1.27 (s, 3H), 1.20 (m, 1H). LC-MS (m/z) 329.2 (MH+), $t_R$=0.61 min (method B).

Compound 37: (1S,2S)-2-(4-Fluoro-phenyl)-cyclopropanecarboxylic acid [(R)-1-(6-(1,1-d$_2$)-ethoxypyridin-3-yl)-2-hydroxy-ethyl]-amide

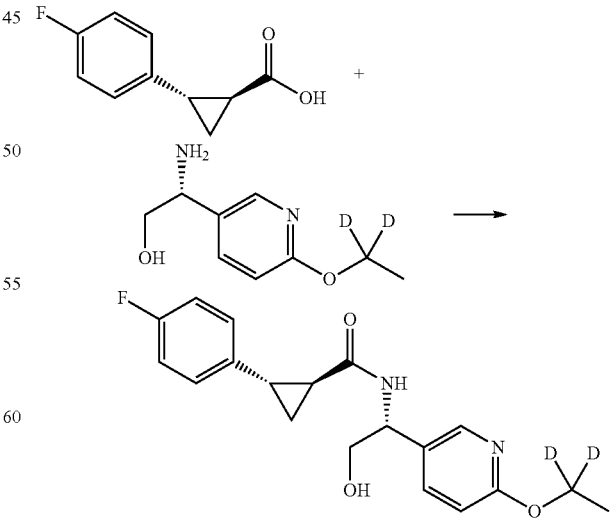

Prepared analogously to Compound 21 using IM48 and IM41. Yield=123 mg (52%). 1H-NMR (600 MHz, DMSO) δ

8.52 (d, 1H), 8.06 (s, 1H), 7.62 (m, 1H), 7.14 (m, 2H), 7.10 (m, 2H), 6.73 (d, 1H), 4.92 (t, 1H), 4.84 (m, 1H), 3.55 (m, 2H), 2.22 (m, 1H), 1.96 (m, 1H), 1.34 (m, 1H), 1.28 (s, 3H), 1.18 (m, 1H). LC-MS (m/z) 347.2 (MH+), $t_R$=1.41 min (method B).

Compound 38: (1S,2S)-2-Phenyl-cyclopropanecarboxylic acid [(R)-1-(6-(1,1,2,2,2-d₅)-ethoxy-pyridin-3-yl)-2-hydroxy-ethyl]-amide

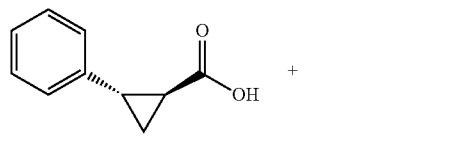

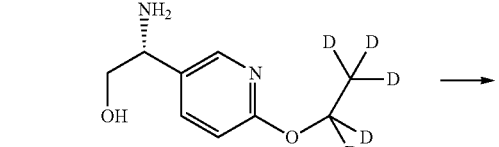

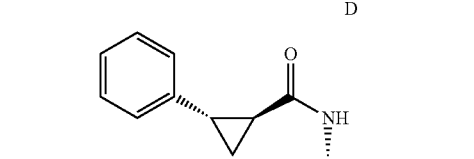

Prepared analogously to Compound 21 using IM46 and IM39. Yield=98 mg (32%). 1H-NMR (600 MHz, DMSO) δ 8.52 (d, 1H), 8.05 (s, 1H), 7.61 (d, 1H), 7.26 (t, 21), 7.16 (t, 1H), 7.10 (d, 2H), 6.72 (d, 1H), 4.93 (t, 1H), 4.83 (m, 1H), 3.55 (m, 2H), 2.18 (m, 1H), 1.99 (m, 1H), 1.35 (m, 1H), 1.20 (m, 1H). LC-MS (m/z) 332.2 (MH+), $t_R$=0.61 min (method B).

Compound 39: (1S,2S)-2-(3-Fluoro-phenyl)-cyclopropanecarboxylic acid [(R)-1-(6-(2,2,2-d₃)-ethoxy-pyridin-3-yl)-2-hydroxy-ethyl]-amide

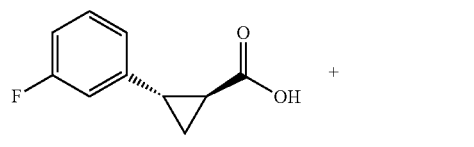

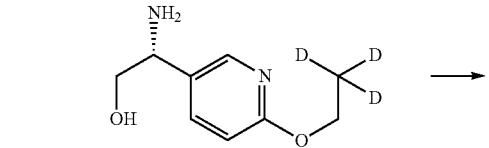

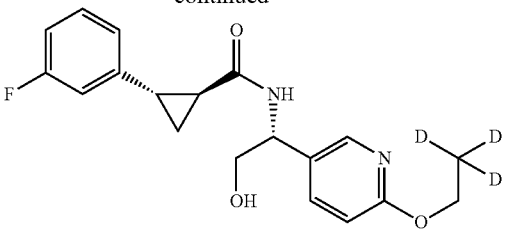

Prepared analogously to Compound 21 using IM47 and IM40. Yield=101 mg (29%). 1H-NMR (600 MHz, DMSO) δ 8.53 (d, 1H), 8.05 (s, 1H), 7.61 (d, 1H), 7.28 (m, 1H), 7.0-6.95 (m, 3H), 6.72 (d, 1H), 4.93 (t, 1H), 4.83 (m, 1H), 4.22 (s, 2H), 3.55 (m, 2H), 2.23 (m, 1H), 2.02 (m, 1H), 1.37 (m, 1H), 1.27 (m, 1H). LC-MS (m/z) 348.0 (MH+), $t_R$=1.43 min (method A).

Compound 40: (1S,2S)-2-Phenyl-cyclopropanecarboxylic acid [(R)-1-(6-cyclobutoxy-pyridin-3-yl)-2-hydroxy-ethyl]-amide

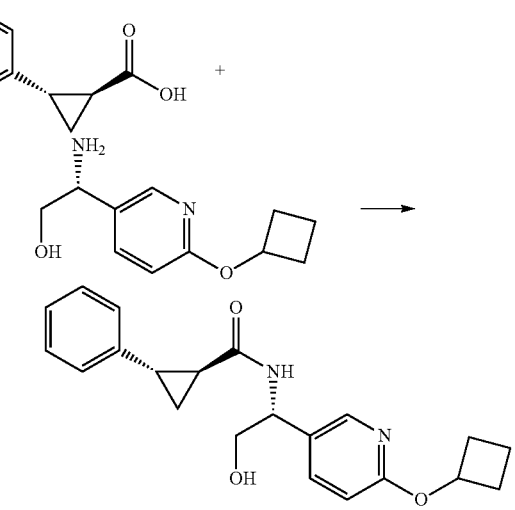

Prepared analogously to Compound 21 using IM46 and IM44. Yield=53 mg (30%). 1H-NMR (600 MHz, DMSO) δ 8.50 (d, 1H), 8.03 (s, 1H), 7.61 (d, 1H), 7.25 (m, 2H) 7.16 (m, 1H), 7.10 (m, 2H), 6.71 (d, 1H), 5.09 (m, 1H), 4.90 (t, 1H), 4.82 (m, 1H), 3.55 (m, 2H), 2.37 (m, 2H), 2.21 (m, 1H), 2.00 (m, 4H), 1.76 (m, 1H), 1.61 (m, 1H), 1.32 (m, 1H), 1.20 (m, 1H). LC-MS (m/z) 353.1 (MH+), $t_R$=0.70 min (method B).

Compound 41: (1S,2S)-2-(3-Fluoro-phenyl)-cyclopropanecarboxylic acid [(R)-1-(6-cyclobutoxy-pyridin-3-yl)-2-hydroxy-ethyl]-amide

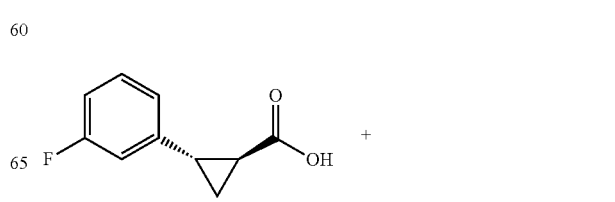

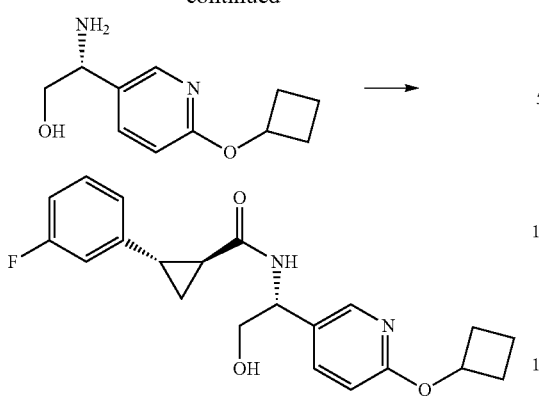

Prepared analogously to Compound 21 using IM47 and IM44. Yield=38 mg (20%). 1H-NMR (600 MHz, DMSO) δ 8.50 (d, 1H), 8.03 (s, 1H), 7.61 (d, 1H), 7.27 (m, 1H), 6.95 (m, 3H), 6.71 (d, 1H), 5.08 (m, 1H), 4.95 (br, s, 1H), 4.82 (m, 1H), 3.55 (m, 2H), 2.37 (m, 2H), 2.22 (m, 1H), 2.02 (m, 4H), 1.75 (m, 1H), 1.61 (m, 1H), 1.37 (m, 1H), 1.27 (m, 1H). LC-MS (m/z) 371.1 (MH+), $t_R$=0.71 min (method B).

Compound 42: (1S,2S)-2-(4-Fluoro-phenyl)-cyclopropanecarboxylic acid [(R)-1-(6-cyclobutoxy-pyridin-3-yl)-2-hydroxy-ethyl]-amide

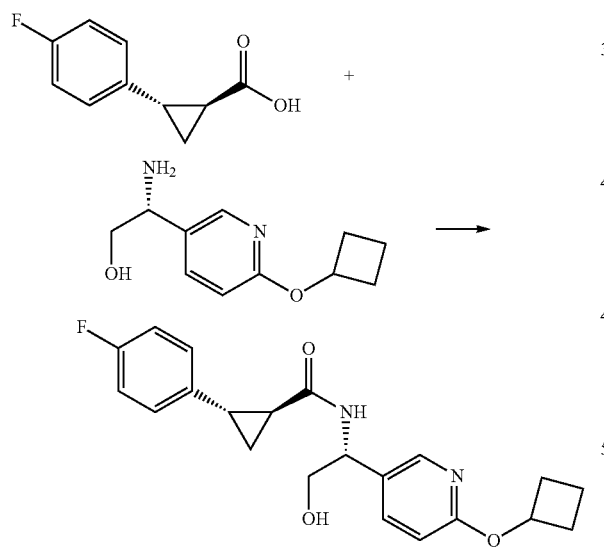

Prepared analogously to Compound 21 using IM48 and IM44. Yield=84 mg (45%). 1H-NMR (600 MHz, DMSO) δ 8.50 (d, 1H), 8.03 (s, 1H), 7.61 (d, 1H), 7.14 (m, 2H), 7.09 (m, 2H), 6.71 (d, 1H), 5.08 (m, 1H), 4.92 (t, 1H), 4.82 (m, 1H), 3.55 (m, 2H), 2.37 (m, 2H), 2.21 (m, 1H), 2.05-1.95 (m, 4H), 1.75 (m, 1H), 1.61 (m, 1H), 1.32 (m, 1H), 1.17 (m, 1H). LC-MS (m/z) 371.1 (MH+), $t_R$=0.71 min (method B).

Compound 43: (1S,2S)-2-Phenyl-cyclopropanecarboxylic acid ((R)-2-hydroxy-1-{6-[(R)-(tetrahydrofuran-3-yl)oxy]-pyridin-3-yl}-ethyl)-amide

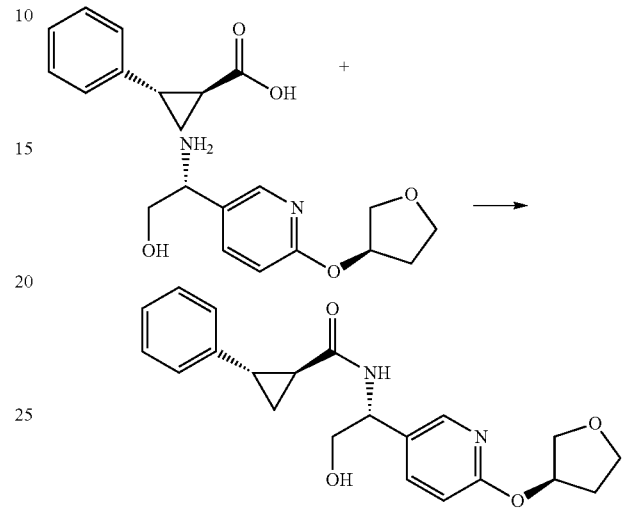

Prepared analogously to Compound 21 using IM48 and IM43. Yield=1.34 g white solid (60%). $^1$H NMR (400 MHz, CDCl$_3$): δ 8.08 (s, 1H), 7.51 (d, J=8.4 Hz, 1H), 7.18-7.25 (m, 3H), 7.04-7.06 (m, 2H), 6.68-6.71 (m, 1H), 6.36-6.39 (m, 1H), 5.50-5.53 (m, 1H), 5.04-5.05 (m, 1H), 3.88-4.01 (m, 6H), 2.48-2.50 (m, 1H), 2.21-2.26 (m, 1H), 2.11-2.13 (m, 1H), 1.62-1.71 (m, 2H), 1.27-1.31 (m, 1H). LC-MS (m/z) 369.2 (MH+), $t_R$=2.04 min (method WXE-AB01). $[\alpha]_D^{20}$=178.6 (C=0.2, CHCl$_3$)

Compound 44: (1S,2S)—N-[(1R)-2-hydroxy-1-[6-[(3S)-tetrahydrofuran-3-yl]oxy-3-pyridyl]ethyl]-2-phenyl-cyclopropanecarboxamide

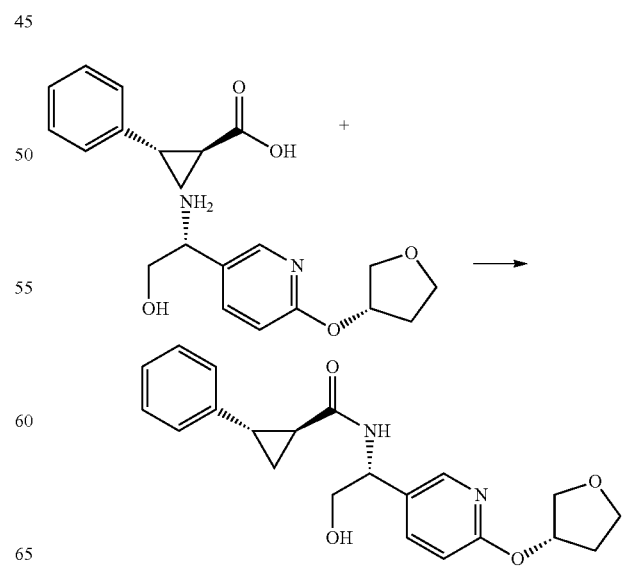

Prepared analogously to Compound 21 using IM46 and IM42. Yield=2.10 g white sold (50%). ¹H NMR (400 MHz, CDCl₃): δ 8.09 (m, 1H), 7.52-7.55 (m, 1H), 7.29 (m, 1H), 7.25-7.27 (m, 1H), 7.20-7.21 (m, 1H), 7.17-7.19 (d, J=7.2 Hz, 2H), 6.70-6.73 (d, J=8.8 Hz, 1H), 6.34-0.36 (d, J=7.2 Hz, 1H), 5.50-5.53 (m, 1H), 5.04-5.05 (d, J=6.8 Hz, 1H), 3.94-4.03 (m, 2H), 3.85-3.91 (m, 4H), 2.48-2.50 (m, 1H), 2.21-2.26 (m, 1H), 2.11-2.13 (m, 1H), 1.62-1.71 (m, 2H), 1.27-1.31 (m, 1H). LC-MS (m/z) 389.2 (MH+), $t_R$=2.03 min (method WXE-AB01). $[\alpha]_D^{20}$=160.9 (C=0.21, CHCl₃).

Compound 45: (1S,2S)-2-((Z)-1-Methylene-penta-2,4-dienyl)-cyclopropanecarboxylic acid {(R)-2-hydroxy-1-[6-(tetrahydro-pyran-4-yloxy)-pyridin-3-yl]-ethyl}-amide

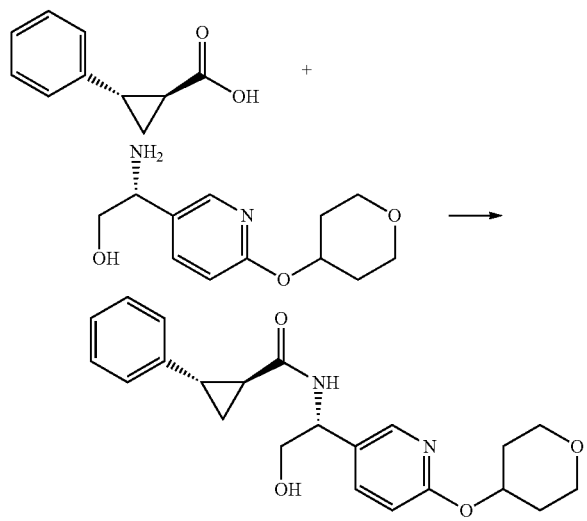

Prepared analogously to Compound 1 using IM46 and IM45. Yield=2.5 g white sold (44%). ¹H NMR ((400 MHz, CDCl₃): δ 8.09 (s, 1H), 7.52-7.55 (m, 1H), 7.27-7.28 (m, 1H), 7.25-7.26 (m, 1H), 7.20 (m, 1H), 7.06-7.08 (t, J=4.2 Hz, 2H), 6.70-6.72 (d, J=8.4 Hz, 1H), 6.34-6.36 (d, J=7.2 Hz, 1H), 5.18-5.21 (m, 1H), 5.04-5.05 (d, J=6.8 Hz, 1H), 3.62-3.99 (m, 4H), 3.56-3.62 (m, 2H), 2.45-2.50 (m, 1H), 2.01-2.06 (m, 2H), 1.74-1.80 (m, 2H), 1.62-1.70 (m, 2H), 1.27-1.30 (m, 1H). $[\alpha]_D^{20}$=144.3 (c=0.204 g/100 mL, CHCl₃).

Compound 46: (1S,2S)-2-Phenyl-cyclopropanecarboxylic acid [(R)-1-(6-ethoxy-pyridin-3-yl)-2-methoxy-ethyl]-amide

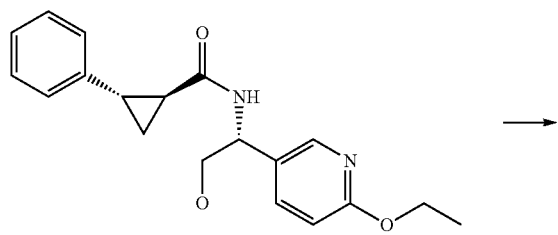

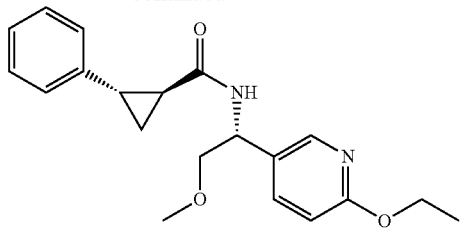

NaH (60% suspension in mineral oil) (2.06 g, 51.5 mmol) was suspended in DMF and the reaction vessel was cooled in an ice bath. (1S,2S)-2-Phenyl-cyclopropanecarboxylic acid [(R)-1-(6-ethoxy-pyridin-3-yl)-2-hydroxy-ethyl]-amide (Compound 33) (15 g, 48 mmol) was dissolved in DMF (50 ml) and added drop wise to the sodium hydride suspension at 5-8 C over 20 minutes. The solution was stirred 30 minutes. Methyl iodide (3.30 ml, 53.0 mmol) dissolved in DMF (25 ml) was added drop wise at 5-12 C over 10 minutes and the mixture was stirred at 7-8 C for 30 minutes. The mixture was added to a brine solution and extracted with EtOAc. The organic layer was washed with more brine, dried (MgSO4) filtered and the solvent was evaporated off. The crude product was purified by silica gel chromatography (eluent EtOAc in heptanes 4:1). The fractions that contained the product was collected and the solvent was removed in vac. The residue was redissolved in THF (50 ml) EtOAc (100 ml) and heptanes (25 ml). The mixture was concentrated until 40 ml remained and cooled in ice. A white solid precipitated and was collected by filtration. Yield: 6.75 g (43%) of Compound 46. LC-MS (m/z) 341.2 (MH+). $t_R$=0.64 min (method B).

1H-NMR (500 MHz, DMSO) δ 8.62 (d, 1H), 8.08 (br s, 1H), 7.63 (d, 1H), 7.27 (m, 1H), 7.17 (m, 1H), 7.10 (d, 2H), 6.74 (d, 1H), 5.05 (m, 1H), 4.26 (m, 2H), 3.55-3.46 (m, 2H), 3.26 (s, 3H), 2.20 (m, 1H), 1.99 (m, 1H), 1.38 (m, 1H), 1.29 (t, 3H), 1.20 (m, 1H).

Compound 47: (1S,2S)—N-[(1R)-2-methoxy-1-[(6-[(3R)-tetrahydrofuran-3-yl]oxy-3-pyridyl]ethyl]-2-phenyl-cyclopropanecarboxamide

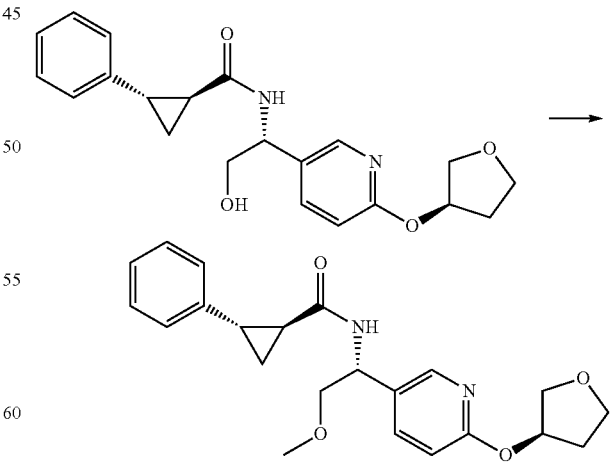

Prepared analogously to Compound 46 using Compound 43 (0.90 g).

Yield=490 mg (53%) as a solid. ¹H NMR (400 MHz, CDCl₃): δ8.12 (d, J=2.4 Hz, 1H), 7.54-7.57 (m, 1H), 7.25-

7.28 (m, 2H), 7.18-7.21 (m, 1H), 7.05-7.07 (m, 2H), 6.68-6.70 (d, J=8.8 Hz, 1H), 6.37-6.39 (d, J=8.0 Hz, 1H), 5.51-5.54 (m, 1H), 5.10-5.12 (m, 1H), 3.87-4.04 (m, 4H), 3.66-3.69 (m, 1H), 3.60-3.63 (m, 1H), 3.38 (s, 3H), 2.45-2.46 (m, 1H), 2.21-2.26 (m, 1H), 1.60-1.68 (m, 2H), 1.25-1.28 (m, 1H). LC-MS: $t_R$=0.53 min (method B), m/z=383.2 [M+H]$^+$. $[\alpha]_D^{20}$=188.2 (C=0.176, CHCl$_3$).

Compound 48: (1S,2S)—N-[(1R)-2-methoxy-1-[6-[(3S)-tetrahydrofuran-3-yl]oxy-3-pyridyl]ethyl]-2-phenyl-cyclopropanecarboxamide

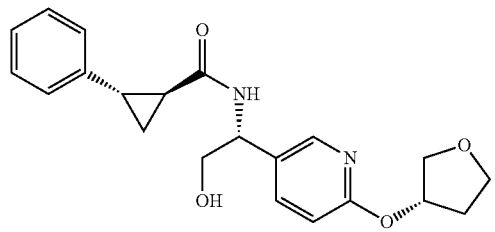

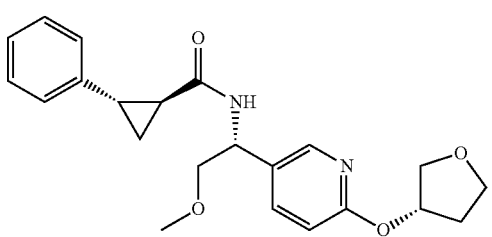

Prepared analogously to Compound 48 using Compound 44 (841 mg).

Yield=645 mg (44%) as a solid. $^1$H NMR (400 MHz, CDCl$_3$): δ8.10-8.11 (d, J=2.4 Hz, 1H), 7.54-7.57 (m, 1H), 7.25-7.28 (m, 2H), 7.18-7.21 (m, 1H), 7.05-7.07 (m, 2H), 6.88-6.70 (d, J=8.8 Hz, 1H), 6.37-68.39 (d, J=8.0 Hz, 1H), 5.51-5.54 (m, 1H), 5.10-5.12 (m, 1H), 3.87-4.04 (m, 4H), 3.66-3.69 (m, 1H), 3.60-3.63 (m, 1H), 3.38 (s, 3H), 2.45-2.46 (m, 1H), 2.21-2.26 (m, 1H), 1.60-1.68 (m, 2H), 1.25-1.28 (m, 1H). LC-MS: $t_R$=0.62 min (method B), m/z=383.2 [M+H]$^+$. $[\alpha]_D^{20}$=162.5 (C=0.225, CHCl$_3$).

Compound 49: (1S,2S)-2-Phenyl-cyclopropanecarboxylic acid {(R)-2-methoxy-1-[6-(tetrahydro-pyran-4-yloxy)-pyridin-3-yl]-ethyl}-amide

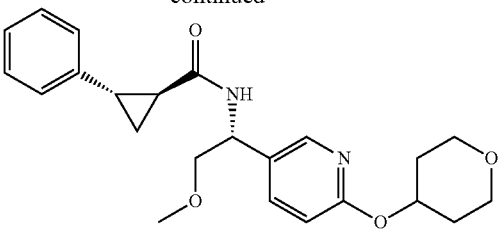

Prepared analogously to Compound 46 using Compound 45. Yield=343 mg (20%) as a solid. $^1$H NMR (400 MHz, COCl$_3$): δ8.10-8.11 (d, J=2.4 Hz, 1H), 7.54-7.57 (m, 1H), 7.25-7.29 (m, 2H), 7.18-7.21 (m, 1H), 7.05-7.07 (m, 2H), 6.66-6.88 (t, J=4.2 Hz, 1H), 6.38-4.40 (d, J=7.2 Hz, 1H), 5.20-5.21 (m, 1H), 5.10-5.12 (m, 1H), 3.94-3.99 (m, 2H), 3.57-3.69 (m, 4H), 3.37 (s, 3H), 2.42-2.49 (m, 1H), 2.02-2.08 (m, 2H), 1.61-1.79 (m, 4H), 1.25-1.28 (m, 1H) $[\alpha]_D^{20}$=159.3 (c=0.198 g/100 mL, CHCl$_3$). LC-MS (m/z) 383.15 (MH+), $t_R$=0.54 min (method B).

Compound 50: (1S,2S)-2-Phenyl-cyclopropanecarboxylic acid {(S)-1-[6-(oxetan-3-yloxy)-pyridin-3-yl]-ethyl}-amide

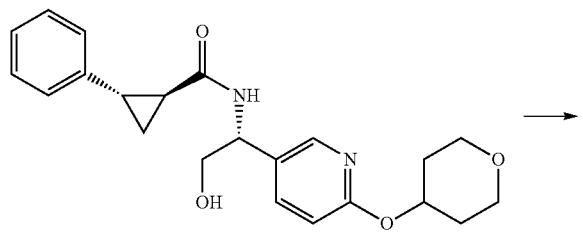

(1S,2S)-2-Phenyl-cyclopropanecarboxylic acid [(S)-1-(6-chloro-pyridin-3-yl)-ethyl]-amide (Compound 18) (2.00 g, 6.65 mmol) was dissolved in DMF (40 ml). N,N-dimethylhydroxylaminehydrochloride (5.00 g, 51.2 mmol) and dicesium carbonate (25 g, 76.7 mmol) were added and the mixture was heated at 95 C 3 days. The mixture was poured out into brine and extracted with EtOAc. The organic layer was washed with brine, dried (MgSO4) and was filtered and then evaporated to dryness. The residue was transferred to a silica gel column and eluded with EtOAc to give Compound 60 as a solid. This sold was dissolved in a mixture of THF (10 ml), EtOAc (10 ml) and heptanes (10 ml). The mixture was concentrated to approx. 10 ml volume and this solution was cooled in an ice/water bath. A white precipitate formed. The solids was collected by filtration and dried in vacuo to give the title compound as a white solid (0.044 g, 2%). 1H-NMR (500 MHz, DMSO) δ 8.43 (d, 1H), 8.02 (s, 1H), 7.45 (d, 1H), 7.25 (m, 2H), 7.17 (m, 1H), 7.10 (d, 2H), 6.61 (d, 1H), 4.83 (m, 1H), 3.98 (m, 6H), 2.19 (m, 1H), 1.90 (m, 1H), 1.35 (m, 4H), 1.21 (m, 1H). LC-MS (m/z) 310.2 (MH+), $t_R$=0.46 min (method B). Mp=171-181 C.

Compound 61: (1S,2S)-2-Phenyl-cyclopropanecarboxylic acid [(S)-1-(6-ethanesulfonyl-pyridin-3-yl)-ethyl]-amide

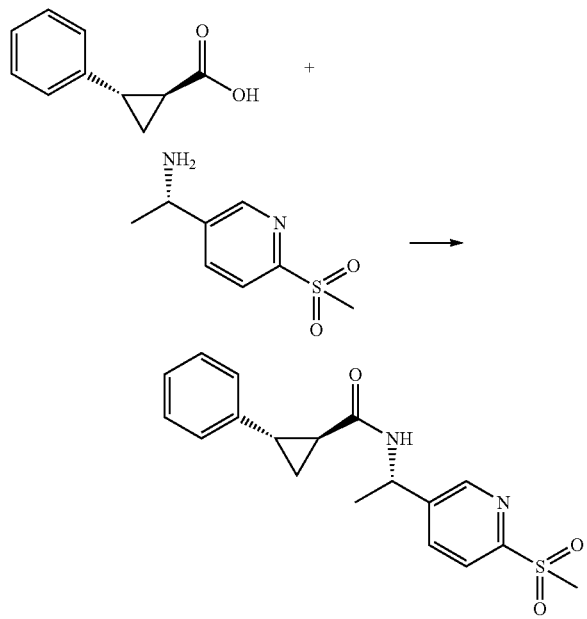

Prepared analogously to Compound 1 using IM46 and (S)-1-(6-Methanesulfonyl-pyridin-3-yl)-ethylamine (prepared from 1-(6-Methanesulfonyl-pyridine-3-yl)-ethanone analogously to IM24, which was prepared from commercially available 5-Bromo-2-methanesulfonyl-pyridine CAS 98626-95-0). Yield from IM48=1.54 g (68%). 1H-NMR (500 MHz, DMSO) δ 8.80 (d, 1H), 8.72 (s, 1H), 8.02 (m, 2H), 7.27 (m, 2H), 7.20 (s, 1H), 7.12 (d, 2H), 5.08 (m, 1H), 3.27 (s, 3H), 2.20 (m, 1H), 1.95 (m, 1H), 1.42 (d, 3H), 1.37 (m, 1H), 1.22 (m, 1H), LC-MS (m/z) 345.1 (MH+), $t_R$=1.21 min (method A).

Compound 52: (1S,2S)-2-Phenyl-cyclopropanecarboxylic acid [(R)-1-(5-ethoxy-pyridin-2-yl)-2-hydroxy-ethyl]-amide

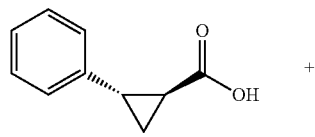

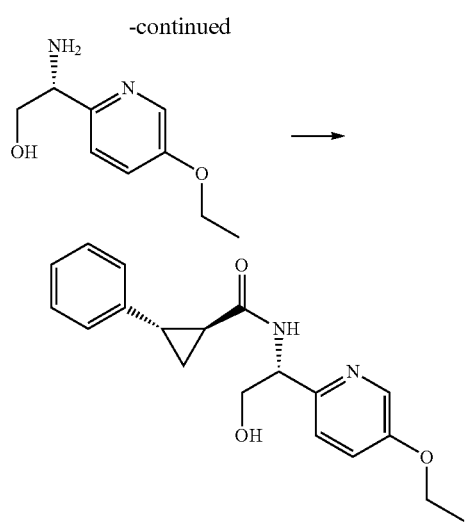

Prepared analogously to Compound 21 using IM46 and (R)-2-Amino-2-(5-ethoxy-pyridin-2-yl)-ethanol (prepared from commercially available 2-Bromo-5-ethoxy-pyridine CAS 42834-01-5 analogously to IM36). Compound 52 was further purified by SFC (Column: Chiralpack OJ250×30 mm, Mobile phase: Supercritical $CO_2$/MeOH+$NH_4OH$=55/45 at 50 mL/min, column temperature: 38° C., Nozzle Pressure: 100 Bar, Nozzle Temp=60° C., Evaporator temp=20 C, Trimmer temp=25° C., Detector: 220 nm). Yield=163 mg. 1H NMR (CDCl3 400 MHz, TMS): δ 8.15 (d, J=2.8 Hz, 1H), 7.08-7.31 (m, 6H), 7.06 (d, J=7.2 Hz, 2H), 5.11-5.15 (m, 1H), 4.00-4.08 (m, 3H), 3.87-3.90 (m, 1H), 2.47-2.52 (m, 1H), 1.63-1.76 (m, 3H), 1.43 (t, J=7.2 Hz, 3H), 1.27-1.31 (m, 1H); [α]20, D=182.0 (c=0.234 g/100 mL, EtOH)

In Vitro Assays

The nicotinic acetylcholine receptor α7 is a calcium-permeable ion channel, whose activity can be measured by over expression in mammalian cells or oocytes. These two individual assays are described in Example 2 and 3, respectively.

Example 2

α7 NNR Flux Assay

The nicotinic acetylcholine receptor α7 is a calcium-permeable ion channel, whose activity can be measured by over expression in mammalian cells or oocytes. In this version of the assay, the human α7 receptor is stably expressed in the rat GH4C1 cell line. The assay was used to identify positive allosteric modulators (PAMs) of the α7 receptor. Activation of the channel was measured by loading cells with the calcium-sensitive fluorescent dye Calcium-4 (Assay kit from Molecular Devices), and then measuring real-time changes in fluorescence upon treatment with test compounds.

The cell line ChanClone GH4C1-nAChRalpha7 from Genionics was seeded from frozen stock in 384-well plates in culture media 2-3 days before experiment to form an approximately 80% confluent layer on the day of experiment.

Cell Plating and Dye Loading

The cell culture were split into "22.5 cm×22.5 cm"-plates with approximately 100×$10^3$ cells/$cm^2$. After four days incubation in a humidified incubator at 37° C. and 5% $CO_2$, it had grown to an 80-90% confluent layer, and the cell were harvested.

Culture Media:
- 500 mL DMEM/F12 (Gibco 31331)
- 50 mL FBS (Gibco 10091-155, lot 453289FD)
- 5 mL Sodium Pyruvate (Gibco 11360)
- 5 mL Pen/Strep (Gibco 15140)
- 0.1 mg/mL G-418 (Gibco 11811-064)

Two or three days before the experiment the cells were seeded in 384 well plates from Greiner bio-one (781946. CELLCOAT. Poly-D-Lysine, black, µClear).

The media was poured off and the plate washed with PBS and left to drain. 5 mL Trypsin was added, cells were washed and incubated (at room temperature) for about 10 seconds. Trypsin was poured of quickly and the cells were incubated for 2 minutes at 37° C. (if the cells were not already detached). Cells were resuspended in 10 mL culture media and transferred to 50 mL tubes.

The cell suspension was counted (NucleoCounter, total cell count) from the first plates to estimate the total cell number of the whole batch.

The cells were seeded in 384 well plates with 30 µL/well (30000 cells/well) while stirring the cell suspension or otherwise preventing the calls from precipitating.

The plates were incubated at room temperature for 30-45 minutes.

The plates were placed in incubator for two days (37° C. and 5% $CO_2$).

Loading the Cells

The loading buffer was 5% v/v Calcium-4 Kit and 2.5 mM Probenecid in assay buffer.
- 190 mL assay buffer
- 10 mL Kit-solution
- 2 mL 250 mM Probenecid This volume was enough for 3×8 cell plates.

Culture media were removed from the cell plates and 20 µL loading buffer was added in each well. The cell plates were placed in trays and incubated 90 minutes in the incubator (37° C.). Thereafter the plates were incubated 30 minutes at room temperature, still protected from light.

Now the cell plates were ready to run in the Functional Drug Screening System (FDSS).

The assay buffer was HBSS with 20 mM HEPES, pH 7.4 and 3 mM $CaCl_2$.

FDSS Ca Assay 200 nL 10 mM compound solution in DMSO was diluted in 50 µL assay buffer. The final test concentrations in the cell plates were 20-10-5-2.5-1.25-0.625-0.312-0.156-0.078-0.039 µM. Assay buffer and 3 µM PNU-120596 were used for control.

The agonist acetylcholine was added to a final concentration of 20 µM (~EC100).

In the FDSS7000 the Ex480-Em540 was measured with 1 second intervals. The baseline was made of 5 frames before addition of test compounds, and 95 frames more were made before addition of acetylcholine. The measurement stopped 30 frames after the $2^{nd}$ addition.

Raw data for each well were collected as "the maximum fluorescence count" in the interval 100-131 seconds and as "the average fluorescence count" in the interval 96-100 seconds. The positive allosteric modulation in the $2^{nd}$ addition was the enhancement of agonist response with test compound compared to agonist alone.

Results were calculated as % modulation of test compound compared to the reference PNU-120596 set to 100%. From these data $EC_{50}$ curves were generated giving $EC_{50}$, hill and maximum stimulation.

The compounds of the invention were shown to be PAMs of the α7 receptor. The compounds of the present invention characterized in the flux assay generally possess $EC_{50}$ values below 20.000 nM or less such as below 10.000 nM. Many compounds, in fact have $EC_{50}$ values below 5,000 mM. Table 1 shows $EC_{50}$ values for exemplified compounds of the invention.

TABLE 1

| Compound | $EC_{50}$ (nM) |
|---|---|
| 1 | 670 |
| 2 | 5600 |
| 3 | 5800 |
| 4 | 8100 |
| 5 | 7700 |
| 6 | 5200 |
| 7 | 960 |
| 8 | 3700 |
| 9 | 6200 |
| 10 | 1900 |
| 11 | 3800 |
| 12 | 1200 |
| 13 | 1600 |
| 14 | 1600 |
| 15 | 5600 |
| 16 | 6800 |
| 17 | 3700 |
| 18 | 3700 |
| 19 | 2400 |
| 20 | 2000 |
| 21 | 640 |
| 22 | 5500 |
| 23 | 7600 |
| 24 | 5200 |
| 25 | 7300 |
| 26 | 390 |
| 27 | 390 |
| 28 | 620 |
| 29 | 860 |
| 30 | 560 |
| 31 | 1700 |
| 32 | 530 |
| 33 | 1000 |
| 34 | 700 |
| 35 | 710 |
| 36 | 1600 |
| 37 | 700 |
| 38 | 970 |
| 39 | 720 |
| 40 | 890 |
| 41 | 1600 |
| 42 | 790 |
| 43 | 2900 |
| 44 | 4600 |
| 45 | 2900 |
| 46 | 460 |
| 47 | 1000 |
| 48 | 1700 |
| 49 | 1200 |
| 50 | 3200 |
| 51 | 7200 |
| 52 | 2000 |

Example 3

α7NNR Oocyte Assay

Expression of α7 nACh Receptors in *Xenopus* oocytes

Oocytes were surgically removed from mature female *Xenopus laevis* anaesthetized in 0.4% MS-222 for 10-15 min. The oocytes were then digested at room temperature for 2-3 hours with 0.5 mg/mL collegenase (type IA Sigma-Aldrich) in OR2 buffer (82.5 mM NaCl, 2.0 mM KCl, 1.0 mM $MgCl_2$ and 5.0 mM HEPES, pH 7.6). Oocytes avoid of the follicle layer were selected and incubated for 24 hours in Modified Barth's Saline buffer (88 mM NaCl, 1 mM KCl. 15 mM HEPES, 2.4 mM NaHCO$_3$, 0.41 mM CaCl$_2$, 0.82 mM MgSO$_4$. 0.3 mM Ca(NO$_3$)$_2$) supplemented with 2 mM sodium pyruvate, 0.1 U/l penicillin and 0.1 µg/l streptomycin. Stage IV oocytes were identified and injected with 4.2-48 nl of nuclease free water containing 0.1-1.2 ng of cRNA coding for human α7 nACh receptors or 3.0-32 ng of cRNA coding for rat α7 nACh receptors and incubated at 18° C. for 1-10 days when they were used for electro-physiological recordings.

Electrophysiological Recordings of α7 nACh Receptors Expressed in Oocytes.

Oocytes were used for electrophysiological recordings 1-10 days after injection. Oocytes were placed in a 1 mL bath and perfused with Ringer buffer (115 mM NaCl, 2.5 mM KCl, 10 mM HEPES, 1.8 mM CaCl$_2$, 0.1 mM MgCl$_2$, pH 7.5). Cells were impaled with agar plugged 0.2-1 MΩ electrodes containing 3 M KCl and voltage clamped at −90 mV by a GeneClamp 500B amplifier. The experiments were performed at room temperature. Oocytes were continuously perfused with Ringer buffer and the drugs were applied in the perfusate. ACh (30 µM) applied for 30 sec were used as the standard agonist for activation of the α7 nACh receptors. In the standard screening set-up the new test compound (10 µM or 30 µM) were applied for 1 min of pre-application allowing for evaluation of agonistic activity followed by 30 sec of co-application with ACh (30 µM) allowing for evaluation of PAM activity. The response of co-application was compared to the agonistic response obtained with ACh alone. The drug induced effects on both the peak response and the total charge (AUC) response were calculated thus giving the effect of drug induced PAM activity as fold modulation of the control response.

For more elaborate studies doses-response curves can be performed for evaluation of max-fold modulation and EC$_{50}$ values for both peak and AUC responses.

The invention claimed is:
1. A compound according to formula [I]

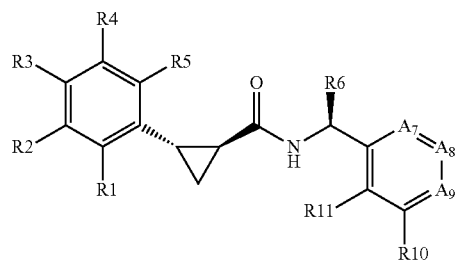

[I]

wherein R1, R2, R3, R4 and R5 are each H;
R6 is hydroxymethyl;
A$_7$ is C—R7 or N, A$_8$ is C—R8 or N and A$_9$ is C—R9 or N, provided that at least one of A$_7$, A$_8$ or A$_9$ is N and no more than two of A$_7$, A$_8$ and A$_9$ is N;
R7, R8, R9, R10 and R11 are selected independently of each other from H, C$_{1-6}$alkyl, C$_{2-6}$alkenyl, C$_{2-6}$alkynyl, C$_{1-6}$alkoxy, cyano, NR12R13, C$_{1-6}$alkylsulfonyl, halogen and OR14, wherein said C$_{1-6}$alkyl, C$_{2-6}$alkenyl, C$_{2-6}$alkynyl or C$_{1-6}$alkoxy is optionally substituted with one or more substituents selected from chlorine, fluorine, C$_{1-6}$alkoxy, cyano and NR12R13;
R12 and R13 independently represent hydrogen, C$_{1-6}$alkyl, C$_{2-6}$alkenyl and C$_{2-6}$alkynyl;

R14 represents a monocyclic saturated ring moiety having 4-6 ring atoms wherein one of said ring atoms is O and the others are C;
or R9 and R10 may be linked together to form the moiety indicated below

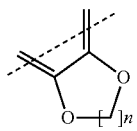

wherein n is 1, 2 or 3;
or a pharmaceutically acceptable salt thereof.
2. The compound according to claim 1, wherein R7, R8, R9, R10 and R11 are selected independently of each other from H, C$_{1-4}$alkyl, C$_{1-4}$alkoxy, cyano, —N(CH$_3$)$_2$, methylsulfonyl, fluorine, chlorine and OR14, wherein said C$_{1-4}$alkyl or C$_{1-4}$alkoxy is optionally substituted with one or more substituents selected from fluorine, C$_{1-4}$alkoxy and cyano;
R14 represents a monocyclic saturated ring moiety having 4-6 ring atoms wherein one of said ring atoms is O and the others are C;
or R9 and R10 may be linked together to form the moiety indicated below

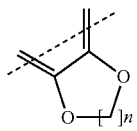

wherein n is 1 or 2.
3. The compound according to claim 1, wherein R7, R8, R9, R10 and R11 are selected independently from H, C$_{1-4}$alkyl, C$_{2-4}$alkenyl, C$_{2-4}$alkynyl, C$_{1-4}$alkoxy, cyano and halogen, wherein said C$_{1-4}$alkyl, C$_{2-4}$alkenyl, C$_{2-4}$alkynyl or C$_{1-4}$alkoxy is optionally substituted with one or more substituents selected from fluorine and C$_{1-4}$alkoxy.
4. The compound according to claim 1, wherein one or more of the hydrogen atoms are represented by deuterium.
5. The compound according to claim 4, wherein at least about 85% of the compound has a deuterium atom at each position designated as deuterium, and any atom not designated as deuterium is present at about its natural isotopic abundance.
6. The compound according to claim 1, wherein no more than one of A$_7$, A$_8$ or A$_9$ is N.
7. The compound according to claim 1 having a diastereomeric excess of at least 80%.
8. The compound according to claim 1 selected from
21: (1S,2S)-2-Phenyl-cyclopropanecarboxylic acid [(R)-2-hydroxy-1-(6-propoxy-pyridin-3-yl)-ethyl]-amide;
22: (1S,2S)-2-Phenyl-cyclopropanecarboxylic acid [(R)-2-hydroxy-1-(6-trifluoromethyl-pyridin-3-yl)-ethyl]-amide;
23: (1S,2S)-2-Phenyl-cyclopropanecarboxylic acid [(1?)-1-(5-cyano-pyridin-2-yl)-2-hydroxy-ethyl]-amide;
24: (1S,2S)-2-Phenyl-cyclopropanecarboxylic acid [(R)-2-hydroxy-1-(6-methoxy-pyridin-3-yl)-ethyl]-amide;
25: (1S,2S)-2-Phenyl-cyclopropanecarboxylic acid [(R)-2-hydroxy-1-(6-methyl-pyridin-3-yl)-ethyl]-amide;
26: (1S,2S)-2-Phenyl-cyclopropanecarboxylic acid [(R)-2-hydroxy-1-(6-isopropoxy-pyridin-3-yl)-ethyl]-amide;

31: (1S,2S)-2-Phenyl-cyclopropanecarboxylic acid [(R)-1-(6-(2,2,2-d$_3$)-ethoxy-pyridin-3-yl)-2-hydroxy-ethyl]-amide;

33: (1S,2S)-2-Phenyl-cyclopropanecarboxylic acid [(R)-1-(6-ethoxy-pyridin-3-yl)-2-hydroxy-ethyl]-amide;

36: (1S,2S)-2-Phenyl-cyclopropanecarboxylic acid [(R)-1-(6-(1,1-d$_2$)-ethoxy-pyridin-3-yl)-2-hydroxy-ethyl]-amide;

38: (1S,2S)-2-Phenyl-cyclopropanecarboxylic acid [(R)-1-(6-(1,1,2,2,2-d$_5$)-ethoxy-pyridin-3-yl)-2-hydroxy-ethyl]-amide;

40: (1S,2S)-2-Phenyl-cyclopropanecarboxylic acid [(R)-1-(6-cyclobutoxy-pyridin-3-yl)-2-hydroxy-ethyl]-amide;

43: (1S,2S)-2-Phenyl-cyclopropanecarboxylic acid ((R)-2-hydroxy-1-{6-[(R)-(tetrahydro-furan-3-yl)oxy]-pyridin-3-yl}-ethyl)-amide;

44: (1S,2S)—N-[(1R)-2-hydroxy-1-[6-[(3S)-tetrahydrofuran-3-yl]oxy-3-pyridyl]ethyl]-2-phenyl-cyclopropanecarboxamide;

45: (1S,2S)-2-((Z)-1-Methylene-penta-2,4-dienyl)-cyclopropanecarboxylic acid {(R)-2-hydroxy-1-[6-(tetrahydro-pyran-4-yloxy)-pyridin-3-yl]-ethyl}-amide;

or a pharmaceutically acceptable salt of any of these compounds.

9. The compound according to claim 8, wherein the compound is
21: (1S,2S)-2-Phenyl-cyclopropanecarboxylic acid [(R)-2-hydroxy-1-(6-propoxy-pyridin-3-yl)-ethyl]-amide.

10. The compound according to claim 8, wherein the compound is
26: (1S,2S)-2-Phenyl-cyclopropanecarboxylic acid [(R)-2-hydroxy-1-(6-isopropoxy-pyridin-3-yl)-ethyl]-amide.

11. The compound according to claim 8, wherein the compound is
31: (1S,2S)-2-Phenyl-cyclopropanecarboxylic acid [(R)-1-(6-(2,2,2-d$_3$)-ethoxy-pyridin-3-yl)-2-hydroxy-ethyl]-amide.

12. The compound according to claim 8, wherein the compound is
33: (1S,2S)-2-Phenyl-cyclopropanecarboxylic acid [(R)-1-(6-ethoxy-pyridin-3-yl)-2-hydroxy-ethyl]-amide.

13. The compound according to claim 8, wherein the compound is
36: (1S,2S)-2-Phenyl-cyclopropanecarboxylic acid [(R)-1-(6-(1,1-d$_2$)-ethoxy-pyridin-3-yl)-2-hydroxy-ethyl]-amide.

14. Newly Added) The compound according to claim 8, wherein the compound is
38: (1S,2S)-2-Phenyl-cyclopropanecarboxylic acid [(1?)-1-(6-(1,1,2,2,2-d$_5$)-ethoxy-pyridin-3-yl)-2-hydroxy-ethyl]-amide.

15. The compound according to claim 8, wherein the compound is
40: (1S,2S)-2-Phenyl-cyclopropanecarboxylic acid [(R)-1-(6-cyclobutoxy-pyridin-3-yl)-2-hydroxy-ethyl]-amide.

16. A method for the treatment of a disease or disorder comprising administering a therapeutically effective amount of a compound according to claim 1 to a patient in need thereof, wherein the disease or disorder is selected from the group consisting of psychosis; schizophrenia; cognitive disorders; cognitive impairment associated with schizophrenia; Attention Deficit Hyperactivity Disorder (ADHD); autism spectrum disorders, Alzheimer's disease (AD); mild cognitive impairment (MCI); age associated memory impairment (AAMI); senile dementia; AIDS dementia; Pick's disease; dementia associated with Lewy bodies; dementia associated with Down's syndrome; Huntington's Disease; Parkinson's disease (PD); obsessive-compulsive disorder (OCD); traumatic brain injury; epilepsy; post-traumatic stress; Wernicke-Korsakoff syndrome (WKS); post-traumatic amnesia; cognitive deficits associated with depression; diabetes, weight control, inflammatory disorders, reduced angiogenesis; amyotrophic lateral sclerosis and pain.

17. A pharmaceutical composition comprising a compound according to claim 1 and one or more pharmaceutically acceptable carriers or excipients.

18. A kit comprising a compound according to claim 1, together with a second compound selected from the group consisting of acetylcholinesterase inhibitors; glutamate receptor antagonists; dopamine transport inhibitors; noradrenalin transport inhibitors; D2 antagonists; D2 partial agonists; PDE10 antagonists; 5-HT2A antagonists; 5-HT6 antagonists; KCNQ antagonists; lithium; sodium channel blockers and GABA signaling enhancers.

* * * * *

UNITED STATES PATENT AND TRADEMARK OFFICE
CERTIFICATE OF CORRECTION

PATENT NO.       : 9,050,327 B2
APPLICATION NO.  : 14/054941
DATED            : June 9, 2015
INVENTOR(S)      : Jorgen Eskildsen et al.

Page 1 of 1

It is certified that error appears in the above-identified patent and that said Letters Patent is hereby corrected as shown below:

In the Claims:

Please amend claim 8 at column 82, line 59, to recite
"23: (1S,2S)-2-Phenyl-cyclopropanecarboxylic acid
[(R)-1-(5-cyano-pyridin-2-yl)-2-hydroxy-ethyl]-amide;"
in lieu of "23: (1S,2S)-2-Phenyl-cyclopropanecarboxylic acid
[(1?)-1-(5-cyano-pyridin-2-yl)-2-hydroxy-ethyl]-amide;".

Please amend claim 14 at column 84, line 6, to recite
"38: (1S,2S)-2-Phenyl-cyclopropanecarboxylic acid
[(R)-1-(6-(1,1,2,2,2-$d_5$)-ethoxy-pyridin-3-yl]-2-hydroxy-ethyl]-amide"
in lieu of "38: (1S,2S)-2-Phenyl-cyclopropanecarboxylic acid
[(1?)-1-(6-(1,1,2,2,2-$d_5$)-ethoxy-pyridin-3-yl)-2-hydroxy-ethyl]-amide".

Signed and Sealed this
Twentieth Day of October, 2015

Michelle K. Lee
*Director of the United States Patent and Trademark Office*